United States Patent
Roland et al.

(10) Patent No.: US 11,254,713 B2
(45) Date of Patent: Feb. 22, 2022

(54) METHOD TO ENHANCE IMMUNOGENICITY OF LIVE TYPHOID VACCINES AND CARRIERS

(71) Applicant: ARIZONA BOARD OF REGENTS ON BEHALF OF ARIZONA STATE UNIVERSITY, Scottsdale, AZ (US)

(72) Inventors: Kenneth Roland, Mesa, AZ (US); Amanda M. Tafoya, Laveen, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 748 days.

(21) Appl. No.: 15/968,517

(22) Filed: May 1, 2018

(65) Prior Publication Data
US 2018/0312550 A1 Nov. 1, 2018

Related U.S. Application Data

(60) Provisional application No. 62/492,349, filed on May 1, 2017.

(51) Int. Cl.
| | |
|---|---|
| C07K 14/255 | (2006.01) |
| A61K 31/7115 | (2006.01) |
| A61K 39/112 | (2006.01) |
| A61K 39/00 | (2006.01) |

(52) U.S. Cl.
CPC ........ C07K 14/255 (2013.01); A61K 39/0275 (2013.01); A61K 2039/522 (2013.01)

(58) Field of Classification Search
None
See application file for complete search history.

(56) References Cited

U.S. PATENT DOCUMENTS

| | | |
|---|---|---|
| 8,465,755 B2 | 6/2013 | Curtiss et al. |
| 9,040,059 B2 | 5/2015 | Curtiss et al. |
| 9,580,718 B2 | 2/2017 | Curtiss et al. |
| 2017/0327830 A1 | 11/2017 | Curtiss et al. |

FOREIGN PATENT DOCUMENTS

| | | |
|---|---|---|
| WO | 2015167903 A1 | 11/2015 |
| WO | 2019010135 A1 | 1/2019 |

OTHER PUBLICATIONS

Li et al. A sopB Deletion Mutation Enhances the Immunogenicity and Protective Efficacy of a Heterologous Antigen Delivered by Live Attenuated *Salmonella enterica* Vaccines. Infection and Immunity. Published online Sep. 2008. vol. 76, No. 11, pp. 5238-5246. (Year: 2008).*
Narayanan et al. Arabinose-Induction of lac-derived Promoter Systems for Penicillin Acylase Production in *Escherichia coli*. Sep. 5, 2008. vol. 22, Issue 3, pp. 617-625. (Year: 2008).*
Nicholson et al. (*Salmonella enterica* Serotype Typhimurium Elicits Cross-Immunity against a *Salmonella enterica* Serotype Enteritidis Strain Expression LP Fimbriae from the lac Promoter. Jan. 2001. Infection and Immunity. vol. 69, No. 1, pp. 204-212. (Year: 2001).*
Ziemann et al. Gene name errors are widespread in the scientific literature. 2016. Genome Biology. vol. 17, No. 177, 3 pages. (Year: 2016).*
McK

(56) References Cited

OTHER PUBLICATIONS

Hashizume, T , et al., "Peyer's Patches Are Required for Intestinal Immunoglobulin A Responses to *Salmonella* spp", Infection and Immunity 76, 927-934 (2008).
Hitchcock, P , et al., "Morphological heterogeneity among *Salmonella* lipopolysaccharide chemotypes in silver-stained polyacrylamide gels", J Bacteriol 154, 269-277 (1983).
Hoare, A , et al., "The outer core lipopolysaccharide of *Salmonella enterica* serovar Typhi is required for bacterial entry into epithelial cells", Infect Immun 74(3), 1555-1564 (2006).
Hohmann, E , et al., "phoP/phoQ-deleted *Salmonella typhi* (Ty800) is a safe and immunogenic single-dose typhoid fever vaccine in volunteers", J Infect Dis 173(6), 1408-1414 (1996).
Kim, D , et al., "The airway antigen sampling system: respiratory M cells as an alternative gateway for inhaled antigens", J Immunol 186(7), 4253-4262 (2011).
Kiyono, H , "NALT—versus Peyer's-patch-mediated mucosal immunity", Nat Rev Immunol 4(9), 699-710 (2004).
Kohbata, S , et al., "Cytopathogenic Effect of *Salmonella typhi* GIFU 10007 on M cells of Murine Ileal Peyer's Patches in Ligated Ileal Loops : An Ultrastructural Study", Microbiol Immunol 30, 1225-1237 (1986).
Kopecko, D , et al., "Genetic stability of vaccine strain *Salmonella typhi* Ty21a over 25 years", Int J Med Microbiol 299(4), 233-246 (2009).
Ledeboer, N , et al., "*Salmonella enterica* Serovar Typhimurium Requires the Lpf, Pef, and Tafi Fimbriae for Biofilm Formation on HEp-2 Tissue Culture Cells and Chicken Intestinal Epithelium", Infection and Immunity 74, 3156-3169 (2006).
Lymberopoulos, M , et al., "Characterization of Stg Fimbriae from an Avian Pathogenic *Escherichia coli* O78:K80 Strain and Assessment of Their Contribution to Colonization of the Chicken Respiratory Tract", J Bacteriol 188, 6449-6459 (2006).
Martinoli, C , et al., "Entry route of *Salmonella typhimurium* directs the type of induced immune response", Immunity 27, 975-984 (2007).
Mroczenski-Wildey, M , et al., "Invasion and lysis of HeLa cell monolayers by *Salmonella typhi*: the role of lipopolysaccharide", Microbial Pathogenesis 6(2), 143-152 (1989).
Norris , et al., "Expression and transcriptional control of the *Salmonella typhimurium* lpf fimbrial operon by phase variation". Mol Microbiol 29, 311-320 (1998).
Parkhill, J , et al., "Complete genome sequence of a multiple drug resistant *Salmonella enterica* serovar Typhi CT18", Nature 413, 848-852 (2001).
Pascopella, L , et al., "Host restriction phenotypes of *Salmonella typhi* and *Salmonella gallinarum*", Infection and Immunity 63, 4329-4335 (1995).
Penheiter, K , et al., "Non-invasive *Salmonella typhimurium* mutants are avirulent because of an inability to enter and destroy M cells of ileal Peyer's patches", Mol Microbiol 24, 697-709 (1997).
Pielage, J , et al., "Reversible differentiation of Caco-2 cells reveals galectin-9 as a surface marker molecule for human follicle-associated epithelia and M cell-like cells", Int J Biochem Cell Biol 39, 1886-1901 (2007).
Raffatellu, M , et al., "Clinical pathogenesis of typhoid fever", J Infect Dev Ctries 2, 260-266 (2008).
Roland, K , et al., "Reactogenicity and immunogenicity of live attenuated *Salmonella enterica* serovar Paratyphi A enteric fever vaccine candidates", Vaccine 28(21), 3679-3687 (2010).
Shi, H , et al., "Immunogenicity of a live recombinant *Salmonella enterica* serovar typhimurium vaccine expressing pspA in neonates and infant mice born from naive and immunized mothers", Clin Vaccine Immunol 17(3), 363-371 (2010).
Stratford, R , et al., "Optimization of *Salmonella enterica* serovar typhi DeltaaroC DeltassaV derivatives as vehicles for delivering heterologous antigens by chromosomal integration and in vivo inducible promoters", Infect Immun 73(1), 362-368 (2005).
Townsend , et al., "*Salmonella enterica* Serovar Typhi Possesses a Unique Repertoire of Fimbrial Gene Sequences", Infect Immun 69(5), 2894-2901 (2001).
Wang, J , et al., "Convergent and divergent development among M cell lineages in mouse mucosal epithelium", J Immunol 187(10), 5277-5285 (2011).
Weening, E , et al., "The *Salmonella enterica* Serotype Typhimurium lpf, bet, stb, stc, std, and sth Fimbrial Operons Are Required for Intestinal Persistence in Mice", Infection and Immunity 73, 3358-3366 (2005).
Winter, S , et al., "*Salmonella enterica* Serovar Typhi conceals the invasion-associated type three secretion system from the innate immune system by gene regulation", PLoS Pathog 10(7), e1004207, 15 pages (2014).
Winter, S , et al., "The *Salmonella enterica* serotype Typhi regulator TviA reduces interleukin-8 production in intestinal epithelial cells by repressing flagellin secretion", Cell Microbiol 10, 247-261 (2008).

\* cited by examiner

Figure 7A

```
         10        20        30        40        50        60        70        80        90       100
GCGGGATCCCGCAGTGATAAGAGGTCTTGTGGCGGAAGTAGGGTGCTAACCTTCTGCGTTATGTTTGCGCTGTTAATTATGTCGGCTGGCACTTTCCAGCA
CGGCCTAGGGCGTCACTATTGTCGGAGAACACCGCCTTCATCCCACGATTGGAAGACGCAATAGAAACGCGACAATTAATAGAGCGGACCGTGAAAGGTGGT 110       120       130       140       150       160       170       180       190       200
CTATTCGCCAGCGCGACGGGAGGGGGTTAGCGAAGCGGTCTGCGTAACACATGCAAGACCAGGCGTACAGCGCACCCATTTGGTGCCCTTTTTTTTATTT
GATAAGCGGTCGGCGTCGCCCTCCCCCAATCGGTTCGCAGACGCATTCTGTACGTTGTGGTCCGCATGTCGCGTGGGTAAACCACGGGAAAAAAAATAAA 210       220       230       240       250       260       270       280       290       300
AGCACAAATACCTAATCAATTGTAGTTAAAAAAACGTCTAATAAATAAGGAAGACATTTAACTTATTTATGAATAGGAAGAAATAATATATTAATTATAT
TCGTGTTTATGGATTAGTTAACATCAATTTTTTTGCAGATTATTTATTCCTTCTGTAAATTGAATAAATACTTATCCTTCTTTATTATATAATTAATATA 310       320       330       340       350       360       370       380       390       400
TAATTTATTCTTAATAAAAAATTACATTTATGTACATTCCATTTGTAATATATTGATTTCTATTCTTTTTAAGATTAACTAACAATTATTTTTATATATA
ATTAAATAAGAATTATTTTTTAATGTAAATACATGTAAGGTAAACATTATATAACTAAAGATAAGAAAAATTCTAATTGATTGTTAATAAAAATATATAT 410       420       430       440       450       460       470       480       490       500
CTAATTATAGTATCCAATAGCCACCTCTATACACTCCATTTCCTCACAGAATGCAGATAATCCTAAGGATGCGTTCTGTTATCTACCGTCATAAATGGAG
GATTAATATCATAGGTTATGGGTGGAGATATGTGAGGTAAAGGAGTGTCTTACGTCTATTAGGATTCCTACGCAAGACAATAGATGGCAGTATTTACCTC
                                                                                               M  E>
                                                                                          _____/

510       520       530       540       550       560       570       580       590       600
TTTTTAATGAAAAAGGTTGTTTTTGCTCTGTCTGCTGTCGCTGTAGTTTCCAGTTCTGCTTTCGCTGCTGAATCTGGTGACGGCACCATTAAATTCACCG
AAAAATTACTTTTTCCAACAAAAACGAGACAGACGAGAGCGACATCAAAGGTGAAGACGAAAGCGACGACTTAGACCACTGCCGTGGTAATTTAAGTGGC
 F  L  M  K  K  V  V  F  A  L  S  A  L  A  V  V  S  T  S  A  F  A  A  E  S  G  D  G  T  I  K  F  T>
                              LPFA                                                                >

610       620       630       640       650       660       670       680       690       700
GTGAAATCGTTGACGCGCCATGGGTCGGTTTCTACTGACTGGGCAGAACCAGGAAGTTGTGCTGGGTCAGGGTTAAGAAAAAATATCTTCAAAGCCATTGGCGA
GACTTTAGCAACTGCGCGGGTAGGGCAGCAAAGATGACTGAGGGTCTTGGTCCTTCAACAGGACCGAGTCCAATTCTTTTTATAGAAGTTTCGGTAACCGCT
 G  E  I  V  D  A  P  C  V  V  S  T  D  S  Q  N  Q  E  V  V  L  G  Q  V  K  K  N  I  F  K  A  I  G  D>
                              LPFA                                                                 /

710       720       730       740       750       760       770       780       790       800
CAAGTCTTCTTCTAAGCCTTCCAGATCAAACTGGAAGACGTGTGACATCACCTCTAATACCAAAGTTAACGTAAGCTTCAATGGCGTTGGTGATACAGAC
GTTCAGAAGAAGATTCGGAAAGGTCTAGTTTGACCTTCTGACACTGTAGTGGAGATTATGGTTTCAATTGGATTGGAAGTTACCGCAACCACTATGTCTG
    K  S  S  S  K  P  F  Q  I  K  L  E  D  C  D  I  T  S  N  T  K  V  N  V  S  F  N  G  V  G  D  T  D>
                              LPFA                                                                 >

810       820       830       840       850       860       870       880       890       900
GATGCGACACTGGTTTCTGTTAACACTGAAGCAGGTGCGGCAACTGGCGTGGGCATCGGTATCTACGACAACGCTAACAAGCTTGTTGAAATGAACACCG
CTACGCTGTGACCAAAGACAATTGTGACTTCGTCCACGCCGTTGACCGCACCGTAGCCATAGATGCTGTTGCGATTGTTCGAACAACTTTACTTGTGGC
    D  A  T  L  V  S  V  N  T  E  A  G  A  A  T  G  V  G  I  G  I  Y  D  N  A  N  K  L  V  E  M  N  T>
                              LPFA                                                                 >

910       920       930       940       950       960       970       980       990      1000
GTAAATCCACCACTACGTTGGCTGCTGGTCAGACCGTGCTGTACTACACGGCTAACTACGTTGCAACAAAAGATACTGTAACCACTGGTTACGGTAACGC
CATTTAGGTGGTGATGCAACCGACGACCAGTCTGGCACGACATGATGTGGCGATTGATGCAACGTTGTTTTCTATGACATTGGTGACCAATGCCATTGCG
 G  K  S  T  T  T  L  A  A  G  Q  T  V  L  Y  Y  T  A  N  Y  V  A  T  K  D  T  V  T  T  G  Y  G  N  A>
                              LPFA                                                                 >

1010      1020      1030      1040      1050      1060      1070      1080      1090      1100
AGAAGTGGACTTCAACCTGTCCTACGAATAATGGAATTTTCGTTAATACAGAGAATCATAATGGCAACGGAAATCCCGTTGCCATTTTTTCCAGCGGAGG
TCTTCACCTGAAGTTGGACAGGATGCTTATTAGCTTAAAAGCAATTATGTCTGTTAGTATTACCGTTGCCTTTAGGGCAACGGTAAAAAAGGTCGCCTCC
 E  V  D  F  N  L  S  Y  E  *>
       LPFA                 >

1110      1120      1130      1140      1150      1160      1170      1180      1190      1200
GTCAGGAAGAGAATCATGAACCGGCTCACGTTTGATATCTTGGCACAGCACTGGTGCTGGGCGTTGATTGCTCAAAACAGTTTTGCCGGAGGCGTGGCATTAA
GAGTCCTTCTCTTAGTACTTGGGGAGTGCAAACTATAGAACGGTGTCGTGACCACGACCGCAACTAACGGAGTTTTGTCAAAAGGGGCTCCGCACCGTAATT
         M  N  R  S  R  L  I  S  G  T  A  L  V  L  A  L  I  A  Q  N  S  F  A  G  G  V  A  L>
                              LPFB                                                         /
```

Figure 7B

```
         1210      1220      1230      1240      1250      1260      1270      1280      1290      1300
     GCAGCACGCGTGTTATTTATGACGGTAGTAGAAAGGAAGCTTCTCTTACGGTAAATAATAAAAGCACCACGGATGAATTTCTCATTCAGTCATGGATTGA
     CGTCGTGCGCACAATAAATACTGCCATCATCTTTCCTTCGAAGAGAATGCCATTTTATTATTTTCGTGGTGCCTACTTAAAGAGTAAGTCAGTACCTAACT
       S  S  T  R  V  I  Y  D  G  S  R  K  E  A  S  L  T  V  N  N  K  S  T  T  D  E  F  L  I  G  S  W  I  D>
                                                    LPFB                                                    >

1310      1320      1330      1340      1350      1360      1370      1380      1390      1400
     TGATGCTAACGGTAATAAAAGACGCCCTTTATCATCACTCCACCGTTATTTAAATTAAGGCCGACTAAAAATAACGTTTTACGTATTGTTAATACGACG
     ACTACGATTGCCATTATTTTTCTGCGGGAAATAGTAGTGAGGTGGCAATAAATTTAATTCGGGGCTGATTTTTATTGCAAAATGCATAACAATTATGCTGC
       D  A  N  G  N  K  K  T  P  F  I  I  T  P  P  L  F  K  L  S  P  T  K  N  N  V  L  R  I  V  N  T  T>
                                                    LPFB                                                    >

1410      1420      1430      1440      1450      1460      1470      1480      1490      1500
     AACACGTTAGCGCAGGATCGCGAGTCCGTTTATTGGATTAACGTAAAAGCTATTCCTGCCAAAAGTGAAGAGGCGGAAGCTAAAAACGTACTGCAGATCG
     TTGTGCAATGGCGTCCTAGCGCTCAGGCAAATAACGTAATTGCATTTTCGATAAGGACGGTTTTCACTTCTGGCGCTTCGATTTTTGCATGACGTCTAGC
       N  T  L  P  Q  D  R  E  S  V  Y  W  I  N  V  K  A  I  P  A  K  S  E  D  A  E  A  K  N  V  L  Q  I>
                                                    LPFB                                                    >

1510      1520      1530      1540      1550      1560      1570      1580      1590      1600
     CCGTACGTACCCGCTTAAAACTGTTCTATCGCCCGGCGGGGCCTGAAAGGCAATAGCATGGACGGCTGGAACAAACTGCAGTTCACCAGCGCAGGGGCTAA
     GGCATGCATGGGCGAATTTTGACAAGATAGCGGGCCGCCGGACTTTCCGTTATCGTACCTGCCGACCTTGTTTGACGTCAAGTGGTCGCGTCCCCGATT
       A  V  R  T  R  L  K  L  F  Y  R  P  A  G  L  K  G  N  S  M  D  G  W  N  K  L  Q  F  T  S  A  G  A  N>
                                                    LPFB                                                    >

1610      1620      1630      1640      1650      1660      1670      1680      1690      1700
     CCAGATCAAAGTGGAAAACCCATCTGCCTTTAACCTGACGTTTAATAAATTTTATGCCAACGGCCGTGATATTGAAAAAACGGGAATGGTTCCGGCAAAA
     GGTCTAGTTTCACCTTTTGGGTAGACGGAAATTGGACTGCAAATTATTTAAAATACGGTTGCCGGCACTATAACTTTTTTGCCCTTACCAAGGCCGTTTT
       G  I  K  V  E  N  P  S  A  F  N  L  T  F  N  K  F  Y  A  N  G  R  D  I  E  K  T  G  M  V  P  A  K>
                                                    LPFB                                                    >

1710      1720      1730      1740      1750      1760      1770      1780      1790      1800
     GGCTCATTGAATATTGAACTGCCAGCCGGCACCGGCAAGGTAAGCGAAGTTAAATACAACATTATTAATGACTTTGGCACTGCTGGCGACATGTTGACAC
     CCGAGTAACTTATAACTTGACGGTCGGCCGTGCCCGTTCCATTCGCTTCAATTTATGTTGTAATAATTACTGAAACCGTGACGACCGCTGTACAACTGTG
       G  S  L  N  I  E  L  P  A  G  T  G  K  V  S  E  V  K  Y  N  I  I  N  D  F  G  T  A  G  D  M  L  T>
                                                    LPFB                                                    >

1810      1820      1830      1840      1850      1860      1870      1880      1890      1900
     AGGCGCGTTAACTAACACGTTTTAAAGGATTATTACTATGACATGGACGCATCTTCCTCTGGGCAATAAGACCTCGCGTTTCACGCAGTCTGCGCTTGCGC
     TCCGCGCAATTGATTGTGCAAAATTTCCTAATAATGATACTGTACCTGCGTAGAAGGAGACCCGTTATTCTGGAGCGCAAAGTGCGTCAGACGCGAACGCG
       Q  R  V  N  *>
                       >
                                       M  T  W  T  H  L  P  L  G  N  K  T  S  R  F  T  Q  S  A  L  A>
                                                    LPFC                                                    >

1910      1920      1930      1940      1950      1960      1970      1980      1990      2000
     TGATGATAGCGGGTAGGCTCCCCGCGTATGCGGGAACATTTAACCCGGCTTTCTGGAGGATGTGCCGGGTATTGATCAGCACGTTGACCTTTCAATGTA
     ACTACTATCGCCCATGCGAGGGGCGCATAGCGCCTTGTAAATTGGGCCGCGAAAGACCTCCTACACGGCCCATAACTAGTCGTGCAACTGGAAAGTTACAT
       L  M  I  A  G  T  L  P  A  Y  A  G  T  F  N  P  R  F  L  E  D  V  P  G  I  D  Q  H  V  D  L  S  M  Y>
                                                    LPFC                                                    >

2010      2020      2030      2040      2050      2060      2070      2080      2090      2100
     TGAATCCAATAAAGCTGAACACGGTGCCAGGTAAATACCGGGTGTCGGTGGTGGTCAACGAAAAAAAAATGGAGTCTCGCACGGCTGGAGTTTAAGGCAGCG
     ACTTAGGTTATTTCGACTTGTGGACGGTCCATTTATGGCGCAGAGCCACCACCAGTTGCTTTTTTTTTACCTCAGAGCGTGGGACGTCAAATTCCGTCGC
       E  S  N  K  A  E  H  L  P  G  K  Y  R  V  S  V  V  V  N  E  K  K  M  E  S  R  T  L  E  F  K  A  A>
                                                    LPFC                                                    >

2110      2120      2130      2140      2150      2160      2170      2180      2190      2200
     ACAGAGGCCGAGCGCGCAAAAATGGGTGAATCGGTGGTCCGTGCTTAAGTCGGGTGCAGCTTGAAGATATGGGCGTGCGTATTGATAGCTTCCCGGCGC
     TGTCTCCGGCTCGCGCGTTTTTACCCACTTAGGGACCACGGCACGAATTCAGCGCACGTCGAACTTCTATACCCGCACGCATAACTATCGAAGGGCCGCG
       T  E  A  Q  R  A  K  M  G  E  S  L  V  P  C  L  S  R  V  Q  L  E  D  M  G  V  R  I  D  S  F  P  A>
                                                    LPFC                                                    >
```

Figure 7C

```
        2210      2220      2230      2240      2250      2260      2270      2280      2290      2300
TGAAAATGGCCCCGCCTGAAGCCTGTGTTGCTTTTGACGACATTATTCCCCAGGCGCGCCAGCCATTTCGACTTTGCAGACCAGACCCTGATCATGAGCTT
ACTTTTACCGGGGCGGACTTCGGACACAACGAAAACTGCTGTAATAAGGGGTCCGGCGGTCGGTAAAGCTGAAACGTCTGGTCTGGGACTAGTACTCGAA
 L  K  M  A  P  P  E  A  C  V  A  F  D  D  I  I  P  Q  A  A  S  H  F  D  F  A  D  Q  T  L  I  M  S  F>
                                                          LPFC                                         >

2310      2320      2330      2340      2350      2360      2370      2380      2390      2400
CCCGCAGGCTGCCGATGAAGCAGACAGCGCGCGGTACGGTGCCAGAATCGCAGTGGGACGAAGGGGTGAATGCCCTGCTGGTGGATTATAACTTTTCCGGC
GGGCGTCCGACGCTACTTGGTCTGTCGCGCGCCATGCCAGGGTCTTAGCGTCACCCTGCTTCCCCACTTACGGGACGACCACCTAATATTGAAAAGGCCG
 P  Q  A  A  M  K  Q  T  A  R  G  T  V  P  E  S  Q  W  D  E  G  V  N  A  L  L  V  D  Y  N  F  S  G>
                                                          LPFC                                         >

2410      2420      2430      2440      2450      2460      2470      2480      2490      2500
AGCAACGCCAGCTATGACGCACACGACAGTGAAACCAGCTACAACAGCGACAGGTACTATCTGAATCTGCGGCAGCGGTATGAACCTGGGGGGATGGCGGT
TCGTTGCGGTCGATACTGCGTGTGCTGTCACTTTGGTCGATGTTGTCGCTGTCGATGATAGACTTAGACGGGTCGCCATACTTGGACCCCGCTACCGCCA
 S  N  A  S  Y  D  A  H  D  S  E  T  S  Y  N  S  D  S  Y  Y  L  N  L  R  S  G  M  N  L  G  A  W  R>
                                                          LPFC                                         >

2510      2520      2530      2540      2550      2560      2570      2580      2590      2600
TACGGTAACTATAGCACCTGGACGCGAAACGACGGTAACAACACATGGGATAACATTGGCACATCCTTAAGCCGTGCCATTGTACCGGCTGAAATCACAGCT
ATGCCATTGATATCGTGGACCTGCGCTTTGCTGCCATTGTTGTGTACCCTATTGTAACCGTGTAGGAATTCGGCACGGTAACATGGCGACTTTAGTGTCGA
 L  R  N  Y  S  T  W  T  R  N  D  G  N  N  T  W  D  N  I  G  T  S  L  S  R  A  I  V  P  L  K  S  G  L>
                                                          LPFC                                         >

2610      2620      2630      2640      2650      2660      2670      2680      2690      2700
GACGTTGGGGGATACCTGCACTGCCGGTGATATTTTTGACAGCGTTCAGATGCGCGGTGTGCAGTTAACTTCCGACGAAGAGATGCTGCCTGACAGCCAG
CTGCAACCCCGTATGGAGGTGACGGCCACTATAAAAACTGTCGCAAGTCTACGCGCCACACGTCAATTGAAGGCTGCTTCTCTACGACGGACTGTCGGTC
 T  L  G  D  T  S  A  G  D  I  F  D  S  V  G  M  R  G  V  Q  L  T  S  D  E  E  M  L  P  D  S  Q>
                                                          LPFC                                         >

2710      2720      2730      2740      2750      2760      2770      2780      2790      2800
CGCGGGTTTGCGCCCGTCATCCGGGGTATTGCCAAAAGTAACGCCGAAGTTACCGTTGAGCAGAACAACTACGTTATTTACCGTACGTTTGTTCAGCCGG
GCGCCCAAACGCGGGCAGTAGGCCCCATAACGGTTTTCATTGCGGCTTCAATGGCAACTCGTCTTGTTGATGCAATAAATGGCATGCAAACAAGTCGGCC
 R  G  F  A  P  V  I  R  G  I  A  K  S  N  A  E  V  T  V  E  Q  N  N  Y  V  I  Y  R  T  F  V  Q  P>
                                                          LPFC                                         >

2810      2820      2830      2840      2850      2860      2870      2880      2890      2900
GTGCGTTTGAAATTAACGACCTGTATCCAACCTCAAACAGCGGGGACCTGACGGTCACCATTAAAGAATCGGACGGCAGTGAGCAGAAGTTCGTTCAGCC
CACGCAAACTTTAATTGCTGGACATAGGTTGGAGTTTGTCGCCGCTGGACTGCCAGTGGTAATTTCTTAGCCTGCCGTCACTCGTCTTCAAGCAAGTCGG
 G  A  F  E  I  N  D  L  Y  P  T  S  N  S  G  D  L  T  V  T  I  K  E  S  D  G  S  E  Q  K  F  V  Q  P>
                                                          LPFC                                         >

2910      2920      2930      2940      2950      2960      2970      2980      2990      3000
GTTCTCCTCGGTGGCGCTCCTCAGCGTGAAGGCCATCTCAAATACAGCCTTTCGGCCGGGGAATACCGTGCCGGGAACTATAACAGCGCCGAGCCGAAA
CAAGAGGAGCCACCGCGAGGAGGTCGCACTTCGGGTAGAGTTTATGTCGGAAAGGCGGCCCCTTATGGCACGGGCCCTTGATATTGTCGCGGCTCGGCTTT
 F  S  S  V  A  L  L  Q  R  E  G  H  L  K  Y  S  L  S  A  G  E  Y  R  A  G  N  Y  N  S  A  E  P  K>
                                                          LPFC                                         >

3010      3020      3030      3040      3050      3060      3070      3080      3090      3100
TTCGGGCAGCTTGATGCCATGTACGGGCTGCCGTATGGCTTTACGGTTGGTGCGATCTTCTCTGACGACTATTACTCGCTGGCGGGAGGATTAG
AAGCCCGTCGAACTACCGGTACATGCCCGACGGCATACCGAAATGGCAAATGCCACCACGCTAGAAGAGACTGCTGATAATGAGCGACCGCCCTCCTAATC
 F  G  Q  L  D  A  M  Y  G  L  P  Y  G  F  T  V  Y  G  A  I  F  S  D  D  Y  Y  S  L  A  G  G  L>
                                                          LPFC                                         >

3110      3120      3130      3140      3150      3160      3170      3180      3190      3200
GTAAAAACTTCGGTTATATCGGCGCGATCTCCATCGATGTAACCCAGGCAAAAAGCAAGCTGGCAAATGAGGAGAATTCGGAAGGTCAGTCTTATCGTTT
CATTTTTGAAGCCAATATAGCCGCGCTAGAGGTAGCTACATTGGGTCCGTTTTTCGTTCGACCGTTTACTCCTCTTAAGCCTTCCAGTCAGAATAGCAAA
 G  K  N  F  G  Y  I  G  A  I  S  I  D  V  T  G  A  K  S  K  L  A  N  E  E  N  S  E  G  Q  S  Y  R  F>
                                                          LPFC                                         >
```

Figure 7D

```
       3210      3220      3230      3240      3250      3260      3270      3280      3290      3300
CCTCTACTCCAAGAGGTTTAACAGCGGGTACAGATTTCCGTCTGCTGGGTTACAAGTATTCGACCAGCGGCTATTACACCTTCCAGGAAGCGACGGATGTG
GGAGATGAGGTTCTGGAAATTGTCGCCATGTCTAAAGGCAGACGACCCAATGTTCATAAGCTGGTCGCCGATAATGTGGAAGGTCCTTCGCTGCCTACAC
    L  Y  S  K  S  F  N  S  G  T  D  F  R  L  L  G  Y  K  Y  S  T  S  G  Y  Y  T  F  Q  E  A  T  D  V>
                                               LPFC                                                    >

3310      3320      3330      3340      3350      3360      3370      3380      3390      3400
GGCAGCGATGCGGACAGCTCGTTATAGCCAGTACCACAAAGGTAGTCAGATTCAGGGCAACGTGAGGCAGCAACTGGGCGCCTGGGGCTCGGTCTATTTTA
CCGTCGCTACGCCTGTCGAGAATATCGGTCATGGTGTTTGCATCAGTCTAAGTCCCGTTGCACTGCGTCGTTGACCCGGGGACCCCGAGCCAGATAAAAT
    R  S  D  A  D  S  S  Y  S  Q  Y  H  K  R  S  Q  I  Q  G  N  V  T  Q  Q  L  G  A  W  G  S  V  Y  F>
                                               LPFC                                                    >

3410      3420      3430      3440      3450      3460      3470      3480      3490      3500
ACGTCACGCAGCAGGACTACTGGAACGATGAAGGTAAACAGCGCTTCGCTGAATGCCGGTTATAACGGCCGTATTGGCCGCGTGAACTACAGGGTTGCTTA
TGCAGTGCGTCGTCCTGATGACCTTGCTACTTCCATTTGTCGCAAGCGACTTAGGGCCAATATTGCCGGCATAACCGGCGCACTTGATGTCGCAACGAAT
    N  V  T  Q  Q  D  Y  W  N  D  E  G  K  Q  R  S  L  N  A  G  Y  N  G  R  I  G  R  V  N  Y  S  V  A  Y>
                                               LPFC                                                    >

3510      3520      3530      3540      3550      3560      3570      3580      3590      3600
CACCTGGACGAAAAGCCCGGAGTGGGATGAGAGCGATCGTTTACTGTCATTCTCCATGTCGATTCCACTGGGACGCGTGTGGAGTAACTACCACCTCACG
GTGGACCTGCTTTTCGGGCCTCACCCTACTCTCGCTAGCAAATGACAGTAAGAGGTACAGCTAAGGTGACCCTGCCGCACACCTCATTGATGGTGGAGTGC
    T  W  T  K  S  P  E  W  D  E  S  D  R  L  L  S  F  S  M  S  I  P  L  G  R  V  W  S  N  Y  H  L  T>
                                               LPFC                                                    >

3610      3620      3630      3640      3650      3660      3670      3680      3690      3700
ACCGATCAGCATGGCCGAACCAACCAGCAGTTAGGGGTGAGCGGCACCGCGGCTGGAAGACCCACAACCTGAACTATAGTGTGCAGGAAGGCTACGGCAGCA
TGGCTAGTCGTACCGGCTTGGTTGGTCGTCAATCCCCACTCGCCGTGGCGCGACCTTCTGGTGTTGGACTTGATATCACACGTCCTTCCGATGCCGTCGT
    T  D  Q  H  G  R  T  N  Q  Q  L  G  V  S  G  T  A  L  E  D  H  N  L  N  Y  S  V  Q  E  G  Y  G  S>
                                               LPFC                                                    >

3710      3720      3730      3740      3750      3760      3770      3780      3790      3800
ACGGCGTGGGTAACAGCGGCAGCGTGAACCTGGATTACCAGGGCGGCGTGGGTAGCGCCAGCCTGGGTTACAACTACAACCGTGACGGCCAGCAGGTGAA
TGCCGGCACCCATTGTCGCCGTCGCACTTGGACCTAATGGTCCGCCGCACCCATCGCGGTCGGACCCAATGTTGATGTTGGCACTGCCGGTCGTCCACTT
    N  G  V  G  N  S  G  S  V  N  L  D  Y  Q  G  G  V  G  S  A  S  L  G  Y  N  Y  N  R  D  G  Q  Q  V  N>
                                               LPFC                                                    >

3810      3820      3830      3840      3850      3860      3870      3880      3890      3900
GTACGGTTTGCGCGGCGGTGTGATAGCCCATAGCGAAGGTATCGACTCTTTCTCAACCGCTGGGTGAATCCATGGCCATTATCTCGGCGCCGGCGCGCGC
CATGCCAAACGCGCCGCCACACTATCGGGTATCGCTTCCATAGCTGAGAAAGAGTTGGCGACCCACTTAGGTACCGGTAATAGAGCCGCGGCCGCGCGCG
    Y  G  L  R  G  G  V  I  A  H  S  E  G  I  T  L  S  Q  P  L  G  E  S  M  A  I  I  S  A  P  G  A  R>
                                               LPFC                                                    >

3910      3920      3930      3940      3950      3960      3970      3980      3990      4000
GGCGCGCACGTGATCAACAACGGTGGTGTGGAAGTGGACTGGATGGGTAATGCGGGTCGTACCTTACCTTAGTCCGTACCGTGAAACGGAAGTCTCACTGC
CCGCGCGTGCACTAGTTGTTGCCACCACAGCTTCACCTGACCTACCCATTACGCCCAGCATGGAATGGAATGAGGCATGGCACTTTGCCTTCAGAGTGACG
    G  A  H  V  I  N  N  G  G  V  E  V  D  W  M  G  N  A  V  V  P  Y  L  T  P  Y  R  E  T  E  V  S  L>
                                               LPFC                                                    >

4010      4020      4030      4040      4050      4060      4070      4080      4090      4100
GAAGCGACAGCCTGAACAACCAGGTTGACCTGGATACCGCCTGGGTCAACGTAGTGCCGACACGGGGCGCGATTGTTCGTGCCCGGCTTCGATACCCGAGT
CTTCGCTGTCGGACTTGTTGGTCCAACTGGACCTATGGCGGACCCAGTTGCATCACGGCTGTGCGCCGCGCTAACAAGCACGGGCGAAGCTATGGGCTCA
    R  S  D  S  L  N  N  Q  V  D  L  D  T  A  S  V  N  V  V  P  T  R  G  A  I  V  R  A  R  F  D  T  R  V>
                                               LPFC                                                    >

4110      4120      4130      4140      4150      4160      4170      4180      4190      4200
GGGCTATCGTGTGCTGATGAATCTGACGCAGGGCAATGGCAAAGCGGTGCCGTTTGGTGCTACCGCCACGCTGCTGGATACCACAAAAGAGTCCAGCAGC
CCCGATAGCACACGACTACTTAGACTGCGTCCCGTTACCGTTTCGCCACGGCAAACCACGATGGCGGTGCGACGACCTATGGTGTTTCTCAGGTCGTCG
    G  Y  R  V  L  M  N  L  T  Q  A  N  G  K  A  V  P  F  G  A  T  A  T  L  L  D  T  T  K  E  S  S  S>
                                               LPFC                                                    >
```

Figure 7E

```
         4210      4220      4230      4240      4250      4260      4270      4280      4290      4300
ATTGTGGGTGAAGACGGTCAGCTTTATATCAGCGGGATGCCGGAGAAAGGTGCCCTTCAGGTGAACTGGGGTAAAGACCAGGCACAGCAATGCCGCGTGG
TAACACCCACTTCTGCCAGTCGAAATATAGTCGCCCTACGGCCTCTTTCCAGGGGAAGTCCACTTGACCCCATTTCTGGTCCGTGTCGTTACGGCGCACC
   I  V  G  E  D  G  Q  L  Y  I  S  G  M  P  E  K  G  A  L  Q  V  N  W  G  K  D  Q  A  Q  Q  C  R  V>
                                                 LPFC                                                 >

4310      4320      4330      4340      4350      4360      4370      4380      4390      4400
GGTTTACGCTGCCGGAACAAGAGGATAATACCGGCCGTGGTGATGGGCGAATGCCGTCTGCCGGGTAACAGGGAAGGAAACGATTATGTTGAAAAAGTTGATA
GCAAATGCGACGGCCTTGTTGTCCTATTATGGCCGGCACCACTACGGCTTAGGGCAGACGGGCATTGTCCCTTCCTTTGCTAATACAACTTTTTCAACTAT
   A  F  T  L  P  E  Q  Q  D  N  T  G  V  V  M  A  N  A  V  C  R  *>
                        LPFC                                      >

4410      4420      4430      4440      4450      4460      4470      4480      4490      4500
ATGTTTACGGGCCTGTTGGGCGGGTCGGTGCTGTTTTCGGGGCAGGCGCTGGGCAGCGGCAGATTTTGGACGATGTACTCCTGAAGGTGGAAGACATATCT
TACAAATGCCGGACAACCCGCCCAGCCACGACAAAAGCCCCGTCCGCGAGCGTCGCCGTCTAAAACCTGGTACATGAGGACTTCCACCTTGTGTATAGA 4510      4520      4530      4540      4550      4560      4570      4580      4590      4600
TCAGTGCCACCATAAATAAAACAGTTTCAGATACGTCAAAGAACACAACGGGTGCGACCTTCGTAGATTTCGATAGCTGGAATTTAGGTGGAACCTATGC
AGTCACGGTGGTATTTATTTTGTCAAAGTCTATGCAGTTTCTTGTGTTGCCCACGCTGGAAGCATCTAAAGCTATCGACCTTAAATCCACCTTGGATACG 4610      4620      4630      4640      4650      4660      4670      4680      4690      4700
GATGTCCTGTGAATGCCCTGATGATACCTCTCTTATAAATGACACCTTATTTAAGGCTGTGGTTCCTCTGGCCTTTGTTACGAATATAGAGAGTCGCTCC
CTACAGGACACTTACGGGACTACTATGGAGAGAATATTTACTGTGAATAAATTCCGACAGCAAGGAGACGGGAAACAATGCTTATATCTCTCAGCGAGG 4710      4720      4730      4740      4750      4760      4770      4780      4790      4800
TATTACCAGATCAATAATAATATATTGCCATTGCGAGCGATGTACTGATTTCGGGGGGACGAGGAGAATACGTTAACACACGGTAAGGTAACCTGACAAACA
ATAATGGTCTAGTTATTATTATAACGGTAACGCTCGCTACATGACTAAAGCCCCGCTGCTCCTCTTATGCAATTGTGTGGCATTCCATTGGACTGTTTGT 4810      4820      4830      4840      4850      4860      4870      4880      4890      4900
ACCGCTCTCAGTGTTCGCAAAATGCAAGTAGTAAAGATGCAATATGGACATCGGGTGGCAAAGGTCACTTATGGCTCTATATTCTCCATCCGTTTGTGGG
TGGCGAGAGTCACAAGCGTTTTACGTTCATCATTTCTACGTTATACCTGTAGGCCACGTTTCCAGTGAATAGCGAGATATAAGAGGTAGGCAAACACCC 4910      4920      4930      4940      4950      4960      4970      4980      4990      5000
TGAAAGTATTATACCTAGCACCAAAATAATGGACCTTTTTGTGACAAAGAAACCCAGTGTATATGGCAGTATACCTGCGTCGTCTGTATATATCAGTGGT
ACTTTCATAATATGGATCGTGGTTTTATTACCTGGAAAAACACTGTTTCTTTGGGTCACATATACCGTCATATGGACGCAGCAGACATATATAGTCACCA
                                 M  D  L  F  V  T  K  K  P  S  V  Y  G  S  I  P  A  S  S  V  Y  I  S  G>
                                                            LPFD                                         >

5010      5020      5030      5040      5050      5060      5070      5080      5090      5100
TCAATTACGGTACCTCAGGGCTGTGAACTCTCCAGCGGCAGCACGCTGGAAATTCCGTTTGGGGAATTTAAGGCCACTGATTTTAAAGATCGCAAAGGAC
AGTTAATGCCATGGAGTCCCGACACTTGAGAGGTCGCCGTCGTCGCAACCTTTAAGGCAAACCCCTTAAATTCCGGTGACTAAAATTTCTAGCGTTTCCTG
   S  I  T  V  P  Q  G  C  E  L  S  S  G  S  T  L  E  I  P  F  G  E  F  K  A  T  D  F  K  D  R  K  G>
                                                 LPFD                                                 >

5110      5120      5130      5140      5150      5160      5170      5180      5190      5200
AAGTTGCAAAGAACGCCACGAAATTCACCAAAGAGCTGCAGTTTAAATGCACCAATATTTCCGATGGCGTAAAGATCTTCCTGCGTATTGAGGGAATGCC
TTCAACGTTTCTTGCGGTGCTTTAAGTGGTTTCTCGACGTCAAATTTACGTGGTTATAAAGGCTACCGCATTTCTAGAAGGACGCATAACTCCCTTACGG
   Q  V  A  K  N  A  T  K  F  T  K  E  L  Q  F  K  C  T  N  I  S  D  G  V  K  I  F  L  R  I  E  G  M  P>
                                                 LPFD                                                    >

5210      5220      5230      5240      5250      5260      5270      5280      5290      5300
AAACGGCTAATGATTCGAATGGCATCGACATGGGCAACCCGGATATCGGTGCCGTCATTGAGGGGGCTAACGGTAAAATTTTGGTGCCAAATGACGCCAGT
TTTGCCGATTACTAAGCTTACGGTAGCTGTACCCGTTGGGCCTATAGCCACGGCAGTAACTCCCGCGATTGCCATTTTAAAACCACGGTTTACTGCGGTCA
   N  A  N  D  S  N  A  I  D  M  G  N  P  D  I  G  A  V  I  E  G  A  N  G  K  I  L  V  P  N  D  A  S>
                                                 LPFD                                                 /

5310      5320      5330      5340      5350      5360      5370      5380      5390      5400
GTTAATCAGGAGCTGAGCGTATCGGGTCTTGTTGACGACACGCACCGTACGGGCTCAACGACCATTTCGGGTTACCCTATCAGTACCACCGGGAAATTGC
CAATTAGTCCTCGACTCGCATAGCCCAGAACAACTGCTGTGCCGTCGCATGCCGGGAGTTGCTGGTAAAGCCGAATGGGATAGTCATGGTGGCGTTTAACG
   V  N  Q  E  L  S  V  S  G  L  V  D  D  T  H  R  T  A  S  T  T  I  S  A  Y  P  I  S  T  T  G  K  L>
                                                 LPFD                                                 >
```

Figure 7F

```
         5410      5420      5430      5440      5450      5460      5470      5480      5490      5500
CGGCCGCCGGGGATTTCGAGGGAATTGCCACCATGCGTATTGATGTGGAGTAAGCAGGATGAAAAACCTTCATGCTTTGATGCCAGCGTGTTTACTGCTT
GCCGGCGGCCCCTAAAGCTCCCTTAACGGTGGTACGCATAACTACACCTCATTCGTCCTACTTTTTGGAAGTACGAAACTACGGTCGCACAAATGACGAA
    P  A  A  G  D  F  E  G  I  A  T  M  R  I  D  V  E  *>
                                LPFD                                    >
                                                          M  K  N  L  H  A  L  M  P  A  C  L  L  L>
                                                          LPFE                                    >

5510      5520      5530      5540      5550      5560      5570      5580      5590      5600
ACCGCTTCCGCGATGGCGGCACCGTCGAATATCGGGTTCTGCTGGTGATATCCACTTTACCATTACTATTAAGGCGGCTACCTGTGAACTGGAAAACGGACA
TGGCGAAGGCGCTACCGCCGTGGCAGCTTATAGCCAAGACGACCACTATAGGTGAAATGGTAATGATAATTCCGCCGATGGACACTTGACCTTTTGCTGT
    T  A  S  A  M  A  A  P  S  N  I  G  S  A  G  D  I  H  F  T  I  T  I  K  A  A  T  C  E  L  E  N  D>
                                            LPFE                                                  >

5610      5620      5630      5640      5650      5660      5670      5680      5690      5700
GTATCGACGTCAATATGGAGACCGTGGTGCTTCAGCGCCCGGTAAAAGTGGGTAAAGAGCTGAACCAGAAAAACTTTAGCATCGGCTTAAAAGATTGCGC
CATAGCTGCAGTTATACCTCTGGCACCACGAAGTCGCGGGCCATTTTCACCCATTTCTCGACTTGGTCTTTTTGAAATCGTAGCCGAATTTTCTAACGCG
    S  I  D  V  N  M  E  T  V  V  L  G  R  P  V  K  V  G  K  E  L  N  Q  K  N  F  S  I  G  L  K  D  C  A>
                                            LPFE                                                  >

5710      5720      5730      5740      5750      5760      5770      5780      5790      5800
GTATGCCACAAAGGCCAGCGGTTACGATGGACGGTTCTCCGGACCCGACTGACCCCTCGCTTTTTGCCCTGGATAGCGGCGGCGGCGACGGGGCGTGGCGTTA
CATACGGTGTTTCCGGTCGCAATGCTACCTGCCAAGAGGCCTGGGCTGACTGGGGAGCGAAAAACGGGACCTATCGCCGCCGCGCTGCCCGCACCGCAAT
    Y  A  T  K  A  S  V  T  M  D  G  S  P  D  P  T  D  P  S  L  F  A  L  D  S  G  G  A  T  G  V  A  L>
                                            LPFE                                                  >

5810      5820      5830      5840      5850      5860      5870      5880      5890      5900
AAAATTAAAACATCTGGTGGGGAGCAACAATAGCCCTCCAGTACCGACTCTAGGCCTGTCGAACACACTGTCTGGTTTGATGGTACGAACAAGCTGAACT
TTTTAATTTTGTAGACCACCCCTCGTTGTTATCGGGAGGTCATGGCTGAGATGGGGACAGCTTGTGTGACAGACCAAACTACCATGCTTGTTCGACTTGA
    K  I  K  T  S  G  G  E  Q  Q  Y  P  S  S  T  D  S  T  P  V  E  H  T  V  W  F  D  G  T  N  K  L  N>
                                            LPFE                                                  >

5910      5920      5930      5940      5950      5960      5970      5980      5990      6000
ATATCGCCAGCTATGTGCCTGTTAAGCCGGATGCCACCGTTGGCAGAGCGAATGCGACGGTGAATTTTAGCGTCACATACGAATAATGACTGAGGGCCAG
TATAGCGGTCGATACACGGACAATTCGGCCTACGGTGGCAACCGTCGTGCGCTTACGCTGCCACTTAAAATCGCAGTCGTATGCTTATTAGTGACTCCCGGTC
    Y  I  A  S  Y  V  P  V  K  P  D  A  T  V  G  T  A  N  A  T  V  N  F  S  V  T  Y  E  *>
                                            LPFE                                                  >

6010      6020      6030      6040      6050      6060      6070      6080      6090      6100
TTCGCTGGCCCTTTTCCATTTTTAGTGATTTTTTGTAAAAATCTTCTCCGATCACACTCTCCGTTGCCACTTTCCCCTCTGCTTGTGGTCTACTTAACCG
AAGCGACCGGGAAAAGGTAAAAATCACTAAAAAACATTTTTAGAAGAGGCTAGTGTGAGAGGCAACGGTGAAAGGGGAGACGAACACCAGATGAATTGGC

6110
TGCTCTCGAGCGC
ACGAGAGCTCGCG
```

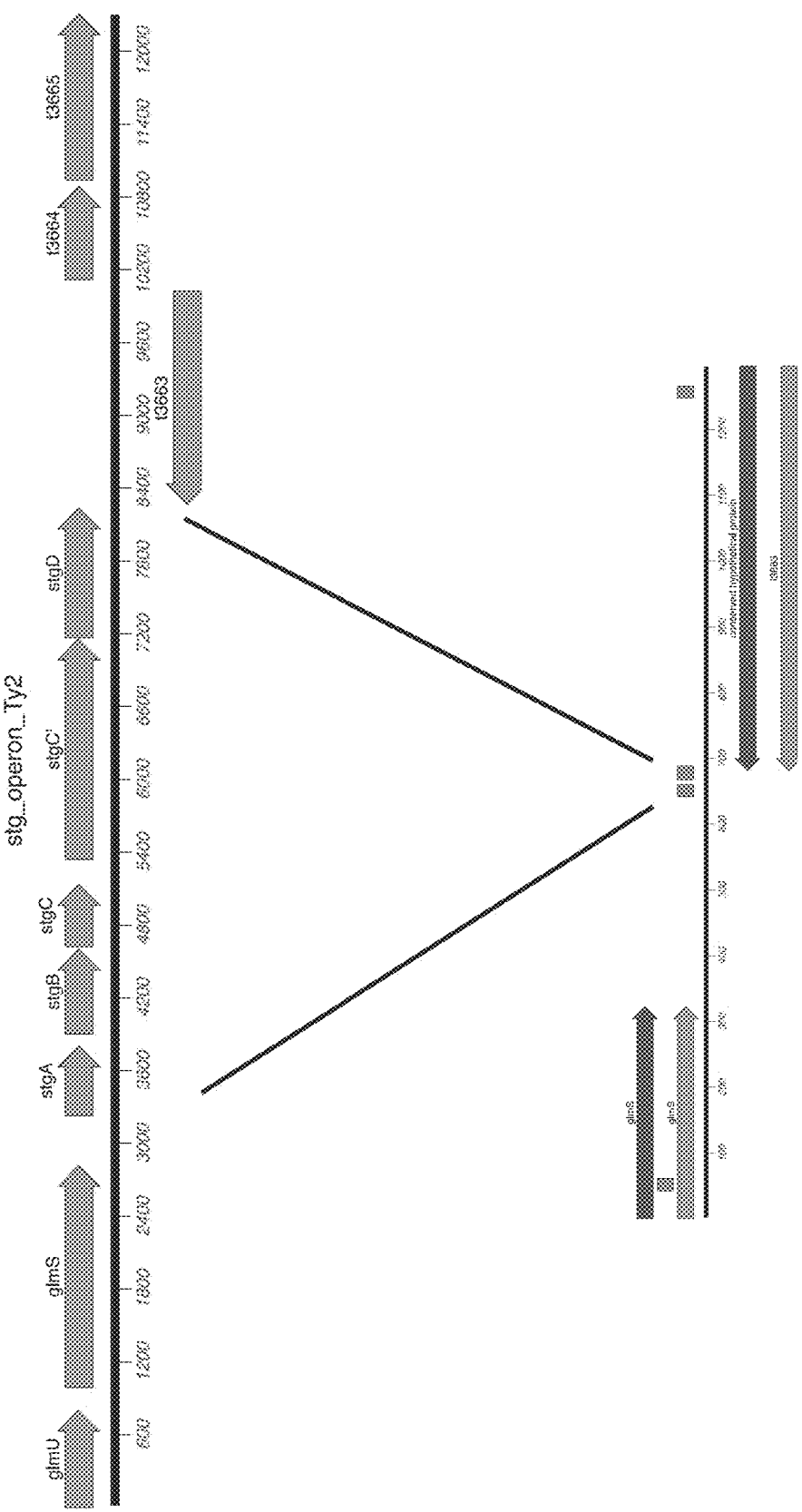

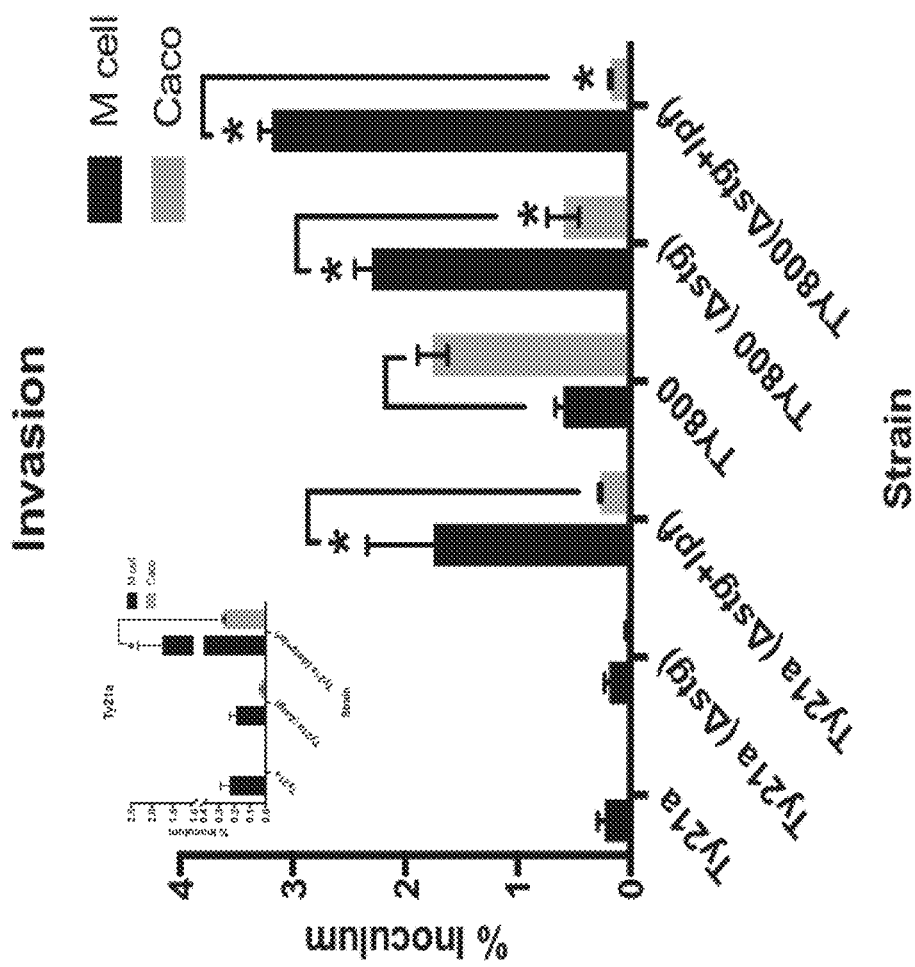
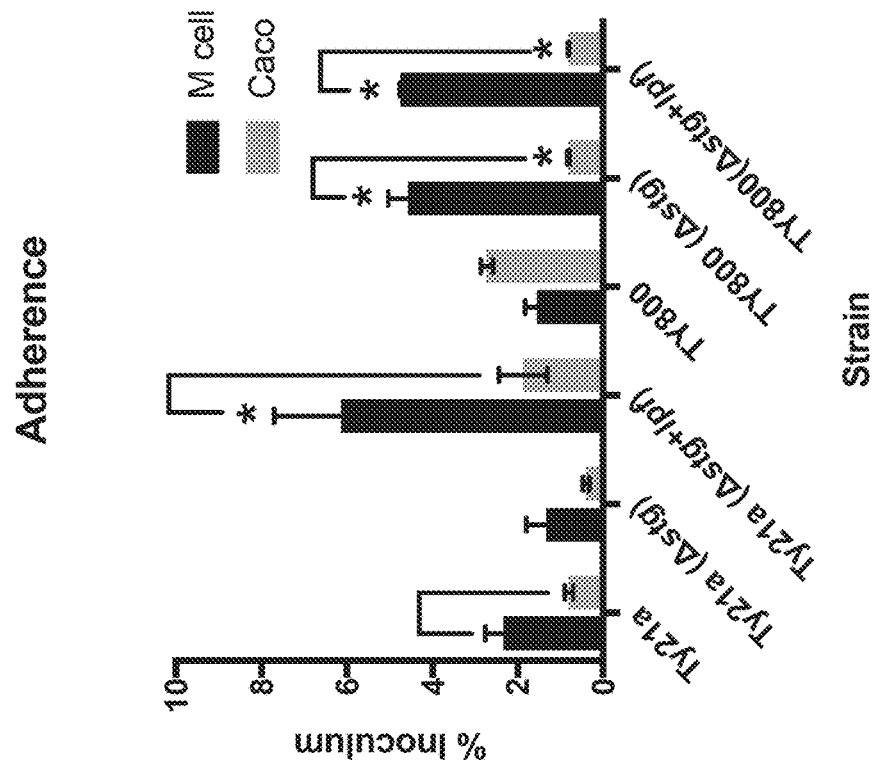
Figure 12

METHOD TO ENHANCE IMMUNOGENICITY OF LIVE TYPHOID VACCINES AND CARRIERS

PRIORITY

This application claims the benefit of U.S. Provisional Application No. 62/492,649 filed May 1, 2017. The entire content of the applications referenced above are hereby incorporated by reference.

STATEMENT REGARDING FEDERALLY SPONSORED RESEARCH

This invention was made with government support under R21 AI119697 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 30, 2018, is named 17555_048US1_SL.txt and is 94,552 bytes in size.

BACKGROUND

*Salmonella enterica* strains are responsible for 120 million illnesses and 365,000 deaths each year, worldwide. With regard to their ability to cause infection, *S. enterica* can be broadly divided into two classes, generalists, which infect a variety of animals, and host-specific, infecting only a single host. The generalists, such as *S. enterica* serovar Typhimurium and *S. enterica* serovar Enteritidis, cause gastrointestinal disease typified by a localized gut inflammation. In most cases, the disease is self-limiting in immunocompetent individuals. Generalists, such as S. Typhimurium, elicit a robust host immune response by preferentially targeting the microfold cells (M cells) present on the luminal surface of the Peyer's patches (PPs), while enterocytes are a less favorable invasion target. M cells are specialized epithelial cells that predominantly reside in the follicle-associated epithelium (FAE) overlying Peyer's patches. M cells also reside in other sections of the intestinal tract such as the colon and rectum. The ability of M cells in Peyer's patches to take up and transcytose microorganisms to antigen-presenting cells makes M cells an ideal target for vaccine delivery to the mucosal immune system.

After invasion into the PP, S. Typhimurium rapidly encounters dendritic cells (DCs) and is phagocytized. These *Salmonella*-containing DCs may interact directly with B cells within the PP, resulting in IgA switching and production of intestinal IgA. In addition, T-cell priming by the *Salmonella*-containing DCs begins in the PP and continues in the deeper immunological tissues (e.g., the spleen), resulting in activation of B cells and $CD4^+$ and $CD8^+$ T-cells, leading to production of a systemic cell-mediated and humoral immune response. S. Typhimurium stimulates a strong pro-inflammatory immune response that assists with effector cell recruitment and DC maturation. During invasion of PPs and intestinal epithelial cells, the host immune system is exposed to numerous pathogen-associated molecular patterns (PAMPs) produced by S. Typhimurium, including flagella, lipopolysaccharide (LPS) and bacterial DNA. These PAMPs are recognized by their cognate toll-like receptors (TLRs). TLR4 recognizes the lipopolysaccharide component of the *Salmonella* cell membrane and TLR5 recognizes flagellin, the primary component of *Salmonella* flagella. Binding of PAMPS to host cell TLRs results in the secretion of the chemokine interleukin 8 (IL-8), and the pro-inflammatory cytokines interleukin-1β, interleukin-6, tumor necrosis factor alpha (TNFα) and interferon gamma (IFNγ). The production of these cytokines recruits and activates neutrophils as well as monocytes and DCs. In addition, intracellular receptors such as the nucleotide-binding and oligomerization domain (NOD)-like receptor family that includes NOD1 and NOD2 recognize cell wall components of *Salmonella*. Upon sensing intracellular bacterial products, NOD1 and NOD2 associate with Rip2 to initiate a signal transduction cascade that leads to NF-κB expression and production of pro-inflammatory mediators.

The propensity for S. Typhimurium to stimulate the host immune system has resulted in the identification of a variety of attenuation strategies for developing live *Salmonella* vaccines. Attenuated *Salmonella* strains have been further modified to express genes from heterologous pathogens as vaccines against those pathogens. Many such successful *Salmonella*-vectored vaccines have been validated using an S. Typhimurium vector tested in mouse models. However, since S. Typhimurium does not disseminate past the intestinal barrier in humans, attenuated *Salmonella enterica* serovar *typhi* strains are the preferred vectors for human vaccines, as this pathogen does invade and colonize spleen, liver and other immune tissues relevant to generating a robust systemic response. While most of the attenuation strategies originally developed for S. Typhimurium also work well for *S. typhi*, the immunogenicity of *S. typhi*-vectored vaccines has been low. As a result, no live *S. typhi*-vectored vaccine has been developed for humans and the platform remains unused.

Infection by the human-specific serovar *Salmonella enterica* serotype *typhi* (*S. typhi*) does not result in a pro-inflammatory cytokine cascade, nor are large numbers of neutrophils or monocytes recruited to the infection site. Instead, production of pro-inflammatory cytokines is suppressed. Some of this immunological silence can be attributed to the actions of the immunosuppressive virulence-associated (Vi) capsular polysaccharide, which masks important TLR ligands such as lipopolysaccharide and flagella. The TviA protein, which regulates Vi production, also down-regulates flagella after cellular invasion. Further, TviA also downregulates genes encoding the type 3 secretion system located in *Salmonella* pathogenicity island 1, thereby avoiding activation of NF-kB in epithelial cells.

An additional problem in stimulating an immune response to *S. typhi* is that the invading bacteria do not target the PPs as efficiently as S. Typhimurium. While it is possible to detect *S. typhi* in the PPs shortly after inoculation, the long polar fimbriae (Lpf) responsible for M cell recognition and attachment in S. Typhimurium are not present in *S. typhi*, and in vitro studies suggest that the majority of the typhoid bacterial population preferentially associates with the intestinal epithelial cells.

Accordingly, a vaccine against *S. typhi* with enhanced immunogenicity is needed.

SUMMARY

In certain embodiments, the present invention provides a recombinant *Salmonella enterica* serovar *typhi* cell that lacks a functional stg operon (*Salmonella typhi* Δstg), and/or contains a long polar fimbriae (Lpf) of *S. enterica* serovar Typhimurium (*Salmonella typhi* Lpf⁺).

In certain embodiments, the present invention provides a recombinant attenuated derivative of a pathogenic *Salmonella enterica* serovar *typhi* cell, wherein (a) one or more genes encoding subunits of a stg operon (*Salmonella typhi* Δstg) are inactivated or deleted resulting in a decrease of the Stg adhesin/fimbriae production as compared to genes encoding a wild-type Stg operon (stgABCC'D), and/or (b) the cell comprises a nucleic acid encoding at least one of a gene encoding a subunit of a long polar fimbriae (Lpf) of *S. enterica* serovar Typhimurium protein. In certain embodiments, the modified *Salmonella* cell is a live, attenuated bacterial vaccine. As used herein, the term "attenuated" refers to any bacterial cell (e.g., an attenuated *Salmonella* cell) that has been modified so that its pathogenicity in the intended subject is substantially reduced. The bacteria may be attenuated to the point they are nonpathogenic from a clinical standpoint, i.e., that subjects exposed to the bacteria do not exhibit a statistically significant increased level of pathology relative to control subjects.

In certain embodiments, the present invention provides a live bacterial vaccine comprising the recombinant *Salmonella* cell described herein.

In certain embodiments, the present invention provides a composition comprising the recombinant *Salmonella* cell described herein and a pharmaceutically-acceptable, non-toxic vehicle.

In certain embodiments, the present invention provides a method of protecting a patient against *Salmonella enterica* serovar *typhi* colonization or infection comprising administering to the patient an effective amount of the vaccine or composition described herein.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-1F. Immunocytochemistry of Caco-2 cells without (FIG. 1A, FIG. 1B, FIG. 1C) or with (FIG. 1D, FIG. 1E, FIG. 1F) co-culture with Raji B cells comparing UEA-1 lectin binding (FIG. 1B and FIG. 1E) and galectin-9 expression (FIG. 1C and FIG. 1F). Shows decreased binding by UEA-1 and increased galectin-9 expression after co-culture. ZO-1 expression observed in both Caco-2 cells (FIG. 1A) and co-culture (FIG. 1D). M cell=co-culture, Caco-2=monoculture. Bar: 25 μm.

FIGS. 2A-2B. *S. typhi* adherence to Caco-2 and M-like cells. *Salmonella* cells were added to tissue culture wells at an MOI of 10 and allowed to incubate for 1 h. ISP1820=*S. typhi* wild type; RAZ025=ISP1820 Δstg; M cell=co-culture, Caco=monoculture, pWSK29=empty plasmid, pKR012=pWSK29 lpfABDCE, pKR022=pWSK29 stgABCC'D. (FIG. 2A) Percentage of the inoculum associated with Caco-2 or M-like cells after one hour of incubation. Adherence to M cell vs Caco-2 cells for each strain was different, P≤0.01. Significant differences are indicated by letters: a, P≤0.02 compared to M-cell adherence of ISP1820 (pWSK29); b, P≤0.0002 compared to M-cell adherence of RAZ025(pKR022); c, P<0.0001 compared to Caco-2 cell adherence by ISP1820(pWSK29); d, P<0.0001 compared to Caco-2 cell adherence by RAZ025(pKR022). Brackets indicate differences in M cell adherence, P=0.02. (FIG. 2B) *Salmonella* strains, as indicated, were added to tissue culture wells at an MOI of 100 and allowed to incubate for 1 h. Immunocytochemistry of Caco-2 cells with (rows a, b) or without (rows c, d) co-culture of Raji B cells. Slides were stained with anti-*Salmonella* CSA-1 (rows a, c) and a merge of all stains (rows b, d) with anti-*Salmonella* CSA-1 (green), anti-ZO-1 (yellow), anti-galectin-9 (red), and DAPI (blue). Bar: 25 μm FIG. 3. *Salmonella* invasion of M cell and Caco-2 cell polarized monolayers. *Salmonella* strains were added to tissue culture wells at an MOI of 10. Invasion of M cells vs Caco-2 cells was different for all strains, P≤0.01. Other differences are indicated by letters: a, P≤0.003 compared to M-cell invasion by ISP1820(pWSK29) or RAZ025 (pKR022); b, P≤0.0001 compared to Caco-2 cell invasion by ISP1820(pWSK29) or RAZ025(pKR022). The bracket indicates a significant difference in M cell invasion, P≤0.003.

FIG. 4. Basal secretion of IL-8 by polarized M cells 4 h after inoculation with *S. typhi*. ISP1820=wild type *S. typhi*, RAZ025=ISP1820 Δstg, pWSK29=empty plasmid, pKR012=pWSK29 lpfABCDE. *P=0.003 compared to ISP1820(pWSK29). **P≤0.006 compared to PMA-treated cells.

FIGS. 5A-5B. IgG titers on 7 week serum samples for StgA (A) and LpfA (B) as determined by ELISA. A. *P≤0.02 for mice inoculated with these strains vs. ISP1820(pKR012). B. *P≤0.05 for mice inoculated with these strains vs. ISP1820(pKR012).

FIG. 6. Adherence of *S. typhi* to polarized human cells. *Salmonella* cells were added to tissue culture wells at an MOI of 100. UK1=S. Typhimurium; RAZ025=ISP1820 Δstg; M cell=Caco-2 cells co-cultured with Raji B cells; Caco—monoculture of Caco-2 cells.

FIGS. 7A-7F. FIGS. 7A-7F together provide the amino acid and nucleic acid sequences for $Lpf^{+}$ (lpfABCDE). The region from 1-494 (SEQ ID NO:14) is included because the native S. Typhimurium lpf operon promoter is likely to be present in this sequence. SEQ ID NO:15 is the full-length sequence including the upstream promoter region (SEQ ID NO:14) and the coding region (SEQ ID NO:13). The nucleic acid sequences are provided for each of lpfA (SEQ ID NO: 16), lpfB (SEQ ID NO: 17), lpfC (SEQ ID NO: 18), lpfD (SEQ ID NO: 19) and lpfE (SEQ ID NO: 20). The corresponding amino acid sequences are provided for each of LPFA (SEQ ID NO: 21), LPFB (SEQ ID NO: 22), LPFC (SEQ ID NO: 23), LPFD (SEQ ID NO: 24) and LPFE (SEQ ID NO: 25).

FIG. 8. Depiction of the stg operon, which is comprised of, stgA, stgB, stgC, stgC' and stgD. Deletion of the entire stg operon is illustrated.

FIGS. 9A-9B. *S. typhi* adherence to Caco-2 and M-like cells. All *Salmonella* strains carry either empty vector pWSK29 or a derivative containing the indicated fimbrial operon. *Salmonella* cells were added to tissue culture wells at an MOI of 10. FIG. 9A. The percentage of the inoculum associated with Caco-2 or M-like cells after one hour of incubation is shown. Significant differences in adherence to M-like and Caco-2 cells for each strain are indicated by brackets, P≤0.004. Significant differences between mutant and parental strain adherence to M-like cells, #, or Caco-2 cells, *, P≤0.0133. FIG. 9B. Invasion of M-like cells vs Caco-2 cells was different for all strains except Typhimurium+lpf, P≤0.0007. The ability to invade Caco-2 cells was different from the ability to invade M-like cells for all strains except Typhimurium+lpf, P≤0.0007. Significant differences between mutant and parental strain invasion of M-like cells, #, or Caco-2 cells, *, are indicated, P<0.0001.

FIGS. 10A-10B. Invasion of Peyer's patches and epithelium in ligated ileal loops. (FIG. 10A) Loops were inoculated with a single strain. Summary results from 6-8 loops.

*P<0.001 (FIG. 10B) Competition assay in which two strains were inoculated into a single loop. Summary of results from 4 independent loops. Dose for each strain was 1×10e8 CFU.

FIG. 11. Serum IgG responses against *Salmonella* LPS in mice after a single intranasal immunization with the indicated strains. 5 BALB/c mice per group.

FIG. 12. Adherence and invasion of polarized Caco-2 cells and model M cells by *S. typhi* vaccine strains. Differences in adherence or invasion of Caco vs M cells is indicated by a bracket (P<0.001). Differences between parent vs derivative are indicated by an asterisk (P<0.001). Inset shows expanded results for Ty21a.

DETAILED DESCRIPTION

Figures 1A, 1B, 1C, 1D, 1E, 1F:
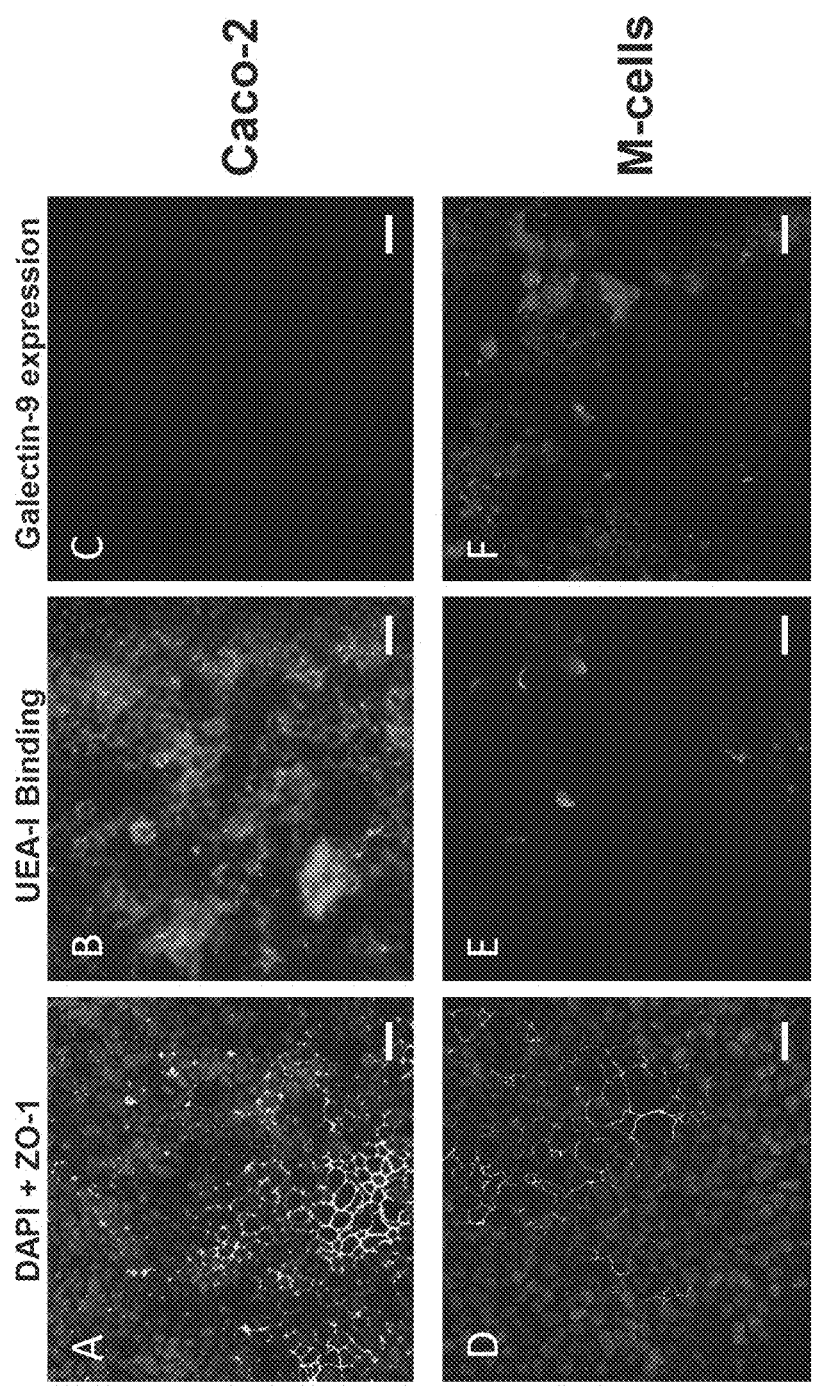

The present invention provides an improved vaccine for use to protect mammals against *Salmonella enterica* serovar *typhi* colonization or infection. In certain embodiments of this invention, a modified *Salmonella enterica* serovar *typhi* can be delivered to a mammal in a pharmacologically acceptable vehicle.

Recombinant *Salmonella*

In some embodiments, a recombinant bacterium of the invention is a species or subspecies of the *Salmonella* genera. For instance, the recombinant bacterium may be a *Salmonella enterica* serovar. In an exemplary embodiments, a bacterium of the invention may be derived from S. Typhimurium, *S. typhi*, S. Paratyphi, *S. gallinarum*, S. Enteritidis, S. Choleraesius, S. Arizona, or S. Dublin. In another exemplary embodiment, a bacterium of the invention may be an *S. typhi* bacterium. In yet another exemplary embodiment, a bacterium of the invention may be an *S. typhi* ISP1820 bacterium.

In certain embodiments, a recombinant bacterium of derived from *Salmonella* may be particularly suited for use as a vaccine. Infection of a host with a *Salmonella* strain typically leads to colonization of the gut-associated lymphoid tissue (GALT) or Peyer's patches, which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus, the use of recombinant *Salmonella* for oral immunization stimulates all three branches of the immune system, which is particularly important for immunizing against infectious disease agents that colonize on and/or invade through mucosal surfaces.

To be safe for use as a vaccine, the bacterial enteric pathogen must be attenuated for virulence by deletion or regulated expression of a virulence gene. In the case of *Salmonella*, this includes the following genes pab, aroA, aroC, aroD, asdA, dapA, dam, murA, nadA, pncB, galE, pmi, fur, ompR, htrA, hemA, cdt, cya, crp, phoP, phoQ, rfc, rfaH, poxA, galU, guaB, guaA, hfq, msbB, relA, ssaV, spoT, clpP, clpX, gidA, wecA or genes required for the function of type 3 secretion systems in pathogenicity island 2, such as ssaV, or an effector molecule secreted by the type 3 secretion system, such as sopB. The genes may be deleted or a regulatable promoter may be inserted in front of the gene to achieve regulated delayed attenuation.

In some embodiments, a recombinant bacterium of the invention is a species or subspecies of the *Salmonella* genera. For instance, the recombinant bacterium may be a *Salmonella enterica* serovar. In an exemplary embodiment, a bacterium of the invention may be derived from S. Typhimurium, *S. typhi*, S. Paratyphi, *S. gallinarum*, S. Enteritidis, S. Choleraesius, S. Arizona, or S. Dublin. In another exemplary embodiment, a bacterium of the invention may be an *S. typhi* bacterium. In another exemplary embodiment, a bacterium of the invention may be an *S. typhi* Ty2 bacterium. In yet another exemplary embodiment, a bacterium of the invention may be an *S. typhi* ISP1820 bacterium. In certain embodiments, the bacterium is Ty21a, Ty800, χ9639, χ9640, χ9633, CVD 908, CVD 908-htrA, CVD 909, Ty21a-GAD, MD77, Ty21a-PA-01, Ty21a-Ss or M01ZH09 (also called ZH9).

Inactivation of Stg Operon

Stg fimbriae are members of a class of fimbriae that utilize a chaperone/usher assembly pathway. Interaction of periplasmic chaperone/subunit complexes with the usher, an integral outer membrane protein, facilitates the release of fimbrial subunits and their secretion through the usher channel. The only *Salmonella enterica* serovar known to carry stg genes is *S. typhi*, although it is also present in *Salmonella bongori*. In some strains of *Escherichia coli*, the stg operon is comprised of four genes, stgA, stgB, stgC and stgD, with each gene encoding a protein that is presumably required for synthesis of the Stg fimbriae (Lymberopoulos, 2006, Characterization of Stg fimbriae from an avian pathogenic *Escherichia coli* O78:K80 strain and assessment of their contribution to colonization of the chicken respiratory tract, J. Bacteriol. 188: 6449-6459). The proteins have been assigned their function based on homology with other fimbrial subunits. StgA is the major fimbrial subunit protein, StgB is the chaperone, StgC is the usher, and StgD is the adhesin.

In *E. coli*, the stgC gene encodes an 840-amino acid (aa) protein. In *S. typhi*, the stgC gene has been characterized as a pseudogene due to a premature stop codon at codon 171, leading to a 170-aa protein. A second open reading frame that lies between stgC and stgD is designated stgC', and may encode a 605-aa protein (FIG. 8) (Forest et al., "*Salmonella enterica* serovar *typhi* possesses a unique repertoire of fimbrial gene sequences," Infect Immun. 2007 November; 75(11):5264-71 Epub 2007 Aug. 20; Townsend et al., "*Salmonella enterica* Serovar *typhi* Possesses a Unique Repertoire of Fimbrial Gene Sequences," Infect Immun. 2001 May; 69(5): 2894-2901). Thus, it is possible that *S. typhi* do not produce Stg fimbriae. However, the data indicate that *S. typhi* does produce an stg-encoded adhesin, although it is not clear whether or not this constitutes an Stg fimbriae since production of Stg fimbriae in *S. typhi* has not been directly demonstrated. Thus, the inventors refer to the functional product of the stg operon as Stg adhesin/fimbriae. Deletion of the entire stg operon (stgABCC'D) will result in the absence of Stg adhesin/fimbriae production. (Townsend, 2001. Infect. Immun. 69:2894-2901; Forest, 2007, Infect. Immun. 75:5264-5271)

As used herein the term "inactivation" of a target gene refers to a decrease, reduction, abrogation or attenuation in either transcription or translation of a gene resulting in a lower level of production of the encoded gene product or protein. Inactivation of a gene may be determined or inferred by comparing the in vitro analysis such as a western blot or enzyme linked immunosorbent assay (ELISA) for the levels of the gene products of the gene of interest. In certain embodiments, the inactivation of a gene results in a decrease of 10%, 20%, 30%, 40%, 50%, 60%, 70%, 80%, 90%, 95%, 99% or even 100% of the concentration of the target protein of interest in the cell. In certain embodiments, at least one of stgA, stgB, stgC, stgC, stgD in the Stg operon are mutated so as to no longer produce functional Stg adhesin/fimbriae.

Expression and/or Regulatable Cassettes

In certain embodiments, a recombinant bacterium comprises a regulatable cassette. Such a cassette usually comprises one or more regulatable promoters operably linked to the lpf operon genes. In certain embodiments, an individual promoter confers, activates or enhances expression of a single gene in the lpf operon. In certain embodiments, a promoter confers, activates or enhances expression of two, three, four or five genes in the lpf operon.

In certain embodiments, a regulatable cassette may be present in the chromosome of the recombinant bacterium, or may be present in an extrachromosomal vector. In one embodiment, a regulatable cassette may be present in the chromosome of the recombinant bacterium. Methods of chromosomally integrating a regulatable cassette are known in the art. Generally speaking, the regulatable cassette should not be integrated into a locus that disrupts colonization of the host by the recombinant bacterium, or that negatively impacts the use of the bacterium to evoke an immune response, such as in a vaccine.

In another embodiment, a regulatable cassette of the invention may be present in an extrachromosomal vector. As used herein, "vector" refers to an autonomously replicating nucleic acid unit. The present invention can be practiced with any known type of vector, including viral, cosmid, phasmid, and plasmid vectors. In certain embodiments the type of vector is a plasmid vector.

Promoters and Expression Cassettes

In certain embodiments, the genes of the lpf operon are operably linked to a promoter forming an expression cassette in order to be expressed.

The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function.

In certain embodiments, the promoter is a native promoter. In certain embodiments, the promoter is a regulatable promoter, a number of which are well-known in the art. As used herein, the term "promoter" may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system, which has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$.

Other enteric bacteria contain arabinose regulatory systems homologous to the araC-araBAD system from *E. coli*. For example, there is homology at the amino acid sequence level between the *E. coli* and the *S.* Typhimurium AraC proteins, and less homology at the DNA level. However, there is high specificity in the activity of the AraC proteins. For example, the *E. coli* AraC protein activates only *E. coli* $P_{BAD}$ (in the presence of arabinose) and not *S.* Typhimurium $P_{BAD}$. Thus, an arabinose regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In other embodiments, the promoter may be responsive to the level of maltose in the environment. Generally speaking, maltose may be present during the in vitro growth of a bacterium, while typically absent from host tissue. The malT nucleic acid sequence encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced by the addition of maltose. Unlike the araC-$P_{BAD}$ system, malT is expressed from a promoter (PT) functionally unconnected to the other mal promoters. PT is not regulated by MalT. The malEFG-malKBM promoter is a bidirectional promoter controlling expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by the malT nucleic acid sequence product, is referred to herein as $P_{KBM}$, and the portion of the malEFG-malKBM promoter that mediates expression of the malEFG nucleic acid sequence, and that is controlled by the malT nucleic acid sequence product, is referred to herein as $P_{EFG}$. Full induction of $P_{KBM}$ requires the presence of the MalT binding sites of $P_{EFG}$. For use in the vectors and systems described herein, a cassette with the malT nucleic acid sequence and one of the mal promoters may be used. This cassette is referred to herein as malT-$P_{mal}$. In the presence of maltose, the MalT protein is a positive regulatory element that allows expression from $P_{mal}$.

In still other embodiments, the promoter may be sensitive to the level of rhamnose in the environment. Analogous to the araC-$P_{BAD}$ system described above, the rhaRS-$P_{rhaB}$ activator-promoter system is tightly regulated by rhamnose. Expression from the rhamnose promoter ($P_{rha}$) is induced to high levels by the addition of rhamnose, which is common in bacteria but rarely found in host tissues. The nucleic acid sequences rhaBAD are organized in one operon that is controlled by the $P_{rhaBAD}$ promoter. This promoter is regulated by two activators, RhaS and RhaR, and the corresponding nucleic acid sequences belong to two transcription units that are located in the opposite direction of the rhaBAD nucleic acid sequences. If L-rhamnose is available, RhaR binds to the $P_{rhaRS}$ promoter and activates the production of RhaR and RhaS. RhaS together with L-rhamnose in turn binds to the $P_{rhaBAD}$ and the $P_{rhaT}$ promoter and activates the transcription of the structural nucleic acid sequences. Full induction of rhaBAD transcription also requires binding of the Crp-cAMP complex, which is a key regulator of catabolite repression.

Generally speaking, the concentration of rhamnose necessary to induce expression is typically less than about 2%. In some embodiments, the concentration is less than about 1.5%, 1%, 0.5%, 0.2%, 0.1%, or 0.05%. In other embodiments, the concentration is about 0.6%, about 0.5%, about 0.4%, about 0.3%, about 0.2%, or about 0.1%. In an exemplary embodiment, the concentration is about 0.1%. In another exemplary embodiment, the concentration is about 0.4%

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC $P_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the $P_{rhaBAD}$ promoter. In some embodiments, the rhaRS-$P_{rhaB}$ activator-promoter cassette from an E. coli K-12 strain may be used.

In still other embodiments, the promoter may be sensitive to the level of xylose in the environment. The xylR-$P_{xylA}$ system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-$P_{BAD}$ system described above, the xylR-$P_{xylAB}$ and/or xylR-$P_{x-ylFGH}$ regulatory systems may be used in the present invention. In these embodiments, xylR $P_{xylAB}$ xylose interacting with the XylR protein activates transcription of nucleic acid sequences operably-linked to either of the two $P_{xyl}$ promoters.

The nucleic acid sequences of the promoters detailed herein are known in the art, and methods of operably-linking them to a nucleic acid sequence encoding an arginine decarboxylase and a nucleic acid encoding an arginine agmatine antiporter are known in the art and detailed in the examples.

Nucleic Acid Sequence Encoding a Long Polar Fimbriae (Lpf)

The lpf operon consists of five genes, lpfABCDE, where lpfA encodes a fimbrial subunit, lpfB encodes the chaperone, lpfC encodes the usher, lpfD encodes the adhesin and lpfE encodes a minor subunit protein.

In certain embodiments, the present invention comprises one or more lpf operon genes, such as in a regulatable cassette. Lpf fimbriae are members of a class of fimbriae that utilize a chaperone/usher assembly pathway. Lpf fimbriae are produced by S. Typhimurium and are important for attachment and invasion of Peyer's patches in mice. Similar fimbriae are produced in some strains of Escherichia coli. The lpf operon comprises five genes, lpfABCDE, where lpfA encodes a fimbrial subunit, lpfB encodes the chaperone, lpfC encodes the usher, lpfD encodes the adhesin and lpfE encodes a minor subunit protein (FIGS. 7A-7F). In certain embodiments, all five genes of the lpf operon are present. In certain embodiments, four genes of the lpf operon are present (i.e., lpfE is not present).

In certain embodiments, the lpf operon and/or expression cassette comprising the lpf operon, is introduced on a plasmid or by insertion of the operon into the Salmonella typhi chromosome. If on a plasmid, the plasmid that does not encode an antibiotic resistance marker. There are plasmids known in the art that do not rely on antibiotic resistance for plasmid maintenance. In certain embodiments, the plasmid system is the Asd-balanced lethal system.

In certain embodiments, the lpf operon is inserted into the chromosome. In certain embodiments, the lpf operon is inserted at the spot where an attenuating deletion is made. In certain embodiments, phoP is deleted, and the lpf operon is inserted where phoP used to be. In certain embodiments, stg is deleted, and the lpf operon is inserted where stg used to be. In certain embodiments, the lpf operon is inserted into the cysG gene. The chromosomal location of a gene can influence its level of expression independently of the promoter, so the chromosomal location should provide adequate expression to allow functional Lpf fimbriae to be produced on the surface of the *S. typhi* vaccine strain.

In certain embodiments, the method the recombinant bacteria of the present invention are further modified in order to increase the resistance of the attenuated *S. typhi* vaccines to low pH (acid) to aid in its survival as it passes through the stomach of vaccines, using the method described in U.S. Pat. No. 9,580,718, which is incorporated by reference in its entirety herein.

In certain embodiments, one or more genes encoding subunits of the Lpf is operably linked to a regulatable promoter. In certain embodiments, the regulatable promoter is induced by a sugar. In certain embodiments, the sugar is selected from the group consisting of arabinose and rhamnose.

Transcription Termination Sequence

In some embodiments, the expression or regulatable cassette further comprises a transcription termination sequence. A transcription termination sequence may be included to prevent inappropriate expression of nucleic acid sequences adjacent to the cassette.

Other Mutations

In certain embodiments, a bacterium of the invention may comprise one or more mutations desirable in a bacterium used to evoke an immune response, such as in a vaccine. In particular, a bacterium may comprise one or more mutations to increase invasiveness, one or more mutations to allow endosomal escape, one or more mutations to reduce bacterium-induced host programmed cell death, one or more mutations to induce lysis of the bacterium, one or more mutations to express a nucleic acid encoding an antigen, one or more mutations to attenuate the bacterium, and/or other mutations to enhance the performance of the bacterium as a vaccine.

Vaccine Compositions and Administration

In certain embodiments, a vaccine composition comprising a recombinant bacterium of the invention may optionally comprise one or more possible additives, such as carriers, preservatives, stabilizers, adjuvants, and other substances.

In exemplary embodiments of the present invention, the recombinant bacterium is a *Salmonella typhi* bacterium adapted for use as a live attenuated vaccine. To immunize a patient, the modified *Salmonella enterica* serovar *typhi* cell is administered to the patient. In order to stimulate a preferred response of the GALT, NALT or BALT cells, in certain embodiments, the vaccine composition is administered directly into the gut, nasopharynx, or bronchus, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible.

Vaccine formulations contain an effective amount of the modified cells in a vehicle, carrier or excipient. The effective amount is sufficient to prevent, ameliorate or reduce the incidence of *S. typhi* colonization in the patient. The dosages of a vaccine composition of the invention can vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration are about $1\times10^7$ to $1\times10^{10}$ CFU depending upon the age of the host to be immunized. Administering multiple dosages may also be used as needed to provide the desired level of protective immunity. In certain embodiments, a dose of about $1\times10^7$ CFU to about $1\times10^{10}$ CFU is administered in order to achieve protective immunity. In certain embodiments about $1\times10^7$ CFU is administered. In certain embodiments about $1\times10^8$ CFU is administered. In certain embodiments about $1\times10^9$ CFU is administered. In certain embodiments, a dose of $2\times10^9$ CFU to $6.8\times10^9$ CFU is administered. The effective amount is readily determined by one skilled in the art.

The modified cells may typically range from about 1% to about 95% (w/w) of the composition, or even higher or lower if appropriate. The quantity to be administered depends upon factors such as the age, weight and physical condition of the patient considered for vaccination. The quantity also depends upon the capacity of the patient's immune system to synthesize antibodies, and the degree of protection desired. Effective dosages can be readily established by one of ordinary skill in the art through routine trials establishing dose response curves. The subject is immunized by administration of the vaccine in one or more doses. Multiple doses may be administered as is required to maintain a state of immunity to *S. typhi*.

In certain embodiments, to prepare a vaccine, the modified *S. typhi* cells are isolated, purified, lyophilized, stabilized, and/or lysed. The amount of modified *S. typhi* cells is then be adjusted to an appropriate concentration and packaged for use.

In another embodiment, the vaccine may comprise a pharmaceutical carrier (or excipient) used to resuspend the lyophilized *Salmonella typhi* vaccine. Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the vaccine is preferably presented in the form of an aerosol.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the vaccine formulation against a variety of conditions, such as temperature variations or a freeze-drying process.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

In certain embodiments, the modified *S. typhi* cells of the invention are formulated as pharmaceutical compositions and administered to a human patient in a variety of forms adapted to the chosen route of administration, i.e., orally, intranasally, intradermally or parenterally, by intravenous, intramuscular or subcutaneous routes. Accordingly, these compositions are preferably combined with pharmaceutically acceptable vehicles such as saline, Ringer's solution, dextrose solution, and the like.

Thus, in certain embodiments, the present pharmaceutical compositions are systemically administered, e.g., orally, in combination with a pharmaceutically acceptable vehicle such as an inert diluent or an assimilable edible carrier. In certain embodiments, they are enclosed in hard or soft shell gelatin capsules, are coated with an enteric coating are compressed into tablets, are formulated into dissolvable wafers or are incorporated directly with the food of the patient's diet. In certain embodiments, for oral therapeutic administration, the active compound is combined with one or more excipients and used in the form of ingestible tablets, buccal tablets, troches, capsules, elixirs, suspensions, syrups, wafers, and the like. In certain embodiments, such compositions and preparations contain at least 0.1% of modified *S. typhi* cells. The percentage of the compositions and preparations may, of course, be varied and may conveniently be between about 2 to about 60% of the weight of a given unit dosage form. The amount of modified *S. typhi* cells in such therapeutically useful compositions is such that an effective dosage level will be obtained.

In an exemplary embodiment, the recombinant bacterium may be administered orally. Oral administration of a composition comprising a recombinant bacterium allows for greater ease in disseminating vaccine compositions for infectious agents to a large number of people in need thereof, for example, in Third World countries or during times of biological warfare. In addition, oral administration allows for attachment of the bacterium to, and invasion of, the gut-associated lymphoid tissues (GALT or Peyer's patches) and/or effective colonization of the mesenteric lymph nodes, liver, and spleen. This route of administration thus enhances the induction of mucosal immune responses as well as systemic and cellular immune responses.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Intranasal formulations may include vehicles that neither cause irritation to the nasal mucosa nor significantly disturb ciliary function. Diluents such as water, aqueous saline or other known substances can be employed with certain embodiments of the subject invention. The nasal formulations may also contain preservatives such as, but not limited to, chlorobutanol and benzalkonium chloride. A surfactant may be present to enhance absorption of the subject proteins by the nasal mucosa.

In certain embodiments, the modified *S. typhi* cells may also be administered by infusion or injection. Solutions of the modified *S. typhi* cells may be prepared in water, optionally mixed with a nontoxic surfactant. Dispersions can also be prepared in glycerol, liquid polyethylene glycols, triacetin, and mixtures thereof and in oils.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the modified *S. typhi* cells in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages and/or safety of the pharmaceutical compositions of the present invention can be determined by comparing their in vitro activity, and in vivo activity in animal models.

Kits

In certain embodiments, the invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, such as orally.

Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to physicians and other skilled practitioners. For instance, assays such as ELISA, and ELISPOT may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, the invention provides a method for eliciting an immune response against an antigen in a host. The method comprises administering to the host an effective amount of a composition comprising a recombinant bacterium of the invention.

In still another embodiment, a recombinant bacterium of the invention may be used in a method for eliciting an immune response against a pathogen in an individual in need thereof. The method comprises administrating to the host an effective amount of a composition comprising a recombinant bacterium as described herein. In a further embodiment, a recombinant bacterium described herein may be used in a method for ameliorating one or more symptoms of an infectious disease in a host in need thereof. The method comprises administering an effective amount of a composition comprising a recombinant bacterium as described herein.

In a further embodiment, the present invention encompasses a method for enhancing the immunogenicity of a live attenuated *Salmonella typhi* vaccine or *Salmonella typhi*-vectored vaccine.

EXEMPLARY EMBODIMENTS

In exemplary embodiments of the present invention, the recombinant bacterium is a *Salmonella typhi* bacterium adapted for use as a live attenuated vaccine.

In certain embodiments, the present invention provides a recombinant attenuated derivative of a pathogenic *Salmonella enterica* serovar *typhi* cell, wherein (a) one or more genes encoding subunits of a stg operon (*Salmonella typhi* Δstg) are inactivated or deleted resulting in a decrease of Stg adhesin/fimbriae production as compared to genes encoding a wild-type Stg operon (stgABCC'D), and/or (b) the cell comprises a nucleic acid encoding at least one of a gene encoding a subunit of a long polar fimbriae (Lpf) of *S. enterica* serovar Typhimurium protein.

In certain embodiments, the one or more genes encoding subunits of the stg adhesin/fimbriae are inactivated.

In certain embodiments, the one or more genes encoding subunits the lpf operon is operably linked to a regulatable promoter.

In certain embodiments, regulatable promoter is induced by a sugar. In certain embodiments, sugar is selected from the group consisting of arabinose and rhamnose.

In certain embodiments, one or more genes encoding subunits the stg operon are deleted.

In certain embodiments, at least one of stgA, stgB, stgC, stgC' stgD are inactivated or deleted.

In certain embodiments, the decrease of Stg adhesin/fimbriae production is an elimination of Stg adhesin/fimbriae production.

In certain embodiments, the subunit of Lpf is subunit A (lpfA), subunit B (lpfB), subunit C (lpfC), subunit D (lpfD), and/or subunit E (lpfE).

In certain embodiments, the cell lacks a stg operon (stgABCC'D), and contains an Lpf of *S. enterica* serovar Typhimurium (*Salmonella typhi* Δstg $Lpf^+$).

In certain embodiments the $Lpf^+$ has at least 90% identity (i.e., 90%, 91%, 92%, 93%, or 94%, or 95%, 96%, 97%, 98%, 99%, 99.1%, 99.2%, 99.3%, 99.4%, 99.5%, 99.6%, 99.7%, 99.8%, 99.9% or 100%) to SEQ ID NOS 21, 22, 23, 24, and/or 25. In certain embodiments, the $Lpf^+$ has at least 99%, 99.9% or 99.99% identity to SEQ ID NOS 21, 22, 23, 24, and/or 25. In certain embodiments, the $Lpf^+$ consists of SEQ ID NOS 21, 22, 23, 24, and/or 25.

In certain embodiments, *Salmonella* is Ty21a, Ty800, χ9639, χ9640, χ9633, CVD 908, CVD 908-htrA, CVD 909, Ty21a-GAD, MD77, Ty21a-PA-01, Ty21a-Ss or M01ZH09 (also called ZH9). In certain embodiments, the modified *Salmonella* is Ty21a.

In certain embodiments, cell further comprises one or more virulence genes encoding pab, aroA, aroC, aroD, asdA, dapA, dam, murA, nadA, pncB, galE, pmi, fur, ompR, htrA, hemA, cdt, cya, crp, phoP, phoQ, rfc, rfaH, poxA, galU, guaB, guaA, hfq, msbB, relA, spoT, clpP, clpX, gidA, wecA or genes required for type 3 secretion system function in pathogenicity island 2, and/or an effector molecule secreted by the type 3 secretion system are inactivated or deleted. In certain embodiments, the gene required for type 3 secretion system function in pathogenicity island 2 is ssaV. In certain embodiments, effector molecule secreted by the type 3 secretion system is sopB.

In certain embodiments, the one or more virulence genes are operably linked to a regulatable promoter.

In certain embodiments, the regulatable promoter is induced by a sugar. In certain embodiments, the sugar is selected from the group consisting of arabinose and rhamnose.

In certain embodiments, the present invention provides a live bacterial vaccine comprising the recombinant *Salmonella* cell described herein.

In certain embodiments, the present invention provides a composition comprising the recombinant *Salmonella* cell described herein and a pharmaceutically-acceptable, non-toxic vehicle.

In certain embodiments the pharmaceutically-acceptable, non-toxic vehicle is an enteric coated capsule or liquid suspension.

In certain embodiments, the present invention provides a method of protecting a patient against *Salmonella enterica* serovar *typhi* colonization or infection comprising administering to the patient an effective amount of the vaccine or the composition described herein.

In certain embodiments the composition is administered by intramuscular, intradermal, subcutaneous delivery, or via a mucosal surface.

In certain embodiments the composition is administered by subcutaneous or intramuscular injection.

In certain embodiments the composition is administered by oral ingestion.

The invention will now be illustrated by the following non-limiting Examples.

Example 1

Roles of Lpf and Stg Fimbriae in *Salmonella* Interactions with Enterocytes and M Cells When designing *S. typhi*-based vaccines, the goal is to achieve high immunogenicity while keeping reactogenicity low (Galen, et al., 3rd. 2014. The delicate balance in genetically engineering live vaccines. Vaccine 32:4376-4385). Attenuation strategies that result in low reactogenicity are often poorly immunogenic (Galen, et al. 2009. *Salmonella enterica* serovar *typhi* live vector vaccines finally come of age. Immunol Cell Biol 87:400-412). The inventors have been exploring approaches to enhance immunogenicity independent of the attenuation strategy. The inventors hypothesized that the inventors could improve the immunogenicity of *S. typhi* strains by enhancing their ability to attach to M cells in the Peyer's patches. As a first step in this endeavor, the inventors focused on two fimbriae, the Long Polar Fimbriae (Lpf) produced by S. Typhimurium and Stg, produced by *S. typhi*, both involved in adherence to intestinal cells. Stg is one of five fimbriae that are present in *S. typhi* but not S. Typhimurium (Parkhill, et al. 2001. Complete genome sequence of a multiple drug resistant *Salmonella enterica* serovar *typhi* CD18. Nature 413:848-852). Stg functions in *S. typhi* attachment to human epithelial cells (Berrocal, et al., 2015. stg fimbrial operon from *S. typhi* STH2370 contributes to association and cell disruption of epithelial and macrophage-like cells. Biol Res 48:34; Forest, et al., 2007. Contribution of the stg fimbrial operon of *Salmonella enterica* serovar *typhi* during interaction with human cells. Infection and immunity 75:5264-5271). *S. typhi* mutants with a deletion in stg exhibit reduced attachment to INT407 and Hep2 monolayers. Introduction of stg into an *E. coli* strain devoid of its native fimbriae enhances its ability to bind to INT407 cells, while introduction into S. Typhimurium increases its attachment to polarized HT-29 cells. Stg adhesin/fimbriae may also have a role in the interaction of *S. typhi* with macrophages, though whether it inhibits or enhances phagocytosis is unclear.

The S. Typhimurium long polar fimbriae (Lpf), not present in *S. typhi*, enhance colonization of Peyer's patches via interactions with M cells (Baumler, et al., 1996. The lpf fimbrial operon mediates adhesion of *Salmonella* typhimurium to murine Peyer's patches. Proc Natl Acad Sci USA 93:279-283). Lpf also plays a role in the early stages of biofilm formation on host epithelial cells (Ledeboer, et al. 2006. *Salmonella enterica* serovar Typhimurium requires the Lpf, Pef, and Tafi fimbriae for biofilm formation on HEp-2 tissue culture cells and chicken intestinal epithelium. Infection and immunity 74:3156-3169), which could explain its involvement in intestinal persistence (Weening, et al. 2005. The *Salmonella enterica* serotype Typhimurium lpf, bcf, stb, stc, std, and sth fimbrial operons are required for intestinal persistence in mice. Infection and immunity 73:3358-3366). Synthesis of Lpf is regulated by an on-off switch mechanism (phase variation) to avoid host immune responses (Norris, et al., 1998. Expression and transcriptional control of the *Salmonella* typhimurium lpf fimbrial operon by phase variation. Mol Microbiol 29:311-320).

In the current study, the inventors compared the adherence and invasion capabilities of *S. typhi* with or without production of Stg and/or Lpf in polarized Caco-2 cultures and in a model in which Raji B cells are co-cultured with Caco-2 cells to drive the formation of M-like cells (Gullberg, et al. 2000. Expression of specific markers and particle transport in a new human intestinal M-cell model. Biochem Biophys Res Commun 279:808-813). Our results confirm that Stg is required for adherence to epithelial cells. Our findings also show that adherence of *S. typhi* to M-like cells is significantly enhanced when the stg operon is deleted, suggesting that *S. typhi* produces an adhesion that facilitates this interaction. Finally, the inventors show that introduction of Lpf in *S. typhi* enhances invasion of M-like cells, though it does not enhance adherence.

Materials and Methods

Bacterial Strains, Growth Media and DNA Manipulations.

The bacterial strains used in this study are described in Table 1. Bacteria were routinely grown in LB broth or agar plates (Ausubel, et al. 1991. Current protocols in molecular biology, vol. 1. Greene Publishing Associates and Wiley Interscience, New York) unless otherwise indicated. Antibiotics were added to growth media when needed as follows: kanamycin, 50 µg/ml, ampicillin, 100 µg/ml and chloramphenicol, 25 µg/ml. The high fidelity Phusion polymerase (New England Biolabs, Ipswich, Mass.) was used for all cloning done by PCR.

TABLE 1

Strains and plasmids used in this study.

| Strain or plasmid | Genotype/characteristics | Source or reference |
|---|---|---|
| *Salmonella* | | |
| Ty2 | Wild type *S. Typhi*, rpoS | (60) |
| ISP1820 | Wild type *S. Typhi* | (61) |
| χ3761 | Wild type *S. Typhimurium* UK-1 | (62) |
| RAZ025 | ISP1820 Δstg-5094 | This study |
| *E. coli* | | |
| MGN026 | endA1 hsdR17 ($r_K^-$ $m_K^+$) glnV44 thi-1 recA1 gyrA relA1 Δ(lacZYA-argF)U169 λpir deoR (φ80dlac Δ(lacZ)M15) | (63) |
| MGN617 | thi-1 thr-1 leuB6 fhuA21 lacY1 glnV44 recA1 ΔasdA4 Δzhf-2::Tn10 RP4-2-Tc::Mu [λ-pir], Km$^r$ | (63) |
| M15(pREP4) | lacZM15 thi mtl; lacI expressed from pREP4 | Qiagen |
| Plasmids | | |
| pCR-BLUNT-Topo | Kan$^r$, Zeo$^r$, pUC ori | Invitrogen |
| pMEG-375 | Cm$^r$ Ap$^r$; sacRB mobRP4 oriR6K | (64) |
| pQE30 | Ap$^r$ | Qiagen |
| pWSK29 | Ap$^r$, pSC101 ori | (65) |
| pKR005 | pMEG-375 Δstg-5094 | This study |
| pKR006 | pQE30 stgA | This study |
| pKR009 | pCR-Blunt-Topo lpfABCDE | This study |
| pKR010 | pQE30 lpfA | This study |
| pKR012 | pWSK29 lpfABCDE | This study |
| pKR017 | pCR-Blunt-Topo stgABCC'D | This study |
| pKR022 | pWSK29 stgABCC'D | This study |

Construction of an *S. typhi* Strain with a Δstg Deletion.

DNA sequences upstream and downstream of the stg operon were cloned using primer pairs 3663_for/3663_rev and glmS_for/glmS_rev, respectively (Table 2).

TABLE 2

Primers used in this study.

| Primer name | DNA sequence | SEQ ID NO. |
|---|---|---|
| 3663_for | GCGGAATTCGTCATATCAATGAACTACGGC | 1 |
| 3663_rev | CGCTCTAGACTCCAGCATCTGAGTGAGG | 2 |
| glmS_rev | GCGGAATTCCGGAAGCGAATACTATCCC | 3 |
| glmS_for | CGCGGCGCGCCGATTGTGGTGGCGCCGAAC | 4 |
| stgA_for | GGATCCATGGCATCTGATGGCACCG | 5 |
| stgA_rev | GTCGACGCGAATCTTATTTTTGGTATTCG | 6 |
| lpfA-Bam_for | GGATCCGCTGAATCTGGTGACGGCAC | 7 |
| lpfA-Sal_rev | GTCGACCATGATTCTCTTCCTGAGCCTC | 8 |
| Lpf728_for | GCCGGATCCCGCAGTGATAACAGCTCTTG | 9 |
| Lpf6821_rev | GCGCTCGAGAGCACGGTTAAGTAGACCAC | 10 |
| glmS_2473_for_Eco | GAATTCGGAAGCCTATGCTGCAGGC | 11 |

TABLE 2-continued

Primers used in this study.

| Primer name | DNA sequence | SEQ ID NO. |
|---|---|---|
| 3663_8425_rev_Xho | CTCGAGGCGGAACAACTGGTCAGGG | 12 |

S. *typhi* Ty2 chromosomal DNA was used as template. The two fragments were digested with EcoRI and ligated. The resulting fragment was digested with XbaI and NotI and cloned into suicide plasmid pMEG-375 digested with the same enzymes to yield plasmid pKR005. Plasmid pKR005 was moved into *E. coli* donor strain MGN617. The resulting strain was mated with *S. typhi* ISP1820, with selection for resistance to chloramphenicol and growth in the absence of diaminopimelic acid (DAP). Transconjugants were plated onto LB plates without NaCl containing 5% sucrose (Blomfield, et al. 1991. Allelic exchange in *Escherichia coli* using the *Bacillus subtilis* sacB gene and a temperature-sensitive pSC101 replicon. Mol Microbiol 5:1447-1457). Isolates with a deletion in the stg operon were identified by PCR. One isolate was designated as RAZ025. The point of deletion and 200 bp of the surrounding upstream and downstream regions were confirmed by DNA sequence analysis. Production of Vi antigen by *S. typhi* strains was confirmed by slide agglutination and production of complete lipopolysaccharide by all *Salmonella* strains was confirmed using silver stained gels as previously described (Hitchcock, P. J., and T. M. Brown. 1983. Morphological heterogeneity among *Salmonella* lipopolysaccharide chemotypes in silver-stained polyacrylamide gels. J Bacteriol 154:269-277).

Purification of fimbrial proteins and antibody production. To produce a his-tagged StgA protein, the stgA gene was cloned by PCR using the stgA_for/stgA_rev primer pair with *S. typhi* Ty2 chromosomal DNA as the template and the high fidelity Phusion polymerase (New England Biolabs, Ipswich, Mass.). The resulting PCR fragment was digested with BamHI and SalI and ligated to plasmid pQE30 digested with the same enzymes. The resulting plasmid, pKR006 was moved into *E. coli* strain M15(pREP4). The His-tagged StgA protein was induced and purified on a nickel column according to the manufacturer's instructions (Qiagen, Valencia, Calif.). The inventors used a similar strategy to produce His-tagged LpfA. In this case, the lpfA-Bam_for/lpfA-Sal_rev primer pair was used, with S. Typhimurium χ3761 DNA as template. The resulting plasmid was designated pKR010.

Cloning of Fimbrial Operons.

The lpfABCDE genes were cloned by PCR using the primer pair Lpf728_for/Lpf6821_rev and S. Typhimurium χ3761 chromosomal DNA as template. The resulting 6,112 bp fragment was ligated to plasmid pCR-BLUNT-Topo and transformed into *E. coli* to yield plasmid pKR009. The sequence of the entire operon was confirmed by DNA sequence analysis. The lpf operon was subcloned into the low copy number plasmid pWSK29 using BamHI and XhoI to yield plasmid pKR012. Plasmid pKR012 was then moved into various *S. typhi* strains for further analysis.

The stgABCC'D operon was cloned using a similar strategy. The plasmid pair glmS_2474_for_Eco/3663_8425_for_Xho and *S. typhi* Ty2 template DNA were used. The resulting 6,313 bp fragment was then cloned into pCR-BLUNT-Topo to yield plasmid pKR017. After confirmation by DNA sequence analysis, plasmid pKR017 was digested with EcoRI and XhoI. The resulting stg fragment was then purified and ligated to pWSK29 digested with the same enzymes to yield plasmid pKR022. Plasmid pKR022 was used for complementation studies.

Immunization of Mice.

This study was approved by the Arizona State University Institutional Animal Care and Use Committee. Seven week old, female BALB/c mice (Charles River Laboratories, Wilmington, Mass., USA) were fasted without food for approximately 20 h and water for 2 h prior to oral inoculations of indicated *S. typhi* strains. Using static starter cultures, strains were grown at 37° C. statically for 18 h in LB, then pelleted and resuspended in PBS at a concentration of $5 \times 10^{10}$ CFU/ml. 3 mice/group were inoculated with 20 µl of this bacterial preparation unless otherwise indicated. The immunization schedule alternated between oral and intranasal (IN) inoculations as follows: initial dose of $1 \times 10^9$ CFU was given orally, followed by an IN boost of $1 \times 10^7$ CFU at 1 week. The final two doses were $1 \times 10^9$ CFU, given orally at 4 weeks, and IN at 5 weeks. Water and food was returned 30 min post oral inoculations. Serum was collected from mice 7 weeks after the primary immunization.

Tissue Culture.

The human colon carcinoma cell line Caco-2 and human Burkitt's lymphoma cell line Raji were obtained from the American Type Culture Collection (Manassas, Va.). Caco-2 was cultured in Dulbecco's modified Eagle's medium (DMEM) with 4.5 g/L glucose (Corning, Manassas, Va.) containing 4 mM L-glutamine, 1% sodium pyruvate, 1% non-essential amino acids (NEEA), 100 U/ml penicillin, 100 µg/ml streptomycin, 20% heat inactivated fetal calf serum. Raji cells were cultured in RPMI 1640 with L-glutamine (2 mM) (Corning, Manassas, Va.) containing 100 U/ml penicillin, 100 µg/ml streptomycin, 10% heat inactivated fetal calf serum.

M-Cell Co-Culture Model.

Caco-2 cells were maintained and grown in upper compartment of 6.5 mm, 3 µm polycarbonate Transwell® inserts (Corning, Manassas Va.), seeding $3 \times 10^5$ cells/insert. Monolayer confluency was monitored by measuring transepithelial electrical resistances (TER) using a Millicell® ERS-2 voltohmmeter (Millipore, Temecula, Calif.). Caco-2 cells were grown for 14 days on permeable supports to achieve tight and fully differentiated monolayers with a TER of ~420 $\Omega cm^2$ (52). To confirm the polarized status of the monolayers, the inventors monitored UEA-1 lectin binding sites and expression of tight junction protein ZO-1 by confocal laser scanning microscopy (CLS) (48). $5 \times 10^5$ Raji B cells were resuspended in RPMI:DMEM 1:2 and added to the basolateral chamber of 14 day old Caco-2 monolayers and co-cultures were maintained for 4 days. To confirm presence of M-like cells expression of Galectin-9 was monitored by CLS. Corresponding mono-cultures of Caco-2 cells on matched filter supports were used as controls. The integrity of the cell monolayers was measured by TER before infections were performed.

M-Cell Co-Culture Infection Assays.

On day of infection, all transwell inserts were washed out with HBSS and replaced with antibiotic free media on both sides of chamber, 45 min prior to infection.

Using static starter cultures, strains were grown at 37° C. statically for 18 h in LB, then pelleted and resuspended in PBS at a concentration of $1.5 \times 10^9$ CFU/ml. Bacterium was added at a multiplicity of infection (MOI) of 100 or 10 and incubated for 1-2 h at 37° C., 5% $CO_2$. In the first experiment where the MOI was 100, plates were centrifuged for 5 min at room temperature at 1000×g. For all other experiments, which used an MOI of 10, this step was omitted. For attachment, M-cells and Caco-2 monolayers were washed two times with sterile PBS and lysed with 0.1% sodium deoxycholate (SDC). For invasion, the media in the upper chamber was removed and replaced with DMEM containing 100 µg/ml gentamicin. The plates were incubated for an additional 1 h at 37° C., 5% $CO_2$. Wells were washed two times with PBS and lysed with 0.1% SDC. Harvested lysate from attachment and invasion collections was diluted and plated onto LB agar plates containing ampicillin. For IL-8 cytokine analysis, infections were done using the same procedure the inventors used for the invasion assay, except that the cells were incubated for 3 h after the addition of gentamicin (4 h time point). For the 24 h time point, the medium in the upper chamber was replaced with DMEM containing 20 µg/ml gentamicin and incubated for an additional 20 h at 37° C., 5% $CO_2$. IL-8 levels in cell culture supernatants at 4 h and 24 h was analyzed using Human IL-8 ELISA Ready-Set-Go!® kit (Affymetrix eBioscience, San Diego, Calif.) per the manufactures instructions. To determine cytotoxic effects of S. typhi on M-cells and Caco-2 monolayers, lactate dehydrogenase (LDH) was measured in the same supernatants used for measuring IL-8 cytokine, using Pierce™ LDH Cytotoxicity Assay Kit (Rockford, Ill.) per the manufacturer's instructions. Supernatants from cells in the absence of S. typhi or treated with 0.1% SDC were used as negative and positive control separately. All experiments were performed at a minimum of triplicate sets.

Immunocytochemistry.

M-Cells and Caco-2 monolayers were fixed with 2% paraformaldehyde in PBS for 20 min, 25° C. on shaker, then permeabilized with 2% paraformaldehyde, 1% Tween-20 in PBS for 20 min, 25° C. on shaker and finally washed 3 times with 1% BSA in PBS. Primary antibodies rabbit anti-galectin 9 (Abcam, Cambridge, Mass.) used at 1:500, Alexa 594®-conjugated anti-ZO-1 (Molecular Probes) used at 5 µg/ml, Fluorescein labeled anti-*Salmonella* CSA-1 (KPL, Gaithersburg, Md.) used at 50 µg/ml, and Fluorescein conjugated UEA-I (Vector Labs) used at 10 µg/ml. Secondary antibody goat anti-rabbit IgG Fc conjugated to Alexa Fluor® 568 (Abcam, Cambridge, Mass.) and Goat Anti-Rabbit IgG Fc conjugated to Alexa Fluor® 647 (Abcam, Cambridge, Mass.) used at 2 µg/ml. Fixed and labeled samples were mounted on slides using Vectashield. Images were obtained using a Leica DM2500 confocal laser scanning microscope. Brightness and contrast were adjusted.

Enzyme-Linked Immunosorbent Assay (ELISA).

To measure IgG antibody response to StgA and LpfA in mouse sera, purified His-tagged StgA and His-tagged LpfA proteins resuspended in sodium carbonate-bicarbonate buffer (pH 9.6) at 1 µg/ml were used to coat polystyrene Nunc MaxiSorp® 96-well flat bottom plates (Fisher). After incubation at 4° C. overnight, the plates were blocked with SEA BLOCK blocking buffer (Fisher). The serum was serially diluted and 100 µl of diluted sample was added to duplicate wells and incubated at 4° C. overnight. After three times PBS-0.05% Tween-20 washing, the plates were incubated with biotinylated goat anti-mouse IgG (Southern Biotechnology Inc., Birmingham, Ala.) antibodies diluted 1:10,000 for 1 h at 25° C. Wells were developed with streptavidin horseradish peroxidase conjugate (Southern Biotechnology Inc., Birmingham, Ala.) at the ratio of 1:4000, followed by ABTS peroxidase substrate (1-component) (KPL, Gaithersburg, Md.). Absorbance was recorded at 405 nm using a SpectraMax M2 Multi-Mode Microplate Reader (Molecular Devices, LLC). Titers were recorded as the last dilution that resulted in 0.1 greater than background and expressed as the reciprocal log 10 values.

Results

Tissue Culture Models.

For these studies, the inventors compared the interactions of S. typhi with polarized Caco-2 cells, which model intestinal enterocytes, with and without co-culture with Raji B cells. Inclusion of Raji B cells drives the differentiation of Caco-2 enterocytes into "M-like" cells (Gullberg, et al. 2000. Expression of specific markers and particle transport in a new human intestinal M-cell model. Biochem Biophys Res Commun 279:808-813). The Caco-2 monocultures produced tight junctions, as determined by the presence of ZO-1 at the interface between cells (FIG. 1A) and bound UEA-I (FIG. 1B), with very little detectable galectin-9 on the cell surface (FIG. 1C) as is typical for human enterocytes (52, 53). Inclusion of Raji B cells drives the differentiation of Caco-2 enterocytes into M-like cells. After 4 days of co-culture with Raji B cells, the cells displayed features typical of human M cells. The M-cell-like monolayers continued to express the tight junction marker ZO-1 (FIG. 1D), the ability to bind to UEA-I was reduced (FIG. 1E) and the cells produced increased levels of galectin-9 (FIG. 1F) (Pielage, et al. 2007. Reversible differentiation of Caco-2 cells reveals galectin-9 as a surface marker molecule for human follicle-associated epithelia and M cell-like cells. Int J Biochem Cell Biol 39:1886-1901; Giannasca, et al. 1999. Human intestinal M cells display the sialyl Lewis A antigen. Infection and Immunity 67:946-953.

Cloning of stgABCC'D and lpfABCDE.

Figures 5A, 5B:
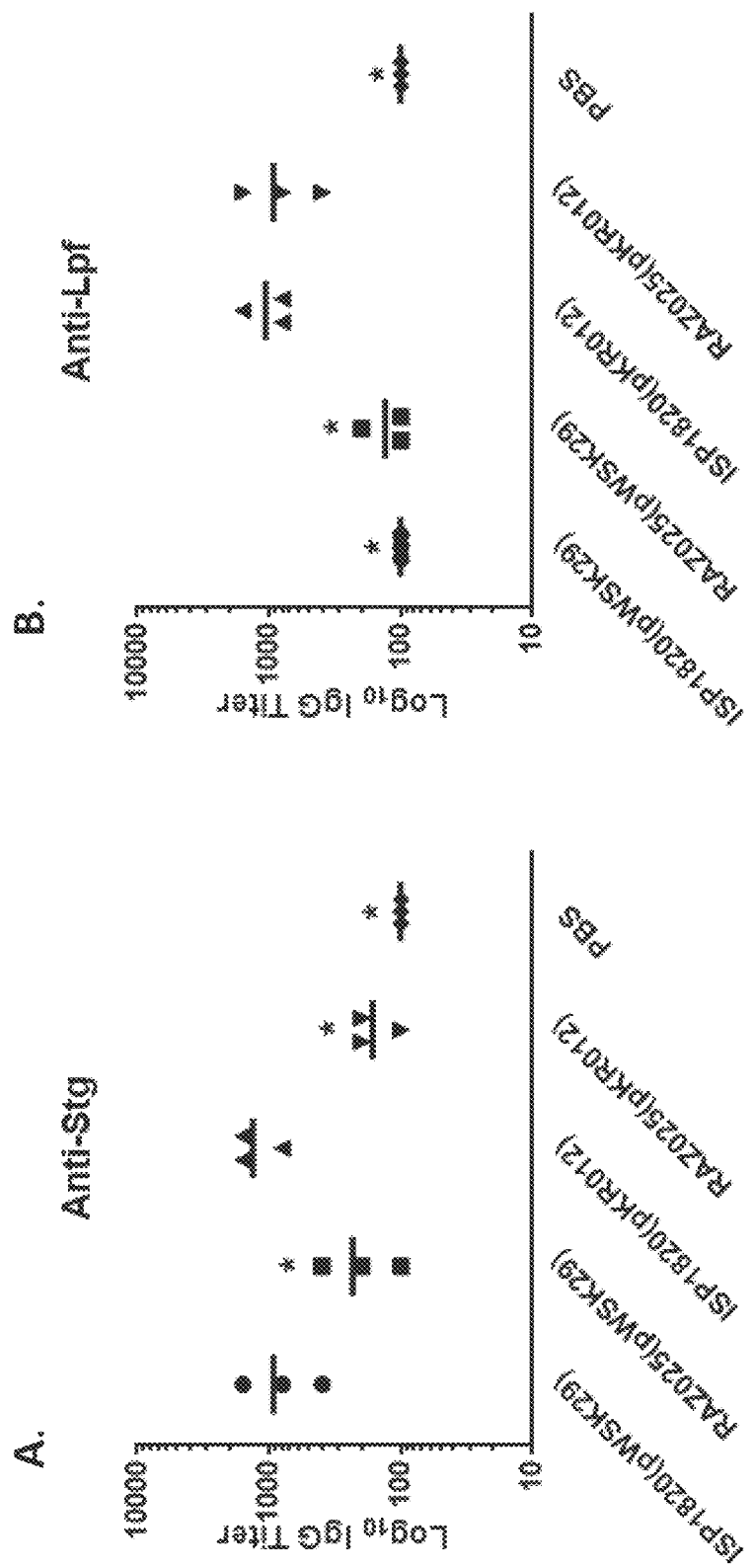

The stgABCC'D and lpfABCDE operons were cloned by PCR into the low copy number plasmid pWSK29 as described in the Materials and Methods section. The DNA sequence of each operon was confirmed by DNA sequence analysis. The inventors were unable to clearly demonstrate production of StgA and LpfA in S. typhi directly by western blot (data not shown). However, the inventors were able to use an indirect method. Mice were immunized 4 times, alternating between oral and IN immunizations, with either ISP1820, ISP1820 Δstg, ISP1820 Lpf$^+$ or ISP1820 Δstg Lpf$^+$. Sera were collected from each group of mice 7 weeks after the initial inoculation and titers against LpfA and StgA determined. Although titers against both fimbrial subunits were low, our results showed that mice inoculated with strains capable of producing StgA mounted an anti-StgA serum IgG response that was 10-fold greater than in mice inoculated with the Δstg strain (FIGS. 5A-5B). Conversely, mice immunized with strains capable of producing LpfA had elevated serum anti-LpfA titers. The inventors infer from these results that the cloned operons were capable of directing the relevant adhesin/fimbriae production in S. typhi.

Stg Fimbriae Block M-Cell Binding.

Figure 2A:
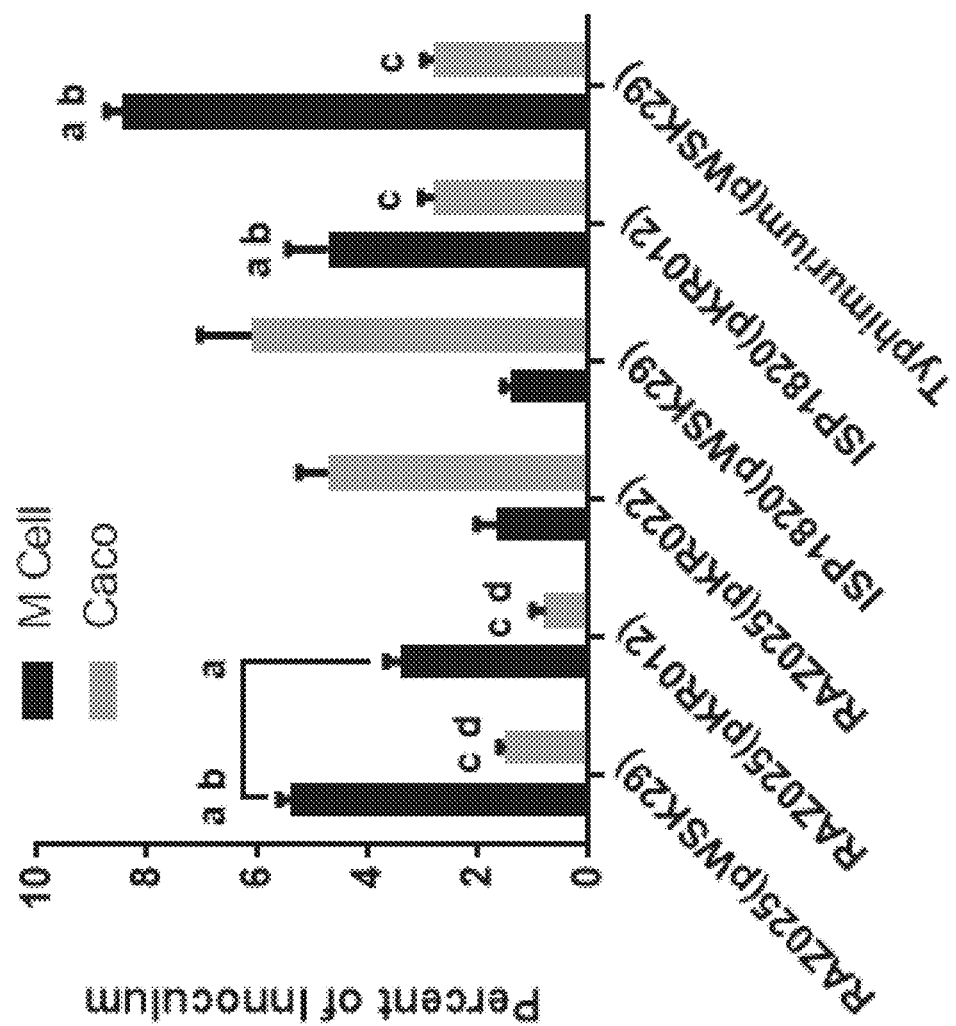
Figure 2B:
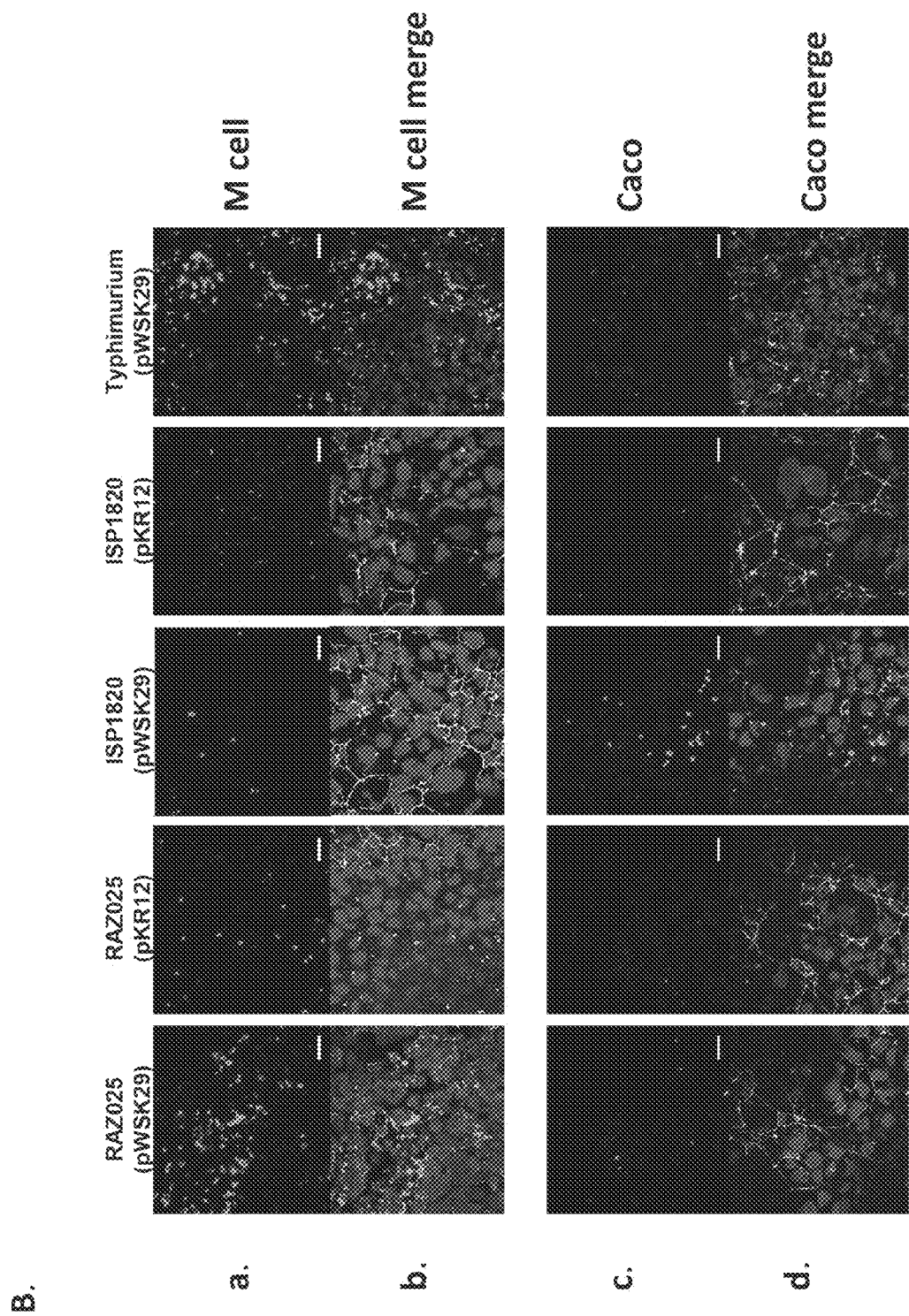
Figure 6:
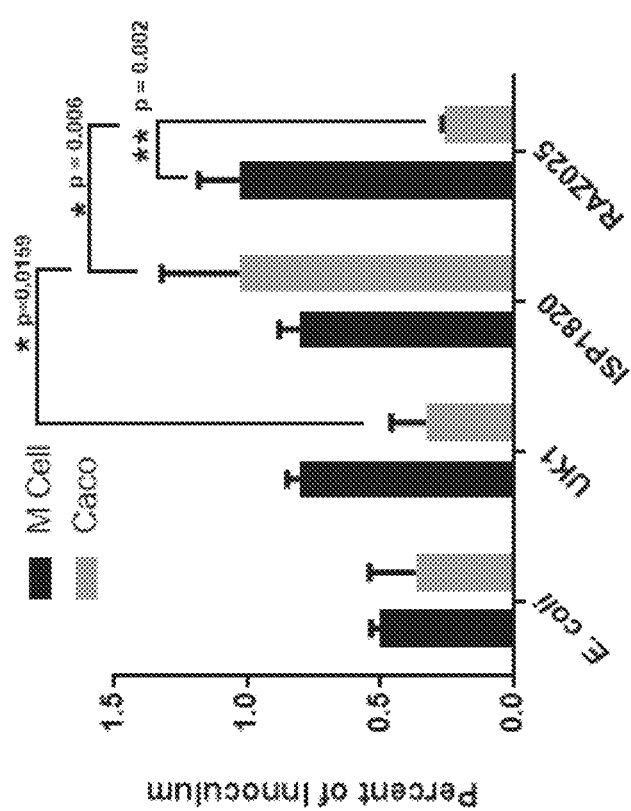

The inventors examined S. typhi adherence to polarized Caco-2 monolayers and Caco-2/Raji B co-cultures (M-like cells). The percentage of S. typhi ISP1820 adhered to Caco-2 cells in greater numbers than S. Typhimurium, or any of the other strains tested (P<0.0001), while adherence of S. Typhimurium to M-like cells was greater than the S. typhi wild-type strain (FIG. 2A, P≤0.02). The S. typhi wild-type strain ISP1820 showed a strong preference for binding to Caco-2 cells over M-like cells (P≤0.01). Deletion of stg reversed this trend. As expected, deletion of stg (RAZ025=ISP1820 Δstg) reduced adherence to Caco-2 cells (P<0.0001). However, adherence to M-like cells was significantly increased compared to ISP1820 (FIG. 2A; P≤0.02). Finally, the Δstg mutant RAZ025 showed a strong preference for binding to M-like cells compared to Caco-2 cells (P≤0.01). Introduction of a plasmid-borne copy of stgABCC'D into the Δstg mutant resulted in an adherence profile similar to the Stg+ parent ISP1820 (FIG. 2A). Adherence preferences were confirmed by confocal microscopy (FIG. 2B). Note that the confocal data was obtained using an MOI of 100 and the data in FIG. 2A was obtained using an MOI of 10. However, the trends observed in FIG. 2A were similar using an MOI of 100 (FIG. 6).

Lpf Fimbriae Blocks Adherence to Caco-2 Cells.

Figure 3:
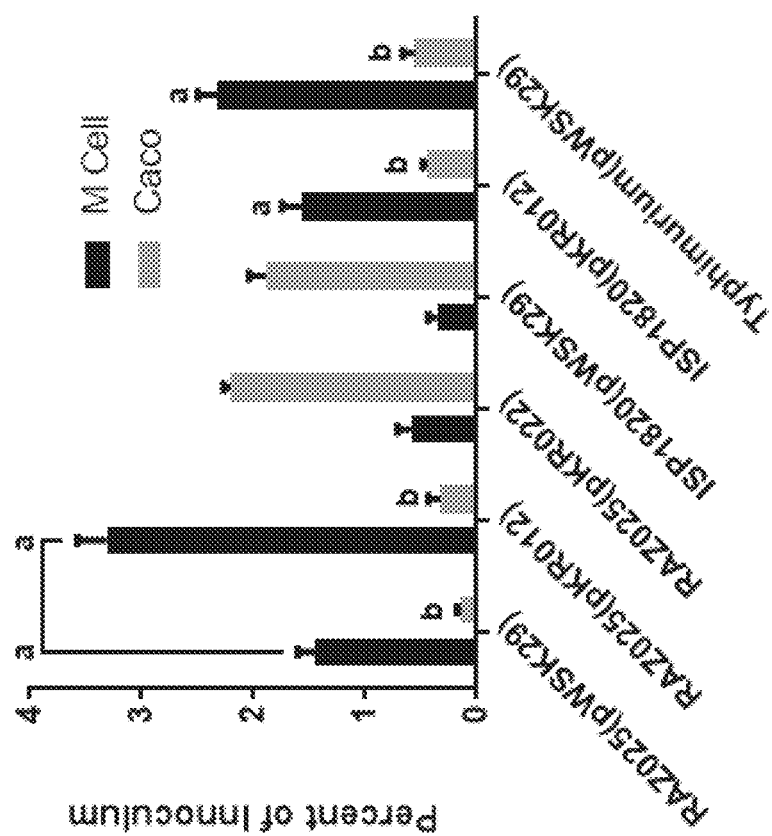

Since lpf has been implicated in binding to M cells, the inventors examined the impact of providing a plasmid-borne copy of lpf (pKR012) to *S. typhi*. Addition of lpf enhanced adherence of ISP1820 to M cells (FIG. 2A) as expected. Surprisingly, the presence of Lpf decreased adherence of RAZ025 to M cells (P=0.02) and reduced adherence of ISP1820 to Caco-2 cells (P<0.0001). The inventors observed a small, but non-significant reduction in Caco-2 cell adherence when the lpf operon was introduced into RAZ025. These quantitative results are supported by the confocal data (FIG. 2B).

Lpf Enhances *S. typhi* Invasion of M Cells.

The inventors examined the impact of Stg and Lpf on invasion. Deletion of stg resulted in decreased invasion of Caco-2 cells (P<0.0001; FIG. 3), a phenotype that was reversed by complementation with pKR022. Introduction of lpf into ISP1820 or RAZ025 (ISP1820 Δstg) resulted in a significant increase in invasion of M cells (P≤0.003). The percent of inoculum of RAZ025 (pKR012) that invaded the M cells similar to the level of invasion seen with S. Typhimurium. These results suggest that, in this setting, Lpf actively promotes M cell invasion.

Impact of Stg and Lpf on IL-8 Secretion.

The *Salmonella* strains were incubated with M-like cells for 4 or 24 hours, at which time the basolateral media was assayed for IL-8. The inventors monitored LDH release as a measure of cell death. In all experiments, LDH levels were low, averaging 5% or less of the amount of LDH detected in lysed cells (data not shown). For ISP1820, there was little IL-8 secretion (FIG. 4). Introduction of Lpf resulted in a slight increase in IL-8 secretion, as did deletion of the stg operon, although neither increase was significant. However, introduction of Lpf into the Δstg *S. typhi* strain resulted in a roughly 10-fold increase in IL-8 levels compared to the parent strain (P=0.003). The secretion profile of the Δstg Lpf *S. typhi* strain was similar to the profile observed for S. Typhimurium (FIG. 4), indicating that these fimbriae can impact host responses to invasion.

Discussion

Peyer's patches are required for mucosal antibody responses (Hashizume, et al. 2008. Peyer's patches are required for intestinal immunoglobulin A responses to *Salmonella* spp. Infection and immunity 76:927-934). They are lymphoid follicles surrounded by a follicle-associated epithelium that includes M cells. The M cells are situated above B cell follicles, T cells, dendritic cells and macrophages. Peyer's patches are required for the induction of mucosal antibody responses against *Salmonella*. Bypassing the PPs during infection has been shown to dramatically reduce the quality of the immune response elicited by S. Typhimurium in mice (Hashizume, et al., 2008. Peyer's patches are required for intestinal immunoglobulin A responses to *Salmonella* spp. Infection and immunity 76:927-934; Martinoli, et al. 2007. Entry route of *Salmonella* typhimurium directs the type of induced immune response. Immunity 27:975-984; Penheiter, et al., 1997. Non-invasive *Salmonella* typhimurium mutants are avirulent because of an inability to enter and destroy M cells of ileal Peyer's patches. Mol Microbiol 24:697-709). Mouse studies using an S. Typhimurium invA mutant defective in colonization of Peyer's patches showed that colonization of Peyer's patches is important driver of mucosal IgA responses. *S. typhi* evades the host immune system by down-regulating or masking its TLR and NOD agonists, including LPS, flagella and T3SS components and effectors (Raffatellu, et al 2008. Clinical pathogenesis of typhoid fever. J Infect Dev Ctries 2:260-266; Winter, et al. 2008. The *Salmonella enterica* serotype *typhi* regulator TviA reduces interleukin-8 production in intestinal epithelial cells by repressing flagellin secretion. Cell Microbiol 10:247-261; Winter, et al. 2014. *Salmonella enterica* Serovar *typhi* conceals the invasion-associated type three secretion system from the innate immune system by gene regulation. PLoS Pathog 10:e1004207). The inventors hypothesized that *S. typhi* also preferentially avoids Peyer's patches during the initial interactions with the host. This would comprise as an additional strategy for avoiding the host immune system.

While it is clear that *S. typhi* can adhere to and invade M cells in the mouse (Kohbata, et al. 1986. Cytopathogenic effect of *Salmonella typhi* GIFU 10007 on M cells of murine ileal Peyer's patches in ligated ileal loops: an ultrastructural study. Microbiol Immunol 30:1225-1237; Pascopella, et al. 1995. Host restriction phenotypes of *Salmonella typhi* and *Salmonella gallinarum*. Infection and immunity 63:4329-4335), it has not been possible to quantify how frequently this occurs versus the frequency at which it invades enterocytes. This question is not easily addressed because (i) the surface area covered by enterocytes is large compared to the tight clusters of M cells in Peyer's patches and (ii) addressing this question is technically challenging since *S. typhi* is host-restricted to humans. The current study provides strong evidence that *S. typhi* displays a preference for enterocytes, while S. Typhimurium preferentially adheres to M cells (FIG. 2).

Stg adhesin/fimbriae are known to enhance *S. typhi* adherence to a number of epithelial cell lines, including INT-407 cells, HEp2 cells and polarized HT-29 cells. The inventors have expanded these findings to include polarized Caco-2 cells. The *S. typhi* Δstg mutant exhibited significantly reduced adherence to polarized Caco-2 cells (FIG. 2A, 2B). Providing stg on a plasmid restored the preferred adherence to Caco-2 cells (FIG. 2A). This quantitative data was supported our confocal microscopy data in which fewer *S. typhi* cells were observed on the Caco-2 monolayers after deletion of stg (FIG. 2B).

Surprisingly, the stg mutant was better able to adhere to M cells than Caco-2 cells in the quantitative assays (FIG. 2A, FIG. 6) and as observed by confocal microscopy (FIG. 2B). Complementation of the stg mutant resulted in an adherence profile similar to the $Stg^+$ parent (FIG. 2A). In fact, the confocal data suggests that *S. typhi* adheres to M cells as well as S. Typhimurium. Taken together, these results suggest that Stg adhesin/fimbriae may block adherence of *S. typhi* to M cells and indicates that *S. typhi* produces an adhesin that facilitates adherence to M cells when Stg is absent. The nature of this M cell adhesin is unknown. Any of the 11 additional fimbrial operons in *S. typhi* (58) may perform this function, though many are considered putative and some carry pseudogenes. Stg blocking of M cell binding could be due to steric hindrance of the M-cell fimbriae/adhesin or via inverse regulation of stg operon and M-cell adhesin operon expression.

Introduction of lpf into *S. typhi* wild-type strain ISP1820 interfered with its ability to bind to and invade Caco-2 cells (FIG. 2A, FIG. 2B). Lpf resulted in a small increase in M cell invasion, but this was not significant (P=0.21) (FIG. 3). However, in both wild-type and the stg mutant, lpf increased adherence and invasion of M cells (P≤0.003) (FIG. 2, FIG. 3). The inventors speculate that this was driven by Lpf-mediated intimate contact, allowing the type 3 secretion system of *Salmonella* pathogenicity island 1 to initiate docking. In S. Typhimurium, type 1 fimbriae have been shown to account for intimate contact prior to SPI-1-mediated docking to HeLa cells (Misselwitz, et al. 2011. *Salmonella enterica* serovar Typhimurium binds to HeLa cells via Fim-mediated reversible adhesion and irreversible type three secretion system 1-mediated docking. Infection and immunity 79:330-341).

Figure 4:
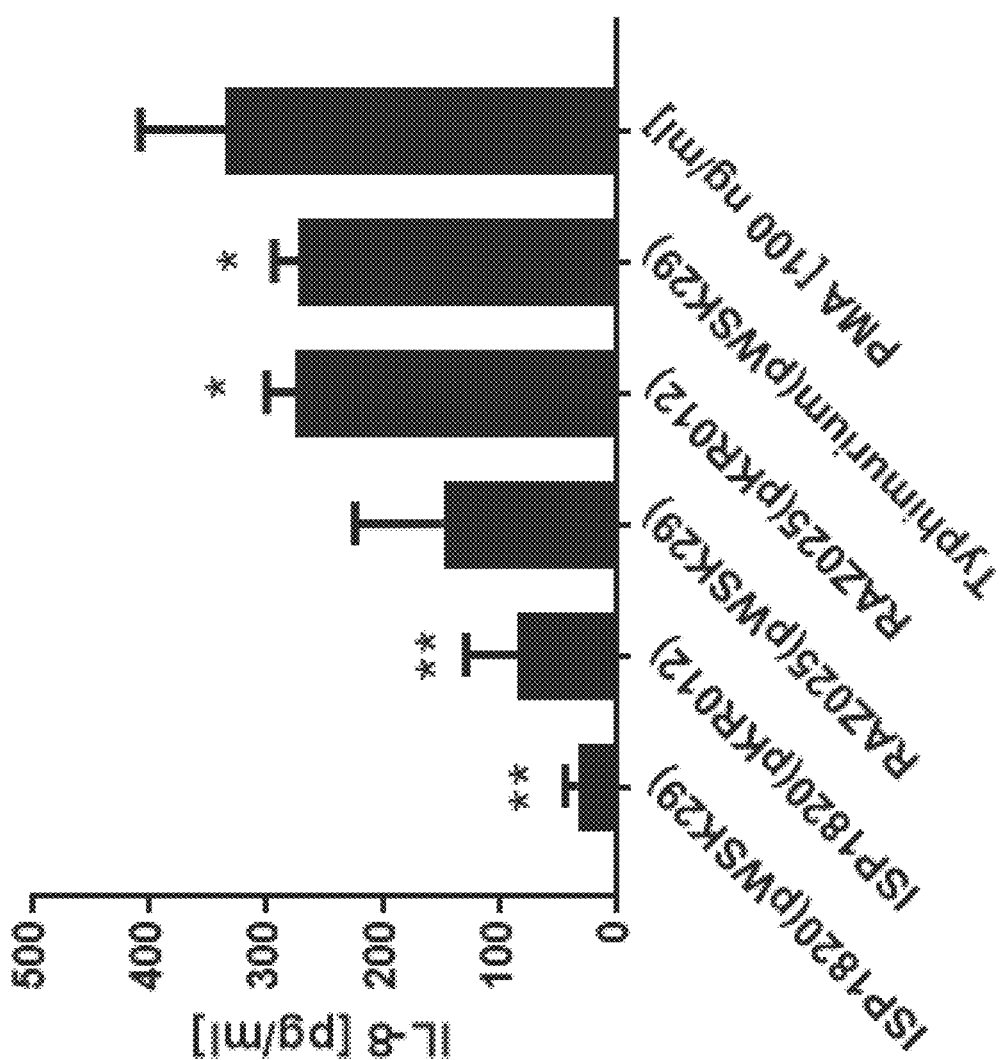

Invasion of polarized epithelial cells by S. Typhimurium induces expression and production of the chemokine IL-8, while *S. typhi* is able to suppress this response. In our study, the inventors examined the amount of IL-8 secreted into the basal chamber after infection of M cells with *S. typhi* at 4 h. Our results were consistent with previous work using a variety of cell types, including Caco-2 and T84 epithelial cells, HEK cells, THP-1 monocytes and human colonic tissue explants. S. Typhimurium induced over 10-fold greater levels of IL-8 than *S. typhi* in the M-cell model (FIG. 4). The lower levels of IL-8 produced by cells infected with *S. typhi* has been shown to be due to immune avoidance due to several virulence traits including Vi antigen and the down-regulation of flagellin and T3SS effectors by TviA, the regulator of Vi antigen synthesis. Infection with the Δstg mutant, RAZ025, resulted in higher IL-8 levels than infection with the parent strain ISP1820, although these levels were still much lower than for S. Typhimurium χ3761 (FIG. 4). Strikingly, infection with RAZ025 carrying the lpf operon resulted in IL-8 levels indistinguishable from S. Typhimurium strain χ3761. These results suggest that when Δstg *S. typhi* invades M cells, it is less able to suppress IL-8 secretion than the Stg+ parent. These studies spotlight the role that fimbriae play in *Salmonella* pathogenesis and suggest that Stg adhesin/fimbriae play a supporting role in immune avoidance by *S. typhi*.

Example 2

Effect of Deleting stgABDC on *S. typhi* Ty2.

Figure 9A:
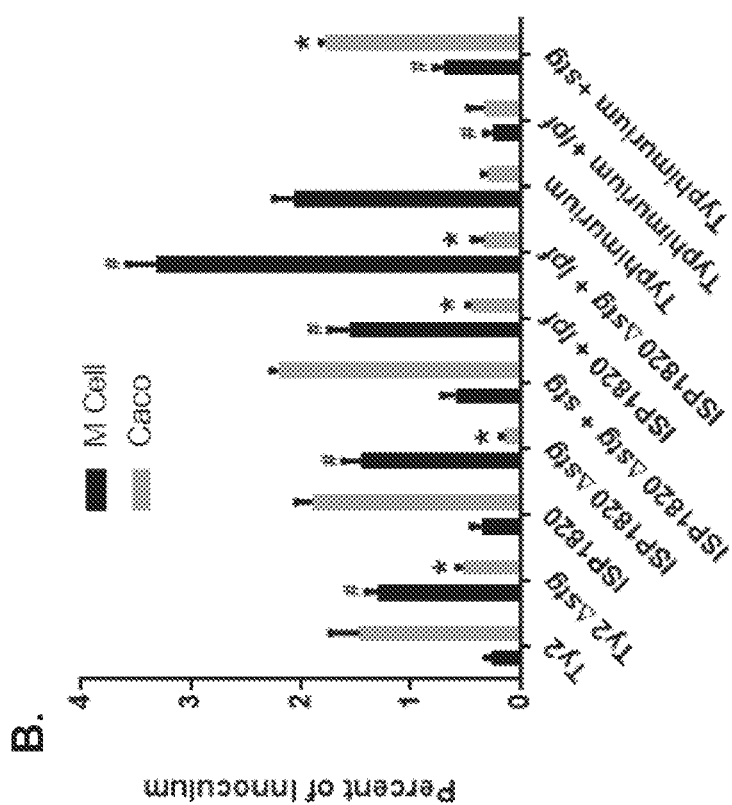
Figure 9B:
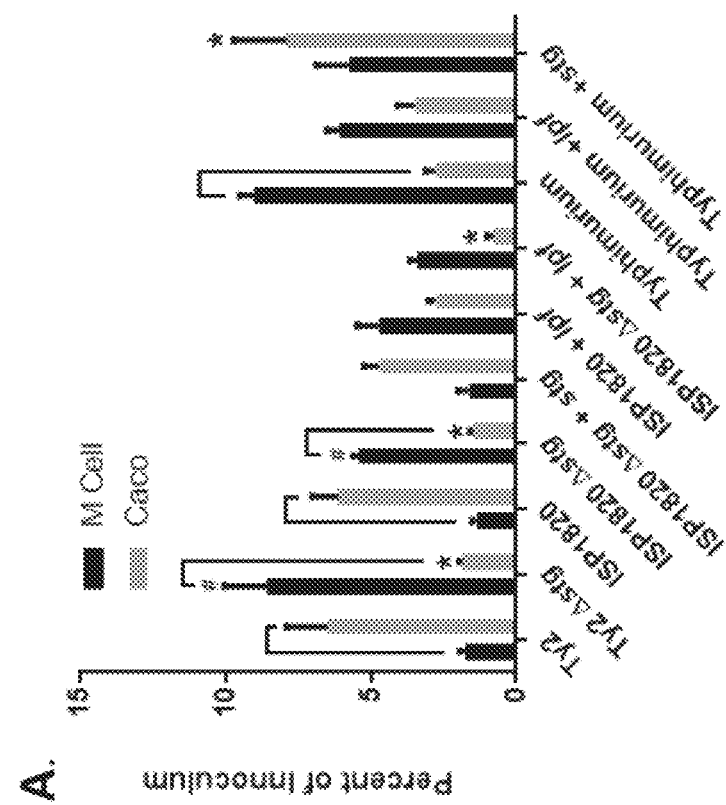

To establish that the results with the Δstg operon deletion derivative of *S. typhi* ISP1820 is not limited to that one strain, RAZ024, a Δstg operon deletion of Ty2 was constructed. Like ISP1820, strain Ty2 adheres to (FIG. 9A) and invades (FIG. 9B) Caco-2 cells better than it does to M-cells in the tissue culture model system. When the stg operon is deleted, the adherence and invasion profiles are reversed and the mutant adheres and invades M-cells better than Caco-2 cells. This result demonstrates that the stg operon deletion has a similar impact on both Ty2 and ISP1820 (FIGS. 9A-9B).

Example 3

In Vivo Effects of Altering *S. typhi* Fimbrial Profiles.

The previous results showed that the combination of a Δstg operon deletion and introduction of Lpf on plasmid pKR012 enhances adherence and invasion of M-cells and reduces adherence and invasion of enterocytes (Caco-2 cells) in tissue culture. The purpose of targeting M cells is to increase colonization of Peyer's patches by *S. typhi*. To address this question, it was investigated how the fimbrial modifications (Δstg and Lpf+) affect the ability of *S. typhi* to colonize the Peyer's patches of mice using ligated ileal loops.

Methods

Ligated Ileal Loops.

BALB/c mice were anesthetized and the ileum surgically exposed. The ileum was divided into two 1.5 cm loops/mouse by tying off each section with suture. Each loop contained one Peyer's patch. Approximately 2×10⁸ CFU of a *S. typhi* strain was injected into each loop. After injection, the mouse was kept alive for one hour under anesthesia and then euthanized. Loops were harvested and rinsed with Hank's Balanced Salts Solution (HBSS). The loops were then incubated overnight at 4° C. in HBSS containing 100 µg/ml gentamicin. Loops were rinsed with HBSS, measured with a caliper and the PP's removed. PPs and the remaining tissue (EP) were individually homogenized and plated onto LB containing appropriate antibiotics for enumeration of bacteria.

Results

Ileal Colonization.

To evaluate the effects of Δstg and Lpf+ on the *S. typhi* strains in vivo, the abilities of ISP1820 (Stg+, Lpf+) and RAZ025 (pKR012) (Stg-, Lpf+) were compared to invade mouse ileal tissues using ligated ileal loops. Differences were observed between ISP1820 and RAZ025 (pKR012) invasion of enterocytes (P<0.001). The numbers of ISP1820 recovered from enterocytes were about 5-fold greater than the numbers of RAZ025 (pKR012) recovered (FIG. 10A), consistent with the tissue culture data. Conversely, over 100-fold more CFUs of strain RAZ025 (pKR012) (Δstg, Lpf+) recovered from PPs than ISP1820. These results are qualitatively similar to the tissue culture results, indicating that deletion of stgABCD and inclusion of Lpf fimbriae into *S. typhi* increases homing to Peyer's patches in vivo.

Figures 10A, 10B:
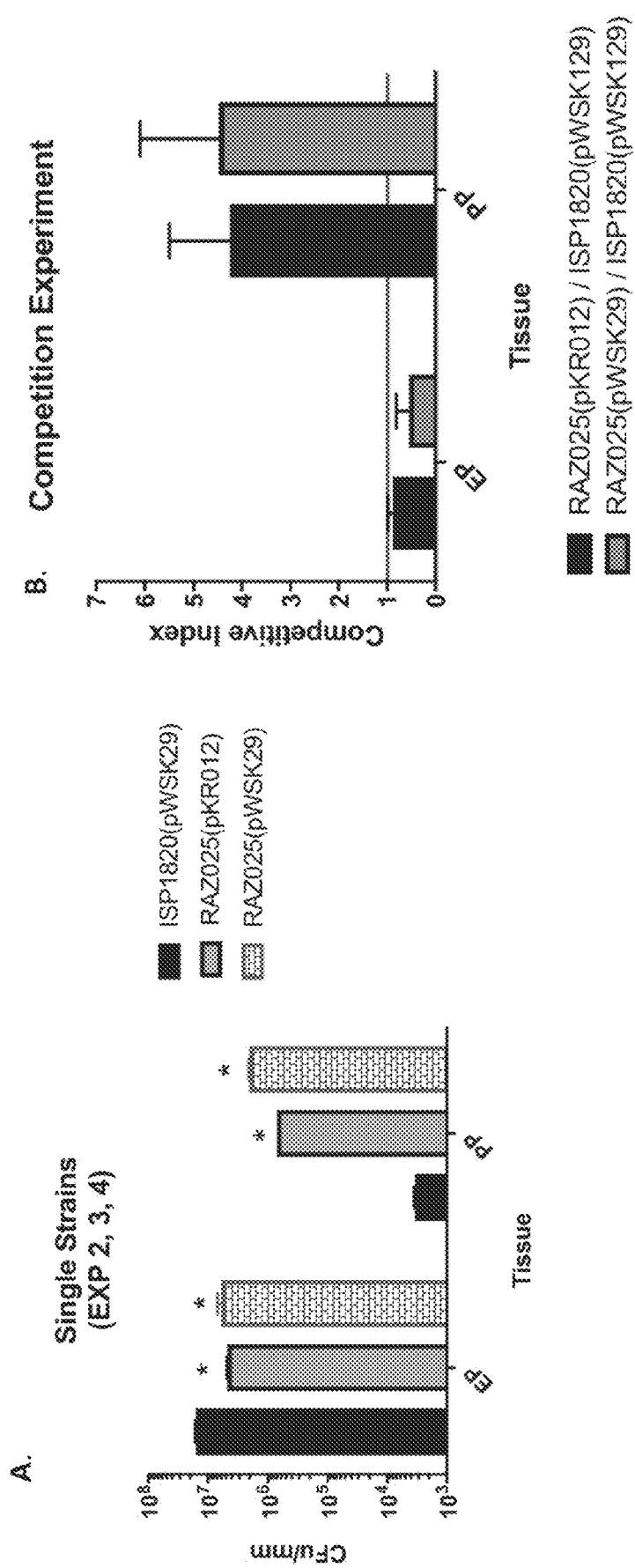
Figure 11:
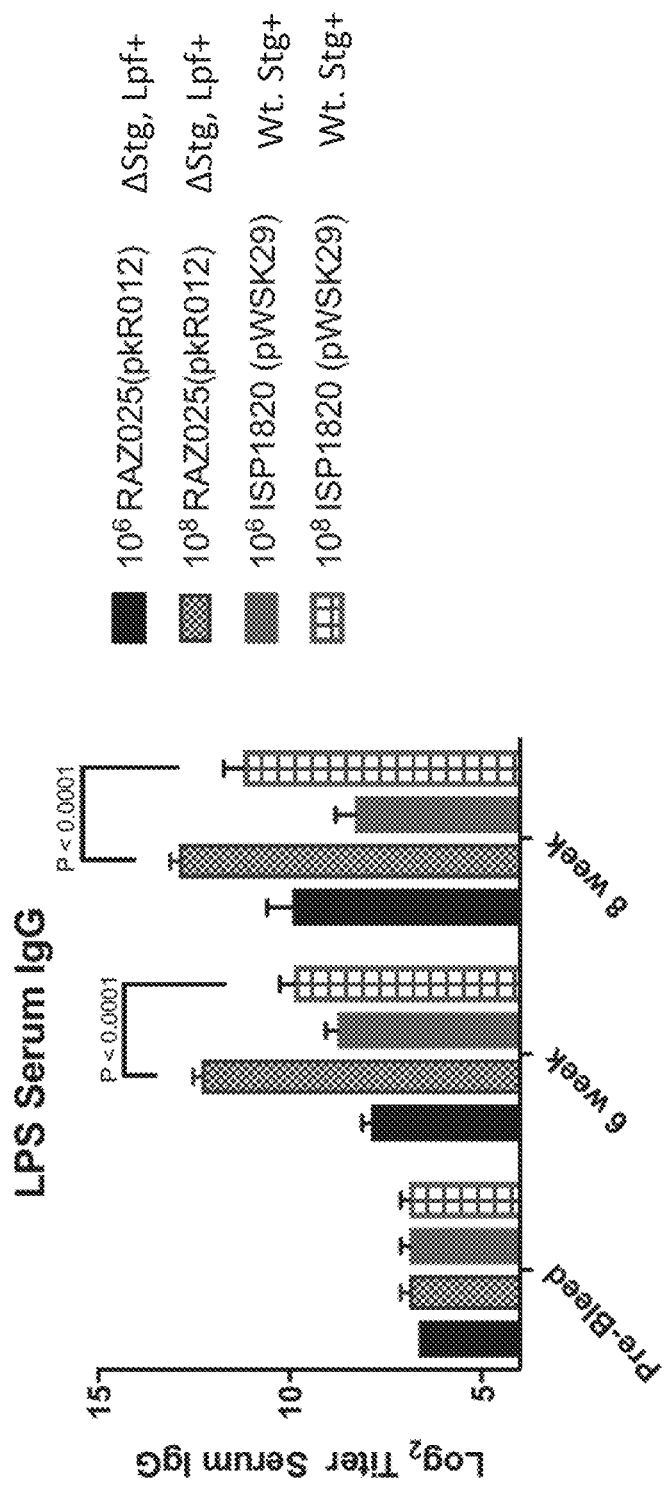

Similarly, in a competition assay in which either the Δstg strain or the Δstg+Lpf strain were co-injected with the ISP1820 parent, the modified strains outcompeted the parent strain for invasion of Peyer's patches (FIG. 10B). These results demonstrate that changing the fimbrial profile alters epithelial cell targeting in vivo.

Example 4

Increased Immunogenicity of Strains with Fimbrial Modifications.

To investigate whether these changes influence immunogenicity, another BALB/c mouse model was utilized. While oral inoculation with *S. typhi* does not elicit a strong immune response in mice, intranasal immunization is effective (Galen J E, Gomez-Duarte O G, Losonsky G A, Halpern J L, Lauderbaugh C S, Kaintuck S, Reymann M K, Levine M M. 1997. A murine model of intranasal immunization to assess the immunogenicity of attenuated *Salmonella typhi* live vector vaccines in stimulating serum antibody responses to expressed foreign antigens. Vaccine 15:700-708.). The feasibility of using an intranasal model was investigated to assess the impact of our modifications on immunogenicity. This model is a reasonable way to evaluate the modified strains because there are M-cells overlaying dendritic cells in the nasal-associated lymphoid tissue (NALT). M-cells in the NALT are capable of sampling inhaled antigens to initiate an antigen-specific immune response (Kim D Y, Sato A, Fukuyama S, Sagara H, Nagatake T, Kong I G, Goda K, Nochi T, Kunisawa J, Sato S, Yokota Y, Lee C H, Kiyono H. 2011. The airway antigen sampling system: respiratory M cells as an alternative gateway for inhaled antigens. J Immunol 186:4253-4262). Although M cells associated with PP have a different lineage than M cells in the NALT, they display similar phenotype and functions, indicating that overlapping genetic programs are induced (Kiyono H, Fukuyama S. 2004. NALT-versus Peyer's-patch-mediated mucosal immunity. Nat Rev Immunol 4:699-710, Wang J, Gusti V, Saraswati A, Lo D D. 2011. Convergent and divergent development among M cell lineages in mouse mucosal epithelium. J Immunol 187:5277-5285). As in the PP, M cells in the NALT overlay B cells, T cells, macrophages and dendritic cells (Kiyono H, Fukuyama S. 2004. NALT-versus Peyer's-patch-mediated mucosal immunity. Nat Rev Immunol 4:699-710). Thus, it was reasoned that the inventors may be able to detect differences in M-cell targeting at an appropriate dose.

Intranasal Immunizations.

Groups of five BALB/c mice were given a single dose ($1 \times 10^6$ or $1 \times 10^8$ CFU) of wild-type or $\Delta$stg Lpf$^+$ *S. typhi*.

Chatfield S N, Dougan G, Khan S A. 2005. Optimization of *Salmonella enterica* serovar *typhi* DeltaaroC DeltassaV der ability to invade Caco-2 cells (Inset FIG. 12). The reason for this unusual phenotype is not known. Examination of the published DNA sequence for Ty21a indicates that the stg operon is essentially identical to Ty2 (Kopecko D J, Sieber H, Ures J A, Furer A, Schlup J, Knof U, Collioud A, Xu D, Colburn K, Dietrich G. 2009. Genetic stability of vaccine strain *Salmonella typhi* Ty21a over 25 years. Int J Med Microbiol 299:233-246) except for an A19V substitution in the deduced aa sequence of the usher StgC, a protein which is truncated at 170 aa due to a premature stop codon (Forest C, Faucher S P, Poirier K, Houle S, Dozois C M, Daigle F. 2007. Contribution of the stg fimbrial operon of *Salmonella enterica* serovar *typhi* during interaction with human cells. Infect Immun 75:5264-5271). It is not clear if this change has is responsible for the observed phenotype in Ty21a. Alternatively, the phenotype may be due to a regulatory mutation (regulation of stg fimbriae production has not been studied) or due to the presence of the galE mutation. Although strain Ty21a was grown in the presence of glucose and galactose to allow formation of complete LPS for this experiment, it is possible that wild-type levels of LPS were not attained. This seems likely, as rough (Rc) forms are known to accumulate during the growth of Ty21a (Kopecko D J, Sieber H, Ures J A, Furer A, Schlup J, Knof U, Collioud A, Xu D, Colburn K, Dietrich G. 2009. Genetic stability of vaccine strain *Salmonella typhi* Ty21a over 25 years. Int J Med Microbiol 299:233-246). *S. typhi* waaI mutants share this chemotype and exhibit a slight reduction in adherence and a significant reduction in invasion of Hep-2 cells (Hoare A, Bittner M, Carter J, Alvarez S, Zaldivar M, Bravo D, Valvano M A, Contreras I. 2006. The outer core lipopolysaccharide of *Salmonella enterica* serovar *typhi* is required for bacterial entry into epithelial cells. Infect Immun 74:1555-1564). In addition, complete 0-antigen is required for *S. typhi* invasion of HeLa cells (Mroczenski-Wildey M J, Di Fabio J L, Cabello F C. 1989. Invasion and lysis of HeLa cell monolayers by *Salmonella typhi*: the role of lipopolysaccharide. Microb Pathog 6:143-152). Despite these concerns, the data show that introduction of the lpf operon into Ty21a results in a dramatic increase in adherence and invasion of M cells (FIG. 12). The lpf operon did not enhance adherence of Ty800 Δstg to M cells, but a modest increase in M cell invasion was observed. These results support the idea that modifying the fimbrial profile of vaccine strains can enhance interactions with human M cells and the impact on Ty21a is substantial.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain illustrative, non-limiting embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant attenuated derivative of a pathogenic *Salmonella enterica* serovar *typhi* cell, wherein (a) one or more genes encoding subunits of a stg operon (*Salmonella typhi* Δstg) are inactivated or deleted resulting in a decrease of Stg adhesin/fimbriae production as compared to genes encoding a wild-type Stg operon (stgABCC'D), and (b) the cell comprises a nucleic acid encoding at least one of a gene encoding a subunit of a long polar fimbriae (Lpf) of *S. enterica* serovar Typhimurium protein, wherein the subunit of Lpf is subunit A (lpfA), subunit B (lpfB), subunit C (lpfC), subunit D (lpfD), and/or subunit E (lpfE).

2. The recombinant *Salmonella* cell of claim 1, wherein the one or more genes encoding subunits the stg operon are inactivated or deleted.

3. The recombinant *Salmonella* cell of claim 1, wherein the at least one of stgA, stgB, stgC, stgC', stgD are inactivated or deleted.

4. The recombinant *Salmonella* cell of claim 1, wherein the decrease of Stg adhesin/fimbriae production is an elimination of Stg adhesin/fimbriae production.

5. A recombinant attenuated derivative of a pathogenic *Salmonella enterica* serovar *typhi* cell, wherein (a) one or more genes encoding subunits of a stg operon (*Salmonella typhi* Δstg) are inactivated or deleted resulting in a decrease of Stg adhesin/fimbriae production as compared to genes encoding a wild-type Stg operon (stgABCC'D), and (b) the cell comprises a nucleic acid encoding at least one of a gene encoding a subunit of a long polar fimbriae (Lpf) of *S. enterica* serovar Typhimurium protein, wherein the one or more genes encoding subunits the Lpf is operably linked to a regulatable promoter.

6. The recombinant bacterium of claim 5, wherein the regulatable promoter is induced by a sugar.

7. The recombinant bacterium of claim 6, wherein the sugar is selected from the group consisting of arabinose and rhamnose.

8. The recombinant bacterium of claim 1, wherein the subunit of Lpf is encoded on a plasmid.

9. The recombinant bacterium of claim 1, wherein the subunit of Lpf is integrated into a chromosome.

10. The recombinant *Salmonella* cell of claim 1, wherein the cell lacks a stg operon (stgABCC'D), and contains an Lpf of *S. enterica* serovar Typhimurium (*Salmonella typhi* Δstg Lpf).

11. The recombinant *Salmonella* cell of claim 1, wherein the Lpf has at least 90% identity to SEQ ID NOS: 21, 22, 23, 24, and/or 25.

12. The recombinant *Salmonella* cell of claim 10, wherein the Lpf has at least 99% identity to SEQ ID NOS: 21, 22, 23, 24, and/or 25.

13. The recombinant *Salmonella* cell of claim 10, wherein the Lpf consists of SEQ ID NOS: 21, 22, 23, 24, and/or 25.

14. The recombinant *Salmonella* cell of claim 1, wherein the *Salmonella* is Ty21a, Ty800, χ9639, χ9640, χ9633, CVD 908, CVD 908-htrA, CVD 909, Ty21a-GAD, MD77, Ty21a-PA-01, Ty21a-Ss or M01ZH09 (also called ZH9).

15. The recombinant *Salmonella* cell of claim 1, wherein the cell further comprises one or more virulence genes encoding pab, aroA, aroC, aroD, asdA, dapA, dam, murA, nadA, pncB, galE, pmi, fur, ompR, htrA, hemA, cdt, cya, crp, phoP, phoQ, rfc, rfaH, poxA, galU, guaB, guaA, hfq, msbB, relA, spoT, ssaV, clpP, clpX, gidA, wecA, genes required for type 3 secretion system function in pathogenicity island 2, or wherein one or more genes for effector molecules secreted by a type 3 secretion system are inactivated, down-regulated in vivo or deleted.

16. The recombinant *Salmonella* cell of claim 14, wherein the gene required for type 3 secretion system function in pathogenicity island 2 is ssaV.

17. The recombinant bacterium of claim 1, wherein the cell comprises an lpfABCDE operon, and the lpfABCDE operon is operably linked to a promoter.

18. The recombinant *Salmonella* cell of claim 17, wherein the promoter is a regulatable or constitutive promoter.

19. The recombinant *Salmonella* cell of claim 14, wherein the recombinant *Salmonella* cell does not produce Lpf fimbriae, but upon induction of the regulatable promoter, the recombinant *Salmonella* cell displays Lpf fimbriae.

* * * * *

SEQUENCE LISTING

<160> NUMBER OF SEQ ID NOS: 25

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcggaattcg tcatatcaat gaactacggc                                    30

<210> SEQ ID NO 2
<211> LENGTH: 28
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 2
cgctctagac tccagcatct gagtgagg                                            28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcggaattcc ggaagcgaat actatccc                                            28

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgcggcgcgc cgattgtggt ggcgccgaac                                          30

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggatccatgg catctgatgg caccg                                               25

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcgacgcga atcttatttt tggtattcg                                           29

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggatccgctg aatctggtga cggcac                                              26

<210> SEQ ID NO 8
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
gtcgaccatg attctcttcc tgagcctc                                            28

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gccggatccc gcagtgataa cagctcttg                                           29

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcgctcgaga gcacggttaa gtagaccac                                           29

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaattcggaa gcctatgctg caggc                                               25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcgaggcgg aacaactggt caggg                                               25

<210> SEQ ID NO 13
<211> LENGTH: 5619
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(534)
<220> FEATURE:
<221> NAME/KEY: CDS
<222> LOCATION: (622)..(1317)
<220> FEATURE:
<221> NAME/KEY: CDS
<222> LOCATION: (1343)..(3868)
```

```
<220> FEATURE:
<221> NAME/KEY: CDS
<222> LOCATION: (4435)..(4956)
<220> FEATURE:
<221> NAME/KEY: CDS
<222> LOCATION: (4965)..(5489)

<400> SEQUENCE: 13
```

| | | | | | | | | | | | | | | | | |
|---|---|---|---|---|---|---|---|---|---|---|---|---|---|---|---|---|
| atg | gag | ttt | tta | atg | aaa | aag | gtt | gtt | ttt | gct | ctg | tct | gct | ctc | gct | 48 |
| Met | Glu | Phe | Leu | Met | Lys | Lys | Val | Val | Phe | Ala | Leu | Ser | Ala | Leu | Ala | |
| 1 | | | | 5 | | | | | 10 | | | | | 15 | | |

| gta | gtt | tcc | act | tct | gct | ttc | gct | gct | gaa | tct | ggt | gac | ggc | acc | att | 96 |
|---|---|---|---|---|---|---|---|---|---|---|---|---|---|---|---|---|
| Val | Val | Ser | Thr | Ser | Ala | Phe | Ala | Ala | Glu | Ser | Gly | Asp | Gly | Thr | Ile | |
| | | | 20 | | | | | 25 | | | | | 30 | | | |

| aaa | ttc | acc | ggt | gaa | atc | gtt | gac | gcg | cca | tgc | gtc | gtt | tct | act | gac | 144 |
|---|---|---|---|---|---|---|---|---|---|---|---|---|---|---|---|---|
| Lys | Phe | Thr | Gly | Glu | Ile | Val | Asp | Ala | Pro | Cys | Val | Val | Ser | Thr | Asp | |
| | | 35 | | | | | 40 | | | | | 45 | | | | |

| tcc | cag | aac | cag | gaa | gtt | gtg | ctg | ggt | cag | gtt | aag | aaa | aat | atc | ttc | 192 |
|---|---|---|---|---|---|---|---|---|---|---|---|---|---|---|---|---|
| Ser | Gln | Asn | Gln | Glu | Val | Val | Leu | Gly | Gln | Val | Lys | Lys | Asn | Ile | Phe | |
| | 50 | | | | | 55 | | | | | 60 | | | | | |

| aaa | gcc | att | ggc | gac | aag | tct | tct | tct | aag | cct | ttc | cag | atc | aaa | ctg | 240 |
|---|---|---|---|---|---|---|---|---|---|---|---|---|---|---|---|---|
| Lys | Ala | Ile | Gly | Asp | Lys | Ser | Ser | Ser | Lys | Pro | Phe | Gln | Ile | Lys | Leu | |
| 65 | | | | | 70 | | | | | 75 | | | | | 80 | |

| gaa | gac | tgt | gac | atc | acc | tct | aat | acc | aaa | gtt | aac | gta | agc | ttc | aat | 288 |
|---|---|---|---|---|---|---|---|---|---|---|---|---|---|---|---|---|
| Glu | Asp | Cys | Asp | Ile | Thr | Ser | Asn | Thr | Lys | Val | Asn | Val | Ser | Phe | Asn | |
| | | | | 85 | | | | | 90 | | | | | 95 | | |

| ggc | gtt | ggt | gat | aca | gac | gat | gcg | aca | ctg | gtt | tct | gtt | aac | act | gaa | 336 |
|---|---|---|---|---|---|---|---|---|---|---|---|---|---|---|---|---|
| Gly | Val | Gly | Asp | Thr | Asp | Asp | Ala | Thr | Leu | Val | Ser | Val | Asn | Thr | Glu | |
| | | | 100 | | | | | 105 | | | | | 110 | | | |

| gca | ggt | gcg | gca | act | ggc | gtg | ggc | atc | ggt | atc | tac | gac | aac | gct | aac | 384 |
|---|---|---|---|---|---|---|---|---|---|---|---|---|---|---|---|---|
| Ala | Gly | Ala | Ala | Thr | Gly | Val | Gly | Ile | Gly | Ile | Tyr | Asp | Asn | Ala | Asn | |
| | | 115 | | | | | 120 | | | | | 125 | | | | |

| aag | ctt | gtt | gaa | atg | aac | acc | ggt | aaa | tcc | acc | act | acg | ttg | gct | gct | 432 |
|---|---|---|---|---|---|---|---|---|---|---|---|---|---|---|---|---|
| Lys | Leu | Val | Glu | Met | Asn | Thr | Gly | Lys | Ser | Thr | Thr | Thr | Leu | Ala | Ala | |
| | 130 | | | | | 135 | | | | | 140 | | | | | |

| ggt | cag | acc | gtg | ctg | tac | tac | acc | gct | aac | tac | gtt | gca | aca | aaa | gat | 480 |
|---|---|---|---|---|---|---|---|---|---|---|---|---|---|---|---|---|
| Gly | Gln | Thr | Val | Leu | Tyr | Tyr | Thr | Ala | Asn | Tyr | Val | Ala | Thr | Lys | Asp | |
| 145 | | | | | 150 | | | | | 155 | | | | | 160 | |

| act | gta | acc | act | ggt | tac | ggt | aac | gca | gaa | gtg | gac | ttc | aac | ctg | tcc | 528 |
|---|---|---|---|---|---|---|---|---|---|---|---|---|---|---|---|---|
| Thr | Val | Thr | Thr | Gly | Tyr | Gly | Asn | Ala | Glu | Val | Asp | Phe | Asn | Leu | Ser | |
| | | | | 165 | | | | | 170 | | | | | 175 | | |

| tac | gaa | taatcgaatt ttcgttaata cagacaatca taatggcaac ggaaatcccg | | | | | | | | | | | | | | 584 |
|---|---|---|---|---|---|---|---|---|---|---|---|---|---|---|---|---|
| Tyr | Glu | | | | | | | | | | | | | | | |

| ttgccatttt ttccagcgga ggctcaggaa gagaatc atg aac cgc tca cgt ttg | | | | | | | | | | | | | | | | 639 |
|---|---|---|---|---|---|---|---|---|---|---|---|---|---|---|---|---|
| | | | | | | Met | Asn | Arg | Ser | Arg | Leu | | | | | |
| | | | | | | | | 180 | | | | | | | | |

| ata | tct | tgc | aca | gca | ctg | gtg | ctg | gcg | ttg | att | gct | caa | aac | agt | ttt | 687 |
|---|---|---|---|---|---|---|---|---|---|---|---|---|---|---|---|---|
| Ile | Ser | Cys | Thr | Ala | Leu | Val | Leu | Ala | Leu | Ile | Ala | Gln | Asn | Ser | Phe | |
| 185 | | | | | 190 | | | | | 195 | | | | | 200 | |

| gcc | gga | ggc | gtg | gca | tta | agc | agc | acg | cgt | gtt | att | tat | gac | ggt | agt | 735 |
|---|---|---|---|---|---|---|---|---|---|---|---|---|---|---|---|---|
| Ala | Gly | Gly | Val | Ala | Leu | Ser | Ser | Thr | Arg | Val | Ile | Tyr | Asp | Gly | Ser | |
| | | | | 205 | | | | | 210 | | | | | 215 | | |

| aga | aag | gaa | gct | tct | ctt | acg | gta | aat | aat | aaa | agc | acc | acg | gat | gaa | 783 |
|---|---|---|---|---|---|---|---|---|---|---|---|---|---|---|---|---|
| Arg | Lys | Glu | Ala | Ser | Leu | Thr | Val | Asn | Asn | Lys | Ser | Thr | Thr | Asp | Glu | |
| | | | | 220 | | | | | 225 | | | | | 230 | | |

| ttt | ctc | att | cag | tca | tgg | att | gat | gat | gct | aac | ggt | aat | aaa | aag | acg | 831 |
|---|---|---|---|---|---|---|---|---|---|---|---|---|---|---|---|---|
| Phe | Leu | Ile | Gln | Ser | Trp | Ile | Asp | Asp | Ala | Asn | Gly | Asn | Lys | Lys | Thr | |
| | | 235 | | | | | 240 | | | | | 245 | | | | |

| ccc | ttt | atc | atc | act | cca | ccg | tta | ttt | aaa | tta | agc | ccg | act | aaa | aat | 879 |
|---|---|---|---|---|---|---|---|---|---|---|---|---|---|---|---|---|
| Pro | Phe | Ile | Ile | Thr | Pro | Pro | Leu | Phe | Lys | Leu | Ser | Pro | Thr | Lys | Asn | |
| | 250 | | | | | 255 | | | | | 260 | | | | | |

-continued

| | | |
|---|---|---|
| aac gtt tta cgt att gtt aat acg acg aac acg tta ccg cag gat cgc<br>Asn Val Leu Arg Ile Val Asn Thr Thr Asn Thr Leu Pro Gln Asp Arg<br>265                           270                    275                280 | 927 |
| gag tcc gtt tat tgg att aac gta aaa gct att cct gcc aaa agt gaa<br>Glu Ser Val Tyr Trp Ile Asn Val Lys Ala Ile Pro Ala Lys Ser Glu<br>                    285                    290                    295 | 975 |
| gac gcg gaa gct aaa aac gta ctg cag atc gcc gta cgt acc cgc tta<br>Asp Ala Glu Ala Lys Asn Val Leu Gln Ile Ala Val Arg Thr Arg Leu<br>300                           305                    310 | 1023 |
| aaa ctg ttc tat cgc ccg gcg ggc ctg aaa ggc aat agc atg gac ggc<br>Lys Leu Phe Tyr Arg Pro Ala Gly Leu Lys Gly Asn Ser Met Asp Gly<br>                    315                    320                    325 | 1071 |
| tgg aac aaa ctg cag ttc acc agc gca ggg gct aac cag atc aaa gtg<br>Trp Asn Lys Leu Gln Phe Thr Ser Ala Gly Ala Asn Gln Ile Lys Val<br>330                           335                    340 | 1119 |
| gaa aac cca tct gcc ttt aac ctg acg ttt aat aaa ttt tat gcc aac<br>Glu Asn Pro Ser Ala Phe Asn Leu Thr Phe Asn Lys Phe Tyr Ala Asn<br>345                         350                    355                360 | 1167 |
| ggc cgt gat att gaa aaa acg gga atg gtt ccg gca aaa ggc tca ttg<br>Gly Arg Asp Ile Glu Lys Thr Gly Met Val Pro Ala Lys Gly Ser Leu<br>                    365                    370                    375 | 1215 |
| aat att gaa ctg cca gcc ggc acc ggc aag gta agc gaa gtt aaa tac<br>Asn Ile Glu Leu Pro Ala Gly Thr Gly Lys Val Ser Glu Val Lys Tyr<br>                380                    385                    390 | 1263 |
| aac att att aat gac ttt ggc act gct ggc gac atg ttg aca cag cgc<br>Asn Ile Ile Asn Asp Phe Gly Thr Ala Gly Asp Met Leu Thr Gln Arg<br>                    395                    400                    405 | 1311 |
| gtt aac taacacgttt taaaggatta ttact atg aca tgg acg cat ctt cct<br>Val Asn                                              Met Thr Trp Thr His Leu Pro<br>410                                                                           415 | 1363 |
| ctg ggc aat aag acc tcg cgt ttc acg cag tct gcg ctt gcg ctg atg<br>Leu Gly Asn Lys Thr Ser Arg Phe Thr Gln Ser Ala Leu Ala Leu Met<br>                420                    425                    430 | 1411 |
| ata gcg ggt acg ctc ccc gcg tat gcg gga aca ttt aac ccg cgc ttt<br>Ile Ala Gly Thr Leu Pro Ala Tyr Ala Gly Thr Phe Asn Pro Arg Phe<br>          435                    440                    445 | 1459 |
| ctg gag gat gtg ccg ggt att gat cag cac gtt gac ctt tca atg tat<br>Leu Glu Asp Val Pro Gly Ile Asp Gln His Val Asp Leu Ser Met Tyr<br>450                         455                    460                    465 | 1507 |
| gaa tcc aat aaa gct gaa cac ctg cca ggt aaa tac cgc gtc tcg gtg<br>Glu Ser Asn Lys Ala Glu His Leu Pro Gly Lys Tyr Arg Val Ser Val<br>                470                    475                    480 | 1555 |
| gtg gtc aac gaa aaa aaa atg gag tct cgc acc ctg gag ttt aag gca<br>Val Val Asn Glu Lys Lys Met Glu Ser Arg Thr Leu Glu Phe Lys Ala<br>                    485                    490                    495 | 1603 |
| gcg aca gag gcg cag cgc gca aaa atg ggt gaa tcc ctg gtg ccg tgc<br>Ala Thr Glu Ala Gln Arg Ala Lys Met Gly Glu Ser Leu Val Pro Cys<br>500                         505                    510 | 1651 |
| tta agt cgc gtg cag ctt gaa gat atg ggc gtg cgt att gat agc ttc<br>Leu Ser Arg Val Gln Leu Glu Asp Met Gly Val Arg Ile Asp Ser Phe<br>                515                    520                    525 | 1699 |
| ccg gcg ctg aaa atg gcc ccg cct gaa gcc tgt gtt gct ttt gac gac<br>Pro Ala Leu Lys Met Ala Pro Pro Glu Ala Cys Val Ala Phe Asp Asp<br>530                         535                    540                545 | 1747 |
| att att ccc cag gcc gcc agc cat ttc gac ttt gca gac cag acc ctg<br>Ile Ile Pro Gln Ala Ala Ser His Phe Asp Phe Ala Asp Gln Thr Leu<br>                    550                    555                    560 | 1795 |
| atc atg agc ttc ccg cag gct gcg atg aag cag aca gcg cgc ggt acg<br>Ile Met Ser Phe Pro Gln Ala Ala Met Lys Gln Thr Ala Arg Gly Thr<br>                565                    570                    575 | 1843 |

-continued

| | | |
|---|---|---|
| gtg cca gaa tcg cag tgg gac gaa ggg gtg aat gcc ctg ctg gtg gat<br>Val Pro Glu Ser Gln Trp Asp Glu Gly Val Asn Ala Leu Leu Val Asp<br>580                     585                     590 | 1891 |
| tat aac ttt tcc ggc agc aac gcc agc tat gac gca cac gac agt gaa<br>Tyr Asn Phe Ser Gly Ser Asn Ala Ser Tyr Asp Ala His Asp Ser Glu<br>595                     600                     605 | 1939 |
| acc agc tac aac agc gac agc tac tat ctg aat ctg cgc agc ggt atg<br>Thr Ser Tyr Asn Ser Asp Ser Tyr Tyr Leu Asn Leu Arg Ser Gly Met<br>610                     615                     620                     625 | 1987 |
| aac ctg ggg gca tgg cgg tta cgt aac tat agc acc tgg acg cga aac<br>Asn Leu Gly Ala Trp Arg Leu Arg Asn Tyr Ser Thr Trp Thr Arg Asn<br>630                     635                     640 | 2035 |
| gac ggt aac aac aca tgg gat aac att ggc aca tcc tta agc cgt gcc<br>Asp Gly Asn Asn Thr Trp Asp Asn Ile Gly Thr Ser Leu Ser Arg Ala<br>645                     650                     655 | 2083 |
| att gta ccg ctg aaa tca cag ctg acg ttg ggg gat acc tcc act gcc<br>Ile Val Pro Leu Lys Ser Gln Leu Thr Leu Gly Asp Thr Ser Thr Ala<br>660                     665                     670 | 2131 |
| ggt gat att ttt gac agc gtt cag atg cgc ggt gtg cag tta act tcc<br>Gly Asp Ile Phe Asp Ser Val Gln Met Arg Gly Val Gln Leu Thr Ser<br>675                     680                     685 | 2179 |
| gac gaa gag atg ctg cct gac agc cag cgc ggg ttt gcg ccc gtc atc<br>Asp Glu Glu Met Leu Pro Asp Ser Gln Arg Gly Phe Ala Pro Val Ile<br>690                     695                     700                     705 | 2227 |
| cgg ggt att gcc aaa agt aac gcc gaa gtt acc gtt gag cag aac aac<br>Arg Gly Ile Ala Lys Ser Asn Ala Glu Val Thr Val Glu Gln Asn Asn<br>710                     715                     720 | 2275 |
| tac gtt att tac cgt acg ttt gtt cag ccg ggt gcg ttt gaa att aac<br>Tyr Val Ile Tyr Arg Thr Phe Val Gln Pro Gly Ala Phe Glu Ile Asn<br>725                     730                     735 | 2323 |
| gac ctg tat cca acc tca aac agc ggc gac ctg acg gtc acc att aaa<br>Asp Leu Tyr Pro Thr Ser Asn Ser Gly Asp Leu Thr Val Thr Ile Lys<br>740                     745                     750 | 2371 |
| gaa tcg gac ggc agt gag cag aag ttc gtt cag ccg ttc tcc tcg gtg<br>Glu Ser Asp Gly Ser Glu Gln Lys Phe Val Gln Pro Phe Ser Ser Val<br>755                     760                     765 | 2419 |
| gcg ctc ctc cag cgt gaa ggc cat ctc aaa tac agc ctt tcc gcc ggg<br>Ala Leu Leu Gln Arg Glu Gly His Leu Lys Tyr Ser Leu Ser Ala Gly<br>770                     775                     780                     785 | 2467 |
| gaa tac cgt gcc ggg aac tat aac agc gcc gag ccg aaa ttc ggg cag<br>Glu Tyr Arg Ala Gly Asn Tyr Asn Ser Ala Glu Pro Lys Phe Gly Gln<br>790                     795                     800 | 2515 |
| ctt gat gcc atg tac ggc ctg ccg tat ggc ttt acc gtt tac ggt ggt<br>Leu Asp Ala Met Tyr Gly Leu Pro Tyr Gly Phe Thr Val Tyr Gly Gly<br>805                     810                     815 | 2563 |
| gcg atc ttc tct gac gac tat tac tcg ctg gcg gga gga tta ggt aaa<br>Ala Ile Phe Ser Asp Asp Tyr Tyr Ser Leu Ala Gly Gly Leu Gly Lys<br>820                     825                     830 | 2611 |
| aac ttc ggt tat atc ggc gcg atc tcc atc gat gta acc cag gca aaa<br>Asn Phe Gly Tyr Ile Gly Ala Ile Ser Ile Asp Val Thr Gln Ala Lys<br>835                     840                     845 | 2659 |
| agc aag ctg gca aat gag gag aat tcg gaa ggt cag tct tat cgt ttc<br>Ser Lys Leu Ala Asn Glu Glu Asn Ser Glu Gly Gln Ser Tyr Arg Phe<br>850                     855                     860                     865 | 2707 |
| ctc tac tcc aag agc ttt aac agc ggt aca gat ttc cgt ctg ctg ggt<br>Leu Tyr Ser Lys Ser Phe Asn Ser Gly Thr Asp Phe Arg Leu Leu Gly<br>870                     875                     880 | 2755 |
| tac aag tat tcg acc agc ggc tat tac acc ttc cag gaa gcg acg gat<br>Tyr Lys Tyr Ser Thr Ser Gly Tyr Tyr Thr Phe Gln Glu Ala Thr Asp<br>885                     890                     895 | 2803 |

```
                                                             -continued gtg cgc agc gat gcg gac agc tct tat agc cag tac cac aaa cgt agt       2851
Val Arg Ser Asp Ala Asp Ser Ser Tyr Ser Gln Tyr His Lys Arg Ser
            900                 905                 910 cag att cag ggc aac gtg acg cag caa ctg ggc gcc tgg ggc tcg gtc       2899
Gln Ile Gln Gly Asn Val Thr Gln Gln Leu Gly Ala Trp Gly Ser Val
        915                 920                 925 tat ttt aac gtc acg cag cag gac tac tgg aac gat gaa ggt aaa cag       2947
Tyr Phe Asn Val Thr Gln Gln Asp Tyr Trp Asn Asp Glu Gly Lys Gln
930                 935                 940                 945 cgt tcg ctg aat gcc ggt tat aac ggc cgt att ggc cgc gtg aac tac       2995
Arg Ser Leu Asn Ala Gly Tyr Asn Gly Arg Ile Gly Arg Val Asn Tyr
                950                 955                 960 agc gtt gct tac acc tgg acg aaa agc ccg gag tgg gat gag agc gat       3043
Ser Val Ala Tyr Thr Trp Thr Lys Ser Pro Glu Trp Asp Glu Ser Asp
            965                 970                 975 cgt tta ctg tca ttc tcc atg tcg att cca ctg gga cgc gtg tgg agt       3091
Arg Leu Leu Ser Phe Ser Met Ser Ile Pro Leu Gly Arg Val Trp Ser
        980                 985                 990 aac tac cac ctc acg acc gat cag cat ggc cga acc aac cag cag tta       3139
Asn Tyr His Leu Thr Thr Asp Gln His Gly Arg Thr Asn Gln Gln Leu
995                 1000                1005 ggg gtg agc ggc acc gcg ctg gaa gac cac aac ctg aac tat agt           3184
Gly Val Ser Gly Thr Ala Leu Glu Asp His Asn Leu Asn Tyr Ser
1010                1015                1020 gtg cag gaa ggc tac ggc agc aac ggc gtg ggt aac agc ggc agc           3229
Val Gln Glu Gly Tyr Gly Ser Asn Gly Val Gly Asn Ser Gly Ser
1025                1030                1035 gtg aac ctg gat tac cag ggc ggc gtg ggt agc gcc agc ctg ggt           3274
Val Asn Leu Asp Tyr Gln Gly Gly Val Gly Ser Ala Ser Leu Gly
1040                1045                1050 tac aac tac aac cgt gac ggc cag cag gtg aac tac ggt ttg cgc           3319
Tyr Asn Tyr Asn Arg Asp Gly Gln Gln Val Asn Tyr Gly Leu Arg
1055                1060                1065 ggc ggt gtg ata gcc cat agc gaa ggt atc act ctt tct caa ccg           3364
Gly Gly Val Ile Ala His Ser Glu Gly Ile Thr Leu Ser Gln Pro
1070                1075                1080 ctg ggt gaa tcc atg gcc att atc tcc gcg ccg ggc gcg cgc ggc           3409
Leu Gly Glu Ser Met Ala Ile Ile Ser Ala Pro Gly Ala Arg Gly
1085                1090                1095 gcg cac gtg atc aac aac ggt ggt gtg gaa gtg gac tgg atg ggt           3454
Ala His Val Ile Asn Asn Gly Gly Val Glu Val Asp Trp Met Gly
1100                1105                1110 aat gcg gtc gta cct tac ctt act ccg tac cgt gaa acg gaa gtc           3499
Asn Ala Val Val Pro Tyr Leu Thr Pro Tyr Arg Glu Thr Glu Val
1115                1120                1125 tca ctg cga agc gac agc ctg aac aac cag gtt gac ctg gat acc           3544
Ser Leu Arg Ser Asp Ser Leu Asn Asn Gln Val Asp Leu Asp Thr
1130                1135                1140 gcc tcc gtc aac gta gtg ccg aca cgc ggc gcg att gtt cgt gcc           3589
Ala Ser Val Asn Val Val Pro Thr Arg Gly Ala Ile Val Arg Ala
1145                1150                1155 cgc ttc gat acc cga gtg ggc tat cgt gtg ctg atg aat ctg acg           3634
Arg Phe Asp Thr Arg Val Gly Tyr Arg Val Leu Met Asn Leu Thr
1160                1165                1170 cag gcc aat ggc aaa gcg gtg ccg ttt ggt gct acc gcc acg ctg           3679
Gln Ala Asn Gly Lys Ala Val Pro Phe Gly Ala Thr Ala Thr Leu
1175                1180                1185 ctg gat acc aca aaa gag tcc agc agc att gtg ggt gaa gac ggt           3724
Leu Asp Thr Thr Lys Glu Ser Ser Ser Ile Val Gly Glu Asp Gly
1190                1195                1200
```

```
cag ctt tat atc agc ggg atg ccg gag aaa ggt gcc ctt cag gtg         3769
Gln Leu Tyr Ile Ser Gly Met Pro Glu Lys Gly Ala Leu Gln Val
1205                1210                1215 aac tgg ggt aaa gac cag gca cag caa tgc cgc gtg gcg ttt acg         3814
Asn Trp Gly Lys Asp Gln Ala Gln Gln Cys Arg Val Ala Phe Thr
1220                1225                1230 ctg ccg gaa caa cag gat aat acc ggc gtg gtg atg gcg aat gcc         3859
Leu Pro Glu Gln Gln Asp Asn Thr Gly Val Val Met Ala Asn Ala
1235                1240                1245 gtc tgc cgg taacagggaa ggaaacgatt atgttgaaaa agttgataat             3908
Val Cys Arg
1250 gtttacgggc tgttgggcg gtcggtgct gttttcgggg caggcgctgg cagcggcaga     3968 ttttggacca tgtactcctg aaggtggaac acatatcttc agtgccacca taaataaaac  4028 agtttcagat acgtcaaaga acacaacggg tgcgaccttc gtagatttcg atagctggaa  4088 tttaggtgga acctatgcga tgtcctgtga atgccctgat gatacctctc ttataaatga  4148 caccttattt aaggctgtgg ttcctctggc ctttgttacg aatatagaga gtcgctccta  4208 ttaccagatc aataataata ttgccattgc gagcgatgta ctgatttcgg ggggacgagg  4268 agaatacgtt aacacaccgt aaggtaacct gacaaacaac cgctctcagt gttcgcaaaa  4328 tgcaagtagt aaagatgcaa tatggacatc cggtggcaaa ggtcacttat cgctctatat  4388 tctccatccg tttgtgggtg aaagtattat acctagcacc aaaata atg gac ctt     4443
                                                    Met Asp Leu
                                                          1255 ttt gtg aca aag aaa ccc agt gta tat ggc agt ata cct gcg tcg         4488
Phe Val Thr Lys Lys Pro Ser Val Tyr Gly Ser Ile Pro Ala Ser
                1260                1265                1270 tct gta tat atc agt ggt tca att acg gta cct cag ggc tgt gaa         4533
Ser Val Tyr Ile Ser Gly Ser Ile Thr Val Pro Gln Gly Cys Glu
                1275                1280                1285 ctc tcc agc ggc agc acg ctg gaa att ccg ttt ggg gaa ttt aag         4578
Leu Ser Ser Gly Ser Thr Leu Glu Ile Pro Phe Gly Glu Phe Lys
                1290                1295                1300 gcc act gat ttt aaa gat cgc aaa gga caa gtt gca aag aac gcc         4623
Ala Thr Asp Phe Lys Asp Arg Lys Gly Gln Val Ala Lys Asn Ala
                1305                1310                1315 acg aaa ttc acc aaa gag ctg cag ttt aaa tgc acc aat att tcc         4668
Thr Lys Phe Thr Lys Glu Leu Gln Phe Lys Cys Thr Asn Ile Ser
                1320                1325                1330 gat ggc gta aag atc ttc ctg cgt att gag gga atg cca aac gct         4713
Asp Gly Val Lys Ile Phe Leu Arg Ile Glu Gly Met Pro Asn Ala
                1335                1340                1345 aat gat tcg aat gcc atc gac atg ggc aac ccg gat atc ggt gcc         4758
Asn Asp Ser Asn Ala Ile Asp Met Gly Asn Pro Asp Ile Gly Ala
                1350                1355                1360 gtc att gag ggc gct aac ggt aaa att ttg gtg cca aat gac gcc         4803
Val Ile Glu Gly Ala Asn Gly Lys Ile Leu Val Pro Asn Asp Ala
                1365                1370                1375 agt gtt aat cag gag ctg agc gta tcg ggt ctt gtt gac gac acg         4848
Ser Val Asn Gln Glu Leu Ser Val Ser Gly Leu Val Asp Asp Thr
                1380                1385                1390 cac cgt acc gcc tca acg acc att tcg gct tac cct atc agt acc         4893
His Arg Thr Ala Ser Thr Thr Ile Ser Ala Tyr Pro Ile Ser Thr
                1395                1400                1405 acc ggc aaa ttg ccg gcc gcc ggg gat ttc gag gga att gcc acc         4938
Thr Gly Lys Leu Pro Ala Ala Gly Asp Phe Glu Gly Ile Ala Thr
                1410                1415                1420
```

| | | | | | | | | | | | |
|---|---|---|---|---|---|---|---|---|---|---|---|
| atg | cgt | att | gat | gtg | gag | taagcagg | atg | aaa | aac | ctt | cat gct ttg |
| Met | Arg | Ile | Asp | Val | Glu | | Met | Lys | Asn | Leu | His Ala Leu |
| | | | 1425 | | | | | 1430 | | | |

```
atg cgt att gat gtg gag taagcagg atg aaa aac ctt cat gct ttg     4985
Met Arg Ile Asp Val Glu          Met Lys Asn Leu His Ala Leu
                1425                     1430 atg cca gcg tgt tta ctg ctt acc gct tcc gcg atg gcg gca ccg     5030
Met Pro Ala Cys Leu Leu Leu Thr Ala Ser Ala Met Ala Ala Pro
    1435            1440                1445 tcg aat atc ggt tct gct ggt gat atc cac ttt acc att act att     5075
Ser Asn Ile Gly Ser Ala Gly Asp Ile His Phe Thr Ile Thr Ile
1450            1455                1460 aag gcg gct acc tgt gaa ctg gaa aac gac agt atc gac gtc aat     5120
Lys Ala Ala Thr Cys Glu Leu Glu Asn Asp Ser Ile Asp Val Asn
    1465            1470                1475 atg gag acc gtg gtg ctt cag cgc ccg gta aaa gtg ggt aaa gag     5165
Met Glu Thr Val Val Leu Gln Arg Pro Val Lys Val Gly Lys Glu
1480            1485                1490 ctg aac cag aaa aac ttt agc atc ggc tta aaa gat tgc gcg tat     5210
Leu Asn Gln Lys Asn Phe Ser Ile Gly Leu Lys Asp Cys Ala Tyr
    1495            1500                1505 gcc aca aag gcc agc gtt acg atg gac ggt tct ccg gac ccg act     5255
Ala Thr Lys Ala Ser Val Thr Met Asp Gly Ser Pro Asp Pro Thr
1510            1515                1520 gac ccc tcg ctt ttt gcc ctg gat agc ggc ggc gcg acg ggc gtg     5300
Asp Pro Ser Leu Phe Ala Leu Asp Ser Gly Gly Ala Thr Gly Val
    1525            1530                1535 gcg tta aaa att aaa aca tct ggt ggg gag caa caa tac ccc tcc     5345
Ala Leu Lys Ile Lys Thr Ser Gly Gly Glu Gln Gln Tyr Pro Ser
1540            1545                1550 agt acc gac tct acg cct gtc gaa cac act gtc tgg ttt gat ggt     5390
Ser Thr Asp Ser Thr Pro Val Glu His Thr Val Trp Phe Asp Gly
    1555            1560                1565 acg aac aag ctg aac tat atc gcc agc tat gtg cct gtt aag ccg     5435
Thr Asn Lys Leu Asn Tyr Ile Ala Ser Tyr Val Pro Val Lys Pro
1570            1575                1580 gat gcc acc gtt ggc aca gcg aat gcg acg gtg aat ttt agc gtc     5480
Asp Ala Thr Val Gly Thr Ala Asn Ala Thr Val Asn Phe Ser Val
    1585            1590                1595 aca tac gaa taatcactga gggccagttc gctggccctt ttccattttt         5529
Thr Tyr Glu
        1600 agtgattttt tgtaaaaatc ttctccgatc acactctccg ttgccacttt ccctctgct    5589 tgtggtctac ttaaccgtgc tctcgagcgc                                    5619
```

<210> SEQ ID NO 14
<211> LENGTH: 494
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
gccggatccc gcagtgataa cagctcttgt ggcggaagta gggtgctaac cttctgcgtt     60
atctttgcgc tgttaattat ctcgctggca ctttccacca ctattcgcca gccgcagcgg    120
gagggggtta gcgaagcgtc tgcgtaacac atgcaacacc aggcgtacag cgcacccatt    180
tggtgccctt tttttttattt agcacaaata cctaatcaat tgtagttaaa aaacgtcta    240 ataaataagg aagacattta acttattat gaataggaag aaataatata ttaattat     300 taatttattc ttaataaaaa attacattta tgtacattcc atttgtaata tattgatttc    360
```

```
tattcttttt aagattaact aacaattatt tttatatata ctaattatag tatccaatac    420
ccacctctat acactccatt tcctcacaga atgcagataa tcctaaggat gcgttctgtt    480
atctaccgtc ataa                                                      494
```

<210> SEQ ID NO 15
<211> LENGTH: 6113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (495)..(1028)
<220> FEATURE:
<221> NAME/KEY: CDS
<222> LOCATION: (1116)..(1811)
<220> FEATURE:
<221> NAME/KEY: CDS
<222> LOCATION: (1837)..(4362)
<220> FEATURE:
<221> NAME/KEY: CDS
<222> LOCATION: (4929)..(5450)
<220> FEATURE:
<221> NAME/KEY: CDS
<222> LOCATION: (5459)..(5983)

<400> SEQUENCE: 15

```
gccggatccc gcagtgataa cagctcttgt ggcggaagta gggtgctaac cttctgcgtt    60
atctttgcgc tgttaattat ctcgctggca cttccacca ctattcgcca gccgcagcgg    120 gaggggggtta gcgaagcgtc tgcgtaacac atgcaacacc aggcgtacag cgcacccatt    180
tggtgccctt ttttttattt agcacaaata cctaatcaat tgtagttaaa aaaacgtcta    240
ataaataagg aagacattta acttatttat gaataggaag aaataatata ttaattatat    300
taatttattc ttaataaaaa attacattta tgtacattcc atttgtaata tattgatttc    360
tattcttttt aagattaact aacaattatt tttatatata ctaattatag tatccaatac    420
ccacctctat acactccatt tcctcacaga atgcagataa tcctaaggat gcgttctgtt    480
atctaccgtc ataa atg gag ttt tta atg aaa aag gtt gtt ttt gct ctg    530
              Met Glu Phe Leu Met Lys Lys Val Val Phe Ala Leu
                1               5                   10 tct gct ctc gct gta gtt tcc act tct gct ttc gct gct gaa tct ggt    578
Ser Ala Leu Ala Val Val Ser Thr Ser Ala Phe Ala Ala Glu Ser Gly
        15                  20                  25 gac ggc acc att aaa ttc acc ggt gaa atc gtt gac gcg cca tgc gtc    626
Asp Gly Thr Ile Lys Phe Thr Gly Glu Ile Val Asp Ala Pro Cys Val
    30                  35                  40 gtt tct act gac tcc cag aac cag gaa gtt gtg ctg ggt cag gtt aag    674
Val Ser Thr Asp Ser Gln Asn Gln Glu Val Val Leu Gly Gln Val Lys
45                  50                  55                  60 aaa aat atc ttc aaa gcc att ggc gac aag tct tct tct aag cct ttc    722
Lys Asn Ile Phe Lys Ala Ile Gly Asp Lys Ser Ser Ser Lys Pro Phe
                65                  70                  75 cag atc aaa ctg gaa gac tgt gac atc acc tct aat acc aaa gtt aac    770
Gln Ile Lys Leu Glu Asp Cys Asp Ile Thr Ser Asn Thr Lys Val Asn
            80                  85                  90 gta agc ttc aat ggc gtt ggt gat aca gac gat gcg aca ctg gtt tct    818
Val Ser Phe Asn Gly Val Gly Asp Thr Asp Asp Ala Thr Leu Val Ser
        95                  100                 105 gtt aac act gaa gca ggt gcg gca act ggc gtg ggc atc ggt atc tac    866
Val Asn Thr Glu Ala Gly Ala Ala Thr Gly Val Gly Ile Gly Ile Tyr
    110                 115                 120
```

```
gac aac gct aac aag ctt gtt gaa atg aac acc ggt aaa tcc acc act    914
Asp Asn Ala Asn Lys Leu Val Glu Met Asn Thr Gly Lys Ser Thr Thr
125                 130                 135                 140 acg ttg gct gct ggt cag acc gtg ctg tac tac acc gct aac tac gtt    962
Thr Leu Ala Ala Gly Gln Thr Val Leu Tyr Tyr Thr Ala Asn Tyr Val
            145                 150                 155 gca aca aaa gat act gta acc act ggt tac ggt aac gca gaa gtg gac   1010
Ala Thr Lys Asp Thr Val Thr Thr Gly Tyr Gly Asn Ala Glu Val Asp
                160                 165                 170 ttc aac ctg tcc tac gaa taatcgaatt ttcgttaata cagacaatca          1058
Phe Asn Leu Ser Tyr Glu
                175 taatggcaac ggaaatcccg ttgccatttt ttccagcgga ggctcaggaa gagaatc    1115 atg aac cgc tca cgt ttg ata tct tgc aca gca ctg gtg ctg gcg ttg   1163
Met Asn Arg Ser Arg Leu Ile Ser Cys Thr Ala Leu Val Leu Ala Leu
            180                 185                 190 att gct caa aac agt ttt gcc gga ggc gtg gca tta agc agc acg cgt   1211
Ile Ala Gln Asn Ser Phe Ala Gly Gly Val Ala Leu Ser Ser Thr Arg
195                 200                 205                 210 gtt att tat gac ggt agt aga aag gaa gct tct ctt acg gta aat aat   1259
Val Ile Tyr Asp Gly Ser Arg Lys Glu Ala Ser Leu Thr Val Asn Asn
                215                 220                 225 aaa agc acc acg gat gaa ttt ctc att cag tca tgg att gat gat gct   1307
Lys Ser Thr Thr Asp Glu Phe Leu Ile Gln Ser Trp Ile Asp Asp Ala
            230                 235                 240 aac ggt aat aaa aag acg ccc ttt atc atc act cca ccg tta ttt aaa   1355
Asn Gly Asn Lys Lys Thr Pro Phe Ile Ile Thr Pro Pro Leu Phe Lys
245                 250                 255 tta agc ccg act aaa aat aac gtt tta cgt att gtt aat acg acg aac   1403
Leu Ser Pro Thr Lys Asn Asn Val Leu Arg Ile Val Asn Thr Thr Asn
260                 265                 270 acg tta ccg cag gat cgc gag tcc gtt tat tgg att aac gta aaa gct   1451
Thr Leu Pro Gln Asp Arg Glu Ser Val Tyr Trp Ile Asn Val Lys Ala
275                 280                 285                 290 att cct gcc aaa agt gaa gac gcg gaa gct aaa aac gta ctg cag atc   1499
Ile Pro Ala Lys Ser Glu Asp Ala Glu Ala Lys Asn Val Leu Gln Ile
                295                 300                 305 gcc gta cgt acc cgc tta aaa ctg ttc tat cgc ccg gcg ggc ctg aaa   1547
Ala Val Arg Thr Arg Leu Lys Leu Phe Tyr Arg Pro Ala Gly Leu Lys
            310                 315                 320 ggc aat agc atg gac ggc tgg aac aaa ctg cag ttc acc agc gca ggg   1595
Gly Asn Ser Met Asp Gly Trp Asn Lys Leu Gln Phe Thr Ser Ala Gly
                325                 330                 335 gct aac cag atc aaa gtg gaa aac cca tct gcc ttt aac ctg acg ttt   1643
Ala Asn Gln Ile Lys Val Glu Asn Pro Ser Ala Phe Asn Leu Thr Phe
            340                 345                 350 aat aaa ttt tat gcc aac ggc cgt gat att gaa aaa acg gga atg gtt   1691
Asn Lys Phe Tyr Ala Asn Gly Arg Asp Ile Glu Lys Thr Gly Met Val
355                 360                 365                 370 ccg gca aaa ggc tca ttg aat att gaa ctg cca gcc ggc acc ggc aag   1739
Pro Ala Lys Gly Ser Leu Asn Ile Glu Leu Pro Ala Gly Thr Gly Lys
                375                 380                 385 gta agc gaa gtt aaa tac aac att att aat gac ttt ggc act gct ggc   1787
Val Ser Glu Val Lys Tyr Asn Ile Ile Asn Asp Phe Gly Thr Ala Gly
                390                 395                 400 gac atg ttg aca cag cgc gtt aac taacacgttt taaaggatta ttact atg   1839
Asp Met Leu Thr Gln Arg Val Asn                                  Met
            405                 410
```

-continued

| | | |
|---|---|---|
| aca tgg acg cat ctt cct ctg ggc aat aag acc tcg cgt ttc acg cag<br>Thr Trp Thr His Leu Pro Leu Gly Asn Lys Thr Ser Arg Phe Thr Gln<br>                          415                        420                        425 | 1887 |
| tct gcg ctt gcg ctg atg ata gcg ggt acg ctc ccc gcg tat gcg gga<br>Ser Ala Leu Ala Leu Met Ile Ala Gly Thr Leu Pro Ala Tyr Ala Gly<br>                          430                        435                        440 | 1935 |
| aca ttt aac ccg cgc ttt ctg gag gat gtg ccg ggt att gat cag cac<br>Thr Phe Asn Pro Arg Phe Leu Glu Asp Val Pro Gly Ile Asp Gln His<br>445                        450                        455 | 1983 |
| gtt gac ctt tca atg tat gaa tcc aat aaa gct gaa cac ctg cca ggt<br>Val Asp Leu Ser Met Tyr Glu Ser Asn Lys Ala Glu His Leu Pro Gly<br>460                        465                        470                        475 | 2031 |
| aaa tac cgc gtc tcg gtg gtg gtc aac gaa aaa aaa atg gag tct cgc<br>Lys Tyr Arg Val Ser Val Val Val Asn Glu Lys Lys Met Glu Ser Arg<br>                                    480                        485                        490 | 2079 |
| acc ctg gag ttt aag gca gcg aca gag gcg cag cgc gca aaa atg ggt<br>Thr Leu Glu Phe Lys Ala Ala Thr Glu Ala Gln Arg Ala Lys Met Gly<br>                          495                        500                        505 | 2127 |
| gaa tcc ctg gtg ccg tgc tta agt cgc gtg cag ctt gaa gat atg ggc<br>Glu Ser Leu Val Pro Cys Leu Ser Arg Val Gln Leu Glu Asp Met Gly<br>                        510                        515                        520 | 2175 |
| gtg cgt att gat agc ttc ccg gcg ctg aaa atg gcc ccg cct gaa gcc<br>Val Arg Ile Asp Ser Phe Pro Ala Leu Lys Met Ala Pro Pro Glu Ala<br>525                        530                        535 | 2223 |
| tgt gtt gct ttt gac gac att att ccc cag gcc gcc agc cat ttc gac<br>Cys Val Ala Phe Asp Asp Ile Ile Pro Gln Ala Ala Ser His Phe Asp<br>540                        545                        550                        555 | 2271 |
| ttt gca gac cag acc ctg atc atg agc ttc ccg cag gct gcg atg aag<br>Phe Ala Asp Gln Thr Leu Ile Met Ser Phe Pro Gln Ala Ala Met Lys<br>                        560                        565                        570 | 2319 |
| cag aca gcg cgc ggt acg gtg cca gaa tcg cag tgg gac gaa ggg gtg<br>Gln Thr Ala Arg Gly Thr Val Pro Glu Ser Gln Trp Asp Glu Gly Val<br>                          575                        580                        585 | 2367 |
| aat gcc ctg ctg gtg gat tat aac ttt tcc ggc agc aac gcc agc tat<br>Asn Ala Leu Leu Val Asp Tyr Asn Phe Ser Gly Ser Asn Ala Ser Tyr<br>                        590                        595                        600 | 2415 |
| gac gca cac gac agt gaa acc agc tac aac agc gac agc tac tat ctg<br>Asp Ala His Asp Ser Glu Thr Ser Tyr Asn Ser Asp Ser Tyr Tyr Leu<br>605                        610                        615 | 2463 |
| aat ctg cgc agc ggt atg aac ctg ggg gca tgg cgg tta cgt aac tat<br>Asn Leu Arg Ser Gly Met Asn Leu Gly Ala Trp Arg Leu Arg Asn Tyr<br>620                        625                        630                        635 | 2511 |
| agc acc tgg acg cga aac gac ggt aac aac aca tgg gat aac att ggc<br>Ser Thr Trp Thr Arg Asn Asp Gly Asn Asn Thr Trp Asp Asn Ile Gly<br>                        640                        645                        650 | 2559 |
| aca tcc tta agc cgt gcc att gta ccg ctg aaa tca cag ctg acg ttg<br>Thr Ser Leu Ser Arg Ala Ile Val Pro Leu Lys Ser Gln Leu Thr Leu<br>                        655                        660                        665 | 2607 |
| ggg gat acc tcc act gcc ggt gat att ttt gac agc gtt cag atg cgc<br>Gly Asp Thr Ser Thr Ala Gly Asp Ile Phe Asp Ser Val Gln Met Arg<br>                        670                        675                        680 | 2655 |
| ggt gtg cag tta act tcc gac gaa gag atg ctg cct gac agc cag cgc<br>Gly Val Gln Leu Thr Ser Asp Glu Glu Met Leu Pro Asp Ser Gln Arg<br>685                        690                        695 | 2703 |
| ggg ttt gcg ccc gtc atc cgg ggt att gcc aaa agt aac gcc gaa gtt<br>Gly Phe Ala Pro Val Ile Arg Gly Ile Ala Lys Ser Asn Ala Glu Val<br>700                        705                        710                        715 | 2751 |

-continued

| | |
|---|---|
| acc gtt gag cag aac aac tac gtt att tac cgt acg ttt gtt cag ccg<br>Thr Val Glu Gln Asn Asn Tyr Val Ile Tyr Arg Thr Phe Val Gln Pro<br>                    720                     725                     730 | 2799 |
| ggt gcg ttt gaa att aac gac ctg tat cca acc tca aac agc ggc gac<br>Gly Ala Phe Glu Ile Asn Asp Leu Tyr Pro Thr Ser Asn Ser Gly Asp<br>        735                     740                     745 | 2847 |
| ctg acg gtc acc att aaa gaa tcg gac ggc agt gag cag aag ttc gtt<br>Leu Thr Val Thr Ile Lys Glu Ser Asp Gly Ser Glu Gln Lys Phe Val<br>                    750                     755                     760 | 2895 |
| cag ccg ttc tcc tcg gtg gcg ctc ctc cag cgt gaa ggc cat ctc aaa<br>Gln Pro Phe Ser Ser Val Ala Leu Leu Gln Arg Glu Gly His Leu Lys<br>        765                     770                     775 | 2943 |
| tac agc ctt tcc gcc ggg gaa tac cgt gcc ggg aac tat aac agc gcc<br>Tyr Ser Leu Ser Ala Gly Glu Tyr Arg Ala Gly Asn Tyr Asn Ser Ala<br>780                     785                     790                     795 | 2991 |
| gag ccg aaa ttc ggg cag ctt gat gcc atg tac ggc ctg ccg tat ggc<br>Glu Pro Lys Phe Gly Gln Leu Asp Ala Met Tyr Gly Leu Pro Tyr Gly<br>                    800                     805                     810 | 3039 |
| ttt acc gtt tac ggt ggt gcg atc ttc tct gac gac tat tac tcg ctg<br>Phe Thr Val Tyr Gly Gly Ala Ile Phe Ser Asp Asp Tyr Tyr Ser Leu<br>        815                     820                     825 | 3087 |
| gcg gga gga tta ggt aaa aac ttc ggt tat atc ggc gcg atc tcc atc<br>Ala Gly Gly Leu Gly Lys Asn Phe Gly Tyr Ile Gly Ala Ile Ser Ile<br>                    830                     835                     840 | 3135 |
| gat gta acc cag gca aaa agc aag ctg gca aat gag gag aat tcg gaa<br>Asp Val Thr Gln Ala Lys Ser Lys Leu Ala Asn Glu Glu Asn Ser Glu<br>        845                     850                     855 | 3183 |
| ggt cag tct tat cgt ttc ctc tac tcc aag agc ttt aac agc ggt aca<br>Gly Gln Ser Tyr Arg Phe Leu Tyr Ser Lys Ser Phe Asn Ser Gly Thr<br>860                     865                     870                     875 | 3231 |
| gat ttc cgt ctg ctg ggt tac aag tat tcg acc agc ggc tat tac acc<br>Asp Phe Arg Leu Leu Gly Tyr Lys Tyr Ser Thr Ser Gly Tyr Tyr Thr<br>                    880                     885                     890 | 3279 |
| ttc cag gaa gcg acg gat gtg cgc agc gat gcg gac agc tct tat agc<br>Phe Gln Glu Ala Thr Asp Val Arg Ser Asp Ala Asp Ser Ser Tyr Ser<br>        895                     900                     905 | 3327 |
| cag tac cac aaa cgt agt cag att cag ggc aac gtg acg cag caa ctg<br>Gln Tyr His Lys Arg Ser Gln Ile Gln Gly Asn Val Thr Gln Gln Leu<br>                    910                     915                     920 | 3375 |
| ggc gcc tgg ggc tcg gtc tat ttt aac gtc acg cag cag gac tac tgg<br>Gly Ala Trp Gly Ser Val Tyr Phe Asn Val Thr Gln Gln Asp Tyr Trp<br>        925                     930                     935 | 3423 |
| aac gat gaa ggt aaa cag cgt tcg ctg aat gcc ggt tat aac ggc cgt<br>Asn Asp Glu Gly Lys Gln Arg Ser Leu Asn Ala Gly Tyr Asn Gly Arg<br>940                     945                     950                     955 | 3471 |
| att ggc cgc gtg aac tac agc gtt gct tac acc tgg acg aaa agc ccg<br>Ile Gly Arg Val Asn Tyr Ser Val Ala Tyr Thr Trp Thr Lys Ser Pro<br>                    960                     965                     970 | 3519 |
| gag tgg gat gag agc gat cgt tta ctg tca ttc tcc atg tcg att cca<br>Glu Trp Asp Glu Ser Asp Arg Leu Leu Ser Phe Ser Met Ser Ile Pro<br>        975                     980                     985 | 3567 |
| ctg gga cgc gtg tgg agt aac tac cac ctc acg acc gat cag cat ggc<br>Leu Gly Arg Val Trp Ser Asn Tyr His Leu Thr Thr Asp Gln His Gly<br>                    990                     995                     1000 | 3615 |
| cga acc aac cag cag tta ggg gtg agc ggc acc gcg ctg gaa gac<br>Arg Thr Asn Gln Gln Leu Gly Val Ser Gly Thr Ala Leu Glu Asp<br>        1005                    1010                    1015 | 3660 |
| cac aac ctg aac tat agt gtg cag gaa ggc tac ggc agc aac ggc<br>His Asn Leu Asn Tyr Ser Val Gln Glu Gly Tyr Gly Ser Asn Gly<br>        1020                    1025                    1030 | 3705 |

-continued

| | | | | | | | | | | | | | | |
|---|---|---|---|---|---|---|---|---|---|---|---|---|---|---|
| gtg | ggt | aac | agc | ggc | agc | gtg | aac | ctg | gat | tac | cag | ggc | ggc | gtg | 3750 |
| Val | Gly | Asn | Ser | Gly | Ser | Val | Asn | Leu | Asp | Tyr | Gln | Gly | Gly | Val | |
| | 1035 | | | | 1040 | | | | | 1045 | | | | | |
| ggt | agc | gcc | agc | ctg | ggt | tac | aac | tac | aac | cgt | gac | ggc | cag | cag | 3795 |
| Gly | Ser | Ala | Ser | Leu | Gly | Tyr | Asn | Tyr | Asn | Arg | Asp | Gly | Gln | Gln | |
| | 1050 | | | | 1055 | | | | | 1060 | | | | | |
| gtg | aac | tac | ggt | ttg | cgc | ggc | ggt | gtg | ata | gcc | cat | agc | gaa | ggt | 3840 |
| Val | Asn | Tyr | Gly | Leu | Arg | Gly | Gly | Val | Ile | Ala | His | Ser | Glu | Gly | |
| 1065 | | | | | 1070 | | | | | 1075 | | | | | |
| atc | act | ctt | tct | caa | ccg | ctg | ggt | gaa | tcc | atg | gcc | att | atc | tcc | 3885 |
| Ile | Thr | Leu | Ser | Gln | Pro | Leu | Gly | Glu | Ser | Met | Ala | Ile | Ile | Ser | |
| 1080 | | | | | 1085 | | | | | 1090 | | | | | |
| gcg | ccg | ggc | gcg | cgc | ggc | gcg | cac | gtg | atc | aac | aac | ggt | ggt | gtg | 3930 |
| Ala | Pro | Gly | Ala | Arg | Gly | Ala | His | Val | Ile | Asn | Asn | Gly | Gly | Val | |
| | 1095 | | | | 1100 | | | | | 1105 | | | | | |
| gaa | gtg | gac | tgg | atg | ggt | aat | gcg | gtc | gta | cct | tac | ctt | act | ccg | 3975 |
| Glu | Val | Asp | Trp | Met | Gly | Asn | Ala | Val | Val | Pro | Tyr | Leu | Thr | Pro | |
| | 1110 | | | | 1115 | | | | | 1120 | | | | | |
| tac | cgt | gaa | acg | gaa | gtc | tca | ctg | cga | agc | gac | agc | ctg | aac | aac | 4020 |
| Tyr | Arg | Glu | Thr | Glu | Val | Ser | Leu | Arg | Ser | Asp | Ser | Leu | Asn | Asn | |
| | 1125 | | | | 1130 | | | | | 1135 | | | | | |
| cag | gtt | gac | ctg | gat | acc | gcc | tcc | gtc | aac | gta | gtg | ccg | aca | cgc | 4065 |
| Gln | Val | Asp | Leu | Asp | Thr | Ala | Ser | Val | Asn | Val | Val | Pro | Thr | Arg | |
| | 1140 | | | | 1145 | | | | | 1150 | | | | | |
| ggc | gcg | att | gtt | cgt | gcc | cgc | ttc | gat | acc | cga | gtg | ggc | tat | cgt | 4110 |
| Gly | Ala | Ile | Val | Arg | Ala | Arg | Phe | Asp | Thr | Arg | Val | Gly | Tyr | Arg | |
| | 1155 | | | | 1160 | | | | | 1165 | | | | | |
| gtg | ctg | atg | aat | ctg | acg | cag | gcc | aat | ggc | aaa | gcg | gtg | ccg | ttt | 4155 |
| Val | Leu | Met | Asn | Leu | Thr | Gln | Ala | Asn | Gly | Lys | Ala | Val | Pro | Phe | |
| | 1170 | | | | 1175 | | | | | 1180 | | | | | |
| ggt | gct | acc | gcc | acg | ctg | ctg | gat | acc | aca | aaa | gag | tcc | agc | agc | 4200 |
| Gly | Ala | Thr | Ala | Thr | Leu | Leu | Asp | Thr | Thr | Lys | Glu | Ser | Ser | Ser | |
| | 1185 | | | | 1190 | | | | | 1195 | | | | | |
| att | gtg | ggt | gaa | gac | ggt | cag | ctt | tat | atc | agc | ggg | atg | ccg | gag | 4245 |
| Ile | Val | Gly | Glu | Asp | Gly | Gln | Leu | Tyr | Ile | Ser | Gly | Met | Pro | Glu | |
| | 1200 | | | | 1205 | | | | | 1210 | | | | | |
| aaa | ggt | gcc | ctt | cag | gtg | aac | tgg | ggt | aaa | gac | cag | gca | cag | caa | 4290 |
| Lys | Gly | Ala | Leu | Gln | Val | Asn | Trp | Gly | Lys | Asp | Gln | Ala | Gln | Gln | |
| | 1215 | | | | 1220 | | | | | 1225 | | | | | |
| tgc | cgc | gtg | gcg | ttt | acg | ctg | ccg | gaa | caa | cag | gat | aat | acc | ggc | 4335 |
| Cys | Arg | Val | Ala | Phe | Thr | Leu | Pro | Glu | Gln | Gln | Asp | Asn | Thr | Gly | |
| | 1230 | | | | 1235 | | | | | 1240 | | | | | |
| gtg | gtg | atg | gcg | aat | gcc | gtc | tgc | cgg | taacagggaa | | | ggaaacgatt | | | 4382 |
| Val | Val | Met | Ala | Asn | Ala | Val | Cys | Arg | | | | | | | |
| | 1245 | | | | 1250 | | | | | | | | | | |

| | |
|---|---|
| atgttgaaaa agttgataat gtttacgggc ctgttgggcg ggtcggtgct gttttcgggg | 4442 |
| caggcgctgg cagcggcaga ttttggacca tgtactcctg aaggtggaac acatatcttc | 4502 |
| agtgccacca taaataaaac agtttcagat acgtcaaaga acacaacggg tgcgaccttc | 4562 |
| gtagatttcg atagctggaa tttaggtgga acctatgcga tgtcctgtga atgccctgat | 4622 |
| gatacctctc ttataaatga caccttattt aaggctgtgg ttcctctggc ctttgttacg | 4682 |
| aatatagaga gtcgctccta ttaccagatc aataataata ttgccattgc gagcgatgta | 4742 |
| ctgatttcgg ggggacgagg agaatacgtt aacacaccgt aaggtaacct gacaaacaac | 4802 |
| cgctctcagt gttcgcaaaa tgcaagtagt aaagatgcaa tatggacatc cggtggcaaa | 4862 |
| ggtcacttat cgctctatat tctccatccg tttgtgggtg aaagtattat acctagcacc | 4922 |

```
                                      -continued aaaata atg gac ctt ttt gtg aca aag aaa ccc agt gta tat ggc agt      4970
       Met Asp Leu Phe Val Thr Lys Lys Pro Ser Val Tyr Gly Ser
           1255            1260            1265 ata cct gcg tcg tct gta tat atc agt ggt tca att acg gta cct         5015
Ile Pro Ala Ser Ser Val Tyr Ile Ser Gly Ser Ile Thr Val Pro
       1270            1275            1280 cag ggc tgt gaa ctc tcc agc ggc agc acg ctg gaa att ccg ttt         5060
Gln Gly Cys Glu Leu Ser Ser Gly Ser Thr Leu Glu Ile Pro Phe
       1285            1290            1295 ggg gaa ttt aag gcc act gat ttt aaa gat cgc aaa gga caa gtt         5105
Gly Glu Phe Lys Ala Thr Asp Phe Lys Asp Arg Lys Gly Gln Val
       1300            1305            1310 gca aag aac gcc acg aaa ttc acc aaa gag ctg cag ttt aaa tgc         5150
Ala Lys Asn Ala Thr Lys Phe Thr Lys Glu Leu Gln Phe Lys Cys
       1315            1320            1325 acc aat att tcc gat ggc gta aag atc ttc ctg cgt att gag gga         5195
Thr Asn Ile Ser Asp Gly Val Lys Ile Phe Leu Arg Ile Glu Gly
       1330            1335            1340 atg cca aac gct aat gat tcg aat gcc atc gac atg ggc aac ccg         5240
Met Pro Asn Ala Asn Asp Ser Asn Ala Ile Asp Met Gly Asn Pro
       1345            1350            1355 gat atc ggt gcc gtc att gag ggc gct aac ggt aaa att ttg gtg         5285
Asp Ile Gly Ala Val Ile Glu Gly Ala Asn Gly Lys Ile Leu Val
       1360            1365            1370 cca aat gac gcc agt gtt aat cag gag ctg agc gta tcg ggt ctt         5330
Pro Asn Asp Ala Ser Val Asn Gln Glu Leu Ser Val Ser Gly Leu
       1375            1380            1385 gtt gac gac acg cac cgt acc gcc tca acg acc att tcg gct tac         5375
Val Asp Asp Thr His Arg Thr Ala Ser Thr Thr Ile Ser Ala Tyr
       1390            1395            1400 cct atc agt acc acc ggc aaa ttg ccg gcc gcc ggg gat ttc gag         5420
Pro Ile Ser Thr Thr Gly Lys Leu Pro Ala Ala Gly Asp Phe Glu
       1405            1410            1415 gga att gcc acc atg cgt att gat gtg gag taagcagg atg aaa aac        5467
Gly Ile Ala Thr Met Arg Ile Asp Val Glu         Met Lys Asn
       1420            1425 ctt cat gct ttg atg cca gcg tgt tta ctg ctt acc gct tcc gcg         5512
Leu His Ala Leu Met Pro Ala Cys Leu Leu Leu Thr Ala Ser Ala
1430            1435            1440 atg gcg gca ccg tcg aat atc ggt tct gct ggt gat atc cac ttt         5557
Met Ala Ala Pro Ser Asn Ile Gly Ser Ala Gly Asp Ile His Phe
1445            1450            1455 acc att act att aag gcg gct acc tgt gaa ctg gaa aac gac agt         5602
Thr Ile Thr Ile Lys Ala Ala Thr Cys Glu Leu Glu Asn Asp Ser
1460            1465            1470 atc gac gtc aat atg gag acc gtg gtg ctt cag cgc ccg gta aaa         5647
Ile Asp Val Asn Met Glu Thr Val Val Leu Gln Arg Pro Val Lys
1475            1480            1485 gtg ggt aaa gag ctg aac cag aaa aac ttt agc atc ggc tta aaa         5692
Val Gly Lys Glu Leu Asn Gln Lys Asn Phe Ser Ile Gly Leu Lys
1490            1495            1500 gat tgc gcg tat gcc aca aag gcc agc gtt acg atg gac ggt tct         5737
Asp Cys Ala Tyr Ala Thr Lys Ala Ser Val Thr Met Asp Gly Ser
1505            1510            1515 ccg gac ccg act gac ccc tcg ctt ttt gcc ctg gat agc ggc ggc         5782
Pro Asp Pro Thr Asp Pro Ser Leu Phe Ala Leu Asp Ser Gly Gly
1520            1525            1530 gcg acg ggc gtg gcg tta aaa att aaa aca tct ggt ggg gag caa         5827
Ala Thr Gly Val Ala Leu Lys Ile Lys Thr Ser Gly Gly Glu Gln
1535            1540            1545
```

```
caa tac ccc tcc agt acc gac tct acg cct gtc gaa cac act gtc      5872
Gln Tyr Pro Ser Ser Thr Asp Ser Thr Pro Val Glu His Thr Val
1550                1555                1560 tgg ttt gat ggt acg aac aag ctg aac tat atc gcc agc tat gtg      5917
Trp Phe Asp Gly Thr Asn Lys Leu Asn Tyr Ile Ala Ser Tyr Val
1565                1570                1575 cct gtt aag ccg gat gcc acc gtt ggc aca gcg aat gcg acg gtg      5962
Pro Val Lys Pro Asp Ala Thr Val Gly Thr Ala Asn Ala Thr Val
1580                1585                1590 aat ttt agc gtc aca tac gaa taatcactga gggccagttc gctggcectt     6013
Asn Phe Ser Val Thr Tyr Glu
1595                1600 ttccattttt agtgattttt tgtaaaaatc ttctccgatc acactctccg ttgccacttt 6073 cccctctgct tgtggtctac ttaaccgtgc tctcgagcgc                       6113

<210> SEQ ID NO 16
<211> LENGTH: 537
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(534)

<400> SEQUENCE: 16 atg gag ttt tta atg aaa aag gtt gtt ttt gct ctg tct gct ctc gct    48
Met Glu Phe Leu Met Lys Lys Val Val Phe Ala Leu Ser Ala Leu Ala
1               5                   10                  15 gta gtt tcc act tct gct ttc gct gct gaa tct ggt gac ggc acc att    96
Val Val Ser Thr Ser Ala Phe Ala Ala Glu Ser Gly Asp Gly Thr Ile
            20                  25                  30 aaa ttc acc ggt gaa atc gtt gac gcg cca tgc gtc gtt tct act gac   144
Lys Phe Thr Gly Glu Ile Val Asp Ala Pro Cys Val Val Ser Thr Asp
        35                  40                  45 tcc cag aac cag gaa gtt gtg ctg ggt cag gtt aag aaa aat atc ttc   192
Ser Gln Asn Gln Glu Val Val Leu Gly Gln Val Lys Lys Asn Ile Phe
    50                  55                  60 aaa gcc att ggc gac aag tct tct tct aag cct ttc cag atc aaa ctg   240
Lys Ala Ile Gly Asp Lys Ser Ser Ser Lys Pro Phe Gln Ile Lys Leu
65                  70                  75                  80 gaa gac tgt gac atc acc tct aat acc aaa gtt aac gta agc ttc aat   288
Glu Asp Cys Asp Ile Thr Ser Asn Thr Lys Val Asn Val Ser Phe Asn
                85                  90                  95 ggc gtt ggt gat aca gac gat gcg aca ctg gtt tct gtt aac act gaa   336
Gly Val Gly Asp Thr Asp Asp Ala Thr Leu Val Ser Val Asn Thr Glu
            100                 105                 110 gca ggt gcg gca act ggc gtg ggc atc ggt atc tac gac aac gct aac   384
Ala Gly Ala Ala Thr Gly Val Gly Ile Gly Ile Tyr Asp Asn Ala Asn
        115                 120                 125 aag ctt gtt gaa atg aac acc ggt aaa tcc acc act acg ttg gct gct   432
Lys Leu Val Glu Met Asn Thr Gly Lys Ser Thr Thr Thr Leu Ala Ala
    130                 135                 140 ggt cag acc gtg ctg tac tac acc gct aac tac gtt gca aca aaa gat   480
Gly Gln Thr Val Leu Tyr Tyr Thr Ala Asn Tyr Val Ala Thr Lys Asp
145                 150                 155                 160
```

```
act gta acc act ggt tac ggt aac gca gaa gtg gac ttc aac ctg tcc       528
Thr Val Thr Thr Gly Tyr Gly Asn Ala Glu Val Asp Phe Asn Leu Ser
            165                 170                 175 tac gaa taa                                                            537
Tyr Glu <210> SEQ ID NO 17
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(696)

<400> SEQUENCE: 17 atg aac cgc tca cgt ttg ata tct tgc aca gca ctg gtg ctg gcg ttg       48
Met Asn Arg Ser Arg Leu Ile Ser Cys Thr Ala Leu Val Leu Ala Leu
1               5                   10                  15 att gct caa aac agt ttt gcc gga ggc gtg gca tta agc agc acg cgt       96
Ile Ala Gln Asn Ser Phe Ala Gly Gly Val Ala Leu Ser Ser Thr Arg
                20                  25                  30 gtt att tat gac ggt agt aga aag gaa gct tct ctt acg gta aat aat      144
Val Ile Tyr Asp Gly Ser Arg Lys Glu Ala Ser Leu Thr Val Asn Asn
            35                  40                  45 aaa agc acc acg gat gaa ttt ctc att cag tca tgg att gat gat gct      192
Lys Ser Thr Thr Asp Glu Phe Leu Ile Gln Ser Trp Ile Asp Asp Ala
50                  55                  60 aac ggt aat aaa aag acg ccc ttt atc atc act cca ccg tta ttt aaa      240
Asn Gly Asn Lys Lys Thr Pro Phe Ile Ile Thr Pro Pro Leu Phe Lys
65                  70                  75                  80 tta agc ccg act aaa aat aac gtt tta cgt att gtt aat acg acg aac      288
Leu Ser Pro Thr Lys Asn Asn Val Leu Arg Ile Val Asn Thr Thr Asn
                85                  90                  95 acg tta ccg cag gat cgc gag tcc gtt tat tgg att aac gta aaa gct      336
Thr Leu Pro Gln Asp Arg Glu Ser Val Tyr Trp Ile Asn Val Lys Ala
            100                 105                 110 att cct gcc aaa agt gaa gac gcg gaa gct aaa aac gta ctg cag atc      384
Ile Pro Ala Lys Ser Glu Asp Ala Glu Ala Lys Asn Val Leu Gln Ile
        115                 120                 125 gcc gta cgt acc cgc tta aaa ctg ttc tat cgc ccg gcg ggc ctg aaa      432
Ala Val Arg Thr Arg Leu Lys Leu Phe Tyr Arg Pro Ala Gly Leu Lys
    130                 135                 140 ggc aat agc atg gac ggc tgg aac aaa ctg cag ttc acc agc gca ggg      480
Gly Asn Ser Met Asp Gly Trp Asn Lys Leu Gln Phe Thr Ser Ala Gly
145                 150                 155                 160 gct aac cag atc aaa gtg gaa aac cca tct gcc ttt aac ctg acg ttt      528
Ala Asn Gln Ile Lys Val Glu Asn Pro Ser Ala Phe Asn Leu Thr Phe
                165                 170                 175 aat aaa ttt tat gcc aac ggc cgt gat att gaa aaa acg gga atg gtt      576
Asn Lys Phe Tyr Ala Asn Gly Arg Asp Ile Glu Lys Thr Gly Met Val
            180                 185                 190 ccg gca aaa ggc tca ttg aat att gaa ctg cca gcc ggc acc ggc aag      624
Pro Ala Lys Gly Ser Leu Asn Ile Glu Leu Pro Ala Gly Thr Gly Lys
        195                 200                 205
```

| | | |
|---|---|---|
| gta agc gaa gtt aaa tac aac att att aat gac ttt ggc act gct ggc<br>Val Ser Glu Val Lys Tyr Asn Ile Ile Asn Asp Phe Gly Thr Ala Gly<br>210                     215                     220 | | 672 |
| gac atg ttg aca cag cgc gtt aac taa<br>Asp Met Leu Thr Gln Arg Val Asn<br>225                     230 | | 699 |

<210> SEQ ID NO 18
<211> LENGTH: 2529
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<221> NAME/KEY: CDS
<222> LOCATION: (1)..(2526)

<400> SEQUENCE: 18

| | | |
|---|---|---|
| atg aca tgg acg cat ctt cct ctg ggc aat aag acc tcg cgt ttc acg<br>Met Thr Trp Thr His Leu Pro Leu Gly Asn Lys Thr Ser Arg Phe Thr<br>1                  5                   10                15 | | 48 |
| cag tct gcg ctt gcg ctg atg ata gcg ggt acg ctc ccc gcg tat gcg<br>Gln Ser Ala Leu Ala Leu Met Ile Ala Gly Thr Leu Pro Ala Tyr Ala<br>           20                  25                30 | | 96 |
| gga aca ttt aac ccg cgc ttt ctg gag gat gtg ccg ggt att gat cag<br>Gly Thr Phe Asn Pro Arg Phe Leu Glu Asp Val Pro Gly Ile Asp Gln<br>      35                  40                45 | | 144 |
| cac gtt gac ctt tca atg tat gaa tcc aat aaa gct gaa cac ctg cca<br>His Val Asp Leu Ser Met Tyr Glu Ser Asn Lys Ala Glu His Leu Pro<br>50                     55                     60 | | 192 |
| ggt aaa tac cgc gtc tcg gtg gtg gtc aac gaa aaa aaa atg gag tct<br>Gly Lys Tyr Arg Val Ser Val Val Val Asn Glu Lys Lys Met Glu Ser<br>65                     70                    75                80 | | 240 |
| cgc acc ctg gag ttt aag gca gcg aca gag gcg cag cgc gca aaa atg<br>Arg Thr Leu Glu Phe Lys Ala Ala Thr Glu Ala Gln Arg Ala Lys Met<br>                   85                   90                95 | | 288 |
| ggt gaa tcc ctg gtg ccg tgc tta agt cgc gtg cag ctt gaa gat atg<br>Gly Glu Ser Leu Val Pro Cys Leu Ser Arg Val Gln Leu Glu Asp Met<br>          100                105               110 | | 336 |
| ggc gtg cgt att gat agc ttc ccg gcg ctg aaa atg gcc ccg cct gaa<br>Gly Val Arg Ile Asp Ser Phe Pro Ala Leu Lys Met Ala Pro Pro Glu<br>          115                120               125 | | 384 |
| gcc tgt gtt gct ttt gac gac att att ccc cag gcc gcc agc cat ttc<br>Ala Cys Val Ala Phe Asp Asp Ile Ile Pro Gln Ala Ala Ser His Phe<br>130                     135                     140 | | 432 |
| gac ttt gca gac cag acc ctg atc atg agc ttc ccg cag gct gcg atg<br>Asp Phe Ala Asp Gln Thr Leu Ile Met Ser Phe Pro Gln Ala Ala Met<br>145                     150                     155                160 | | 480 |
| aag cag aca gcg cgc ggt acg gtg cca gaa tcg cag tgg gac gaa ggg<br>Lys Gln Thr Ala Arg Gly Thr Val Pro Glu Ser Gln Trp Asp Glu Gly<br>                   165                    170                   175 | | 528 |
| gtg aat gcc ctg ctg gtg gat tat aac ttt tcc ggc agc aac gcc agc<br>Val Asn Ala Leu Leu Val Asp Tyr Asn Phe Ser Gly Ser Asn Ala Ser<br>          180                185               190 | | 576 |
| tat gac gca cac gac agt gaa acc agc tac aac agc gac agc tac tat<br>Tyr Asp Ala His Asp Ser Glu Thr Ser Tyr Asn Ser Asp Ser Tyr Tyr<br>          195                200               205 | | 624 |
| ctg aat ctg cgc agc ggt atg aac ctg ggg gca tgg cgg tta cgt aac<br>Leu Asn Leu Arg Ser Gly Met Asn Leu Gly Ala Trp Arg Leu Arg Asn<br>210                     215                     220 | | 672 |

```
tat agc acc tgg acg cga aac gac ggt aac aac aca tgg gat aac att      720
Tyr Ser Thr Trp Thr Arg Asn Asp Gly Asn Asn Thr Trp Asp Asn Ile
225                 230                 235                 240 ggc aca tcc tta agc cgt gcc att gta ccg ctg aaa tca cag ctg acg      768
Gly Thr Ser Leu Ser Arg Ala Ile Val Pro Leu Lys Ser Gln Leu Thr
            245                 250                 255 ttg ggg gat acc tcc act gcc ggt gat att ttt gac agc gtt cag atg      816
Leu Gly Asp Thr Ser Thr Ala Gly Asp Ile Phe Asp Ser Val Gln Met
        260                 265                 270 cgc ggt gtg cag tta act tcc gac gaa gag atg ctg cct gac agc cag      864
Arg Gly Val Gln Leu Thr Ser Asp Glu Glu Met Leu Pro Asp Ser Gln
    275                 280                 285 cgc ggg ttt gcg ccc gtc atc cgg ggt att gcc aaa agt aac gcc gaa      912
Arg Gly Phe Ala Pro Val Ile Arg Gly Ile Ala Lys Ser Asn Ala Glu
290                 295                 300 gtt acc gtt gag cag aac aac tac gtt att tac cgt acg ttt gtt cag      960
Val Thr Val Glu Gln Asn Asn Tyr Val Ile Tyr Arg Thr Phe Val Gln
305                 310                 315                 320 ccg ggt gcg ttt gaa att aac gac ctg tat cca acc tca aac agc ggc     1008
Pro Gly Ala Phe Glu Ile Asn Asp Leu Tyr Pro Thr Ser Asn Ser Gly
            325                 330                 335 gac ctg acg gtc acc att aaa gaa tcg gac ggc agt gag cag aag ttc     1056
Asp Leu Thr Val Thr Ile Lys Glu Ser Asp Gly Ser Glu Gln Lys Phe
        340                 345                 350 gtt cag ccg ttc tcc tcg gtg gcg ctc ctc cag cgt gaa ggc cat ctc     1104
Val Gln Pro Phe Ser Ser Val Ala Leu Leu Gln Arg Glu Gly His Leu
    355                 360                 365 aaa tac agc ctt tcc gcc ggg gaa tac cgt gcc ggg aac tat aac agc     1152
Lys Tyr Ser Leu Ser Ala Gly Glu Tyr Arg Ala Gly Asn Tyr Asn Ser
370                 375                 380 gcc gag ccg aaa ttc ggg cag ctt gat gcc atg tac ggc ctg ccg tat     1200
Ala Glu Pro Lys Phe Gly Gln Leu Asp Ala Met Tyr Gly Leu Pro Tyr
385                 390                 395                 400 ggc ttt acc gtt tac ggt ggt gcg atc ttc tct gac gac tat tac tcg     1248
Gly Phe Thr Val Tyr Gly Gly Ala Ile Phe Ser Asp Asp Tyr Tyr Ser
            405                 410                 415 ctg gcg gga gga tta ggt aaa aac ttc ggt tat atc ggc gcg atc tcc     1296
Leu Ala Gly Gly Leu Gly Lys Asn Phe Gly Tyr Ile Gly Ala Ile Ser
        420                 425                 430 atc gat gta acc cag gca aaa agc aag ctg gca aat gag gag aat tcg     1344
Ile Asp Val Thr Gln Ala Lys Ser Lys Leu Ala Asn Glu Glu Asn Ser
    435                 440                 445 gaa ggt cag tct tat cgt ttc ctc tac tcc aag agc ttt aac agc ggt     1392
Glu Gly Gln Ser Tyr Arg Phe Leu Tyr Ser Lys Ser Phe Asn Ser Gly
450                 455                 460 aca gat ttc cgt ctg ctg ggt tac aag tat tcg acc agc ggt tat tac     1440
Thr Asp Phe Arg Leu Leu Gly Tyr Lys Tyr Ser Thr Ser Gly Tyr Tyr
465                 470                 475                 480 acc ttc cag gaa gcg acg gat gtg cgc agc gat gcg gac agc tct tat     1488
Thr Phe Gln Glu Ala Thr Asp Val Arg Ser Asp Ala Asp Ser Ser Tyr
            485                 490                 495 agc cag tac cac aaa cgt agt cag att cag ggc aac gtg acg cag caa     1536
Ser Gln Tyr His Lys Arg Ser Gln Ile Gln Gly Asn Val Thr Gln Gln
        500                 505                 510 ctg ggc gcc tgg ggc tcg gtc tat ttt aac gtc acg cag cag gac tac     1584
Leu Gly Ala Trp Gly Ser Val Tyr Phe Asn Val Thr Gln Gln Asp Tyr
    515                 520                 525 tgg aac gat gaa ggt aaa cag cgt tcg ctg aat gcc ggt tat aac ggc     1632
Trp Asn Asp Glu Gly Lys Gln Arg Ser Leu Asn Ala Gly Tyr Asn Gly
530                 535                 540
```

-continued

```
cgt att ggc cgc gtg aac tac agc gtt gct tac acc tgg acg aaa agc    1680
Arg Ile Gly Arg Val Asn Tyr Ser Val Ala Tyr Thr Trp Thr Lys Ser
545                 550                 555                 560 ccg gag tgg gat gag agc gat cgt tta ctg tca ttc tcc atg tcg att    1728
Pro Glu Trp Asp Glu Ser Asp Arg Leu Leu Ser Phe Ser Met Ser Ile
                565                 570                 575 cca ctg gga cgc gtg tgg agt aac tac cac ctc acg acc gat cag cat    1776
Pro Leu Gly Arg Val Trp Ser Asn Tyr His Leu Thr Thr Asp Gln His
            580                 585                 590 ggc cga acc aac cag cag tta ggg gtg agc ggc acc gcg ctg gaa gac    1824
Gly Arg Thr Asn Gln Gln Leu Gly Val Ser Gly Thr Ala Leu Glu Asp
        595                 600                 605 cac aac ctg aac tat agt gtg cag gaa ggc tac ggc agc aac ggc gtg    1872
His Asn Leu Asn Tyr Ser Val Gln Glu Gly Tyr Gly Ser Asn Gly Val
    610                 615                 620 ggt aac agc ggc agc gtg aac ctg gat tac cag ggc ggc gtg ggt agc    1920
Gly Asn Ser Gly Ser Val Asn Leu Asp Tyr Gln Gly Gly Val Gly Ser
625                 630                 635                 640 gcc agc ctg ggt tac aac tac aac cgt gac ggc cag cag gtg aac tac    1968
Ala Ser Leu Gly Tyr Asn Tyr Asn Arg Asp Gly Gln Gln Val Asn Tyr
                645                 650                 655 ggt ttg cgc ggc ggt gtg ata gcc cat agc gaa ggt atc act ctt tct    2016
Gly Leu Arg Gly Gly Val Ile Ala His Ser Glu Gly Ile Thr Leu Ser
            660                 665                 670 caa ccg ctg ggt gaa tcc atg gcc att atc tcc gcg ccg ggc gcg cgc    2064
Gln Pro Leu Gly Glu Ser Met Ala Ile Ile Ser Ala Pro Gly Ala Arg
        675                 680                 685 ggc gcg cac gtg atc aac aac ggt ggt gtg gaa gtg gac tgg atg ggt    2112
Gly Ala His Val Ile Asn Asn Gly Gly Val Glu Val Asp Trp Met Gly
    690                 695                 700 aat gcg gtc gta cct tac ctt act ccg tac cgt gaa acg gaa gtc tca    2160
Asn Ala Val Val Pro Tyr Leu Thr Pro Tyr Arg Glu Thr Glu Val Ser
705                 710                 715                 720 ctg cga agc gac agc ctg aac aac cag gtt gac ctg gat acc gcc tcc    2208
Leu Arg Ser Asp Ser Leu Asn Asn Gln Val Asp Leu Asp Thr Ala Ser
                725                 730                 735 gtc aac gta gtg ccg aca cgc ggc gcg att gtt cgt gcc cgc ttc gat    2256
Val Asn Val Val Pro Thr Arg Gly Ala Ile Val Arg Ala Arg Phe Asp
            740                 745                 750 acc cga gtg ggc tat cgt gtg ctg atg aat ctg acg cag gcc aat ggc    2304
Thr Arg Val Gly Tyr Arg Val Leu Met Asn Leu Thr Gln Ala Asn Gly
        755                 760                 765 aaa gcg gtg cct ttt ggt gct acc gcc acg ctg ctg gat acc aca aaa    2352
Lys Ala Val Pro Phe Gly Ala Thr Ala Thr Leu Leu Asp Thr Thr Lys
    770                 775                 780 gag tcc agc agc att gtg ggt gaa gac ggt cag ctt tat atc agc ggg    2400
Glu Ser Ser Ser Ile Val Gly Glu Asp Gly Gln Leu Tyr Ile Ser Gly
785                 790                 795                 800 atg ccg gag aaa ggt gcc ctt cag gtg aac tgg ggt aaa gac cag gca    2448
Met Pro Glu Lys Gly Ala Leu Gln Val Asn Trp Gly Lys Asp Gln Ala
                805                 810                 815 cag caa tgc cgc gtg gcg ttt acg ctg ccg gaa caa cag gat aat acc    2496
Gln Gln Cys Arg Val Ala Phe Thr Leu Pro Glu Gln Gln Asp Asn Thr
            820                 825                 830 ggc gtg gtg atg gcg aat gcc gtc tgc cgg taa                        2529
Gly Val Val Met Ala Asn Ala Val Cys Arg
        835                 840
```

<210> SEQ ID NO 19
<211> LENGTH: 525
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(522)

<400> SEQUENCE: 19

```
atg gac ctt ttt gtg aca aag aaa ccc agt gta tat ggc agt ata cct      48
Met Asp Leu Phe Val Thr Lys Lys Pro Ser Val Tyr Gly Ser Ile Pro
1               5                   10                  15 gcg tcg tct gta tat atc agt ggt tca att acg gta cct cag ggc tgt      96
Ala Ser Ser Val Tyr Ile Ser Gly Ser Ile Thr Val Pro Gln Gly Cys
            20                  25                  30 gaa ctc tcc agc ggc agc acg ctg gaa att ccg ttt ggg gaa ttt aag     144
Glu Leu Ser Ser Gly Ser Thr Leu Glu Ile Pro Phe Gly Glu Phe Lys
        35                  40                  45 gcc act gat ttt aaa gat cgc aaa gga caa gtt gca aag aac gcc acg     192
Ala Thr Asp Phe Lys Asp Arg Lys Gly Gln Val Ala Lys Asn Ala Thr
    50                  55                  60 aaa ttc acc aaa gag ctg cag ttt aaa tgc acc aat att tcc gat ggc     240
Lys Phe Thr Lys Glu Leu Gln Phe Lys Cys Thr Asn Ile Ser Asp Gly
65                  70                  75                  80 gta aag atc ttc ctg cgt att gag gga atg cca aac gct aat gat tcg     288
Val Lys Ile Phe Leu Arg Ile Glu Gly Met Pro Asn Ala Asn Asp Ser
                85                  90                  95 aat gcc atc gac atg ggc aac ccg gat atc ggt gcc gtc att gag ggc     336
Asn Ala Ile Asp Met Gly Asn Pro Asp Ile Gly Ala Val Ile Glu Gly
            100                 105                 110 gct aac ggt aaa att ttg gtg cca aat gac gcc agt gtt aat cag gag     384
Ala Asn Gly Lys Ile Leu Val Pro Asn Asp Ala Ser Val Asn Gln Glu
        115                 120                 125 ctg agc gta tcg ggt ctt gtt gac gac acg cac cgt acc gcc tca acg     432
Leu Ser Val Ser Gly Leu Val Asp Asp Thr His Arg Thr Ala Ser Thr
    130                 135                 140 acc att tcg gct tac cct atc agt acc acc ggc aaa ttg ccg gcc gcc     480
Thr Ile Ser Ala Tyr Pro Ile Ser Thr Thr Gly Lys Leu Pro Ala Ala
145                 150                 155                 160 ggg gat ttc gag gga att gcc acc atg cgt att gat gtg gag taa         525
Gly Asp Phe Glu Gly Ile Ala Thr Met Arg Ile Asp Val Glu
                165                 170
```

<210> SEQ ID NO 20
<211> LENGTH: 528
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(525)

<400> SEQUENCE: 20

```
atg aaa aac ctt cat gct ttg atg cca gcg tgt tta ctg ctt acc gct      48
Met Lys Asn Leu His Ala Leu Met Pro Ala Cys Leu Leu Leu Thr Ala
1               5                   10                  15 tcc gcg atg gcg gca ccg tcg aat atc ggt tct gct ggt gat atc cac      96
Ser Ala Met Ala Ala Pro Ser Asn Ile Gly Ser Ala Gly Asp Ile His
            20                  25                  30
```

| | | | | | | | | | | | | | | | | |
|---|---|---|---|---|---|---|---|---|---|---|---|---|---|---|---|---|
| ttt | acc | att | act | att | aag | gcg | gct | acc | tgt | gaa | ctg | gaa | aac | gac | agt | 144 |
| Phe | Thr | Ile | Thr | Ile | Lys | Ala | Ala | Thr | Cys | Glu | Leu | Glu | Asn | Asp | Ser | |
| | | 35 | | | | | 40 | | | | | 45 | | | | |
| atc | gac | gtc | aat | atg | gag | acc | gtg | gtg | ctt | cag | cgc | ccg | gta | aaa | gtg | 192 |
| Ile | Asp | Val | Asn | Met | Glu | Thr | Val | Val | Leu | Gln | Arg | Pro | Val | Lys | Val | |
| 50 | | | | | 55 | | | | | 60 | | | | | | |
| ggt | aaa | gag | ctg | aac | cag | aaa | aac | ttt | agc | atc | ggc | tta | aaa | gat | tgc | 240 |
| Gly | Lys | Glu | Leu | Asn | Gln | Lys | Asn | Phe | Ser | Ile | Gly | Leu | Lys | Asp | Cys | |
| 65 | | | | | 70 | | | | | 75 | | | | | 80 | |
| gcg | tat | gcc | aca | aag | gcc | agc | gtt | acg | atg | gac | ggt | tct | ccg | gac | ccg | 288 |
| Ala | Tyr | Ala | Thr | Lys | Ala | Ser | Val | Thr | Met | Asp | Gly | Ser | Pro | Asp | Pro | |
| | | | | 85 | | | | | 90 | | | | | 95 | | |
| act | gac | ccc | tcg | ctt | ttt | gcc | ctg | gat | agc | ggc | ggc | gcg | acg | ggc | gtg | 336 |
| Thr | Asp | Pro | Ser | Leu | Phe | Ala | Leu | Asp | Ser | Gly | Gly | Ala | Thr | Gly | Val | |
| | | | 100 | | | | | 105 | | | | | 110 | | | |
| gcg | tta | aaa | att | aaa | aca | tct | ggt | ggg | gag | caa | caa | tac | ccc | tcc | agt | 384 |
| Ala | Leu | Lys | Ile | Lys | Thr | Ser | Gly | Gly | Glu | Gln | Gln | Tyr | Pro | Ser | Ser | |
| | | 115 | | | | | 120 | | | | | 125 | | | | |
| acc | gac | tct | acg | cct | gtc | gaa | cac | act | gtc | tgg | ttt | gat | ggt | acg | aac | 432 |
| Thr | Asp | Ser | Thr | Pro | Val | Glu | His | Thr | Val | Trp | Phe | Asp | Gly | Thr | Asn | |
| 130 | | | | | 135 | | | | | 140 | | | | | | |
| aag | ctg | aac | tat | atc | gcc | agc | tat | gtg | cct | gtt | aag | ccg | gat | gcc | acc | 480 |
| Lys | Leu | Asn | Tyr | Ile | Ala | Ser | Tyr | Val | Pro | Val | Lys | Pro | Asp | Ala | Thr | |
| 145 | | | | | 150 | | | | | 155 | | | | | 160 | |
| gtt | ggc | aca | gcg | aat | gcg | acg | gtg | aat | ttt | agc | gtc | aca | tac | gaa | taa | 528 |
| Val | Gly | Thr | Ala | Asn | Ala | Thr | Val | Asn | Phe | Ser | Val | Thr | Tyr | Glu | | |
| | | | | 165 | | | | | 170 | | | | | 175 | | |

<210> SEQ ID NO 21
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Glu Phe Leu Met Lys Lys Val Val Phe Ala Leu Ser Ala Leu Ala
1               5                   10                  15

Val Val Ser Thr Ser Ala Phe Ala Ala Glu Ser Gly Asp Gly Thr Ile
                20                  25                  30

Lys Phe Thr Gly Glu Ile Val Asp Ala Pro Cys Val Val Ser Thr Asp
            35                  40                  45

Ser Gln Asn Gln Glu Val Val Leu Gly Gln Val Lys Lys Asn Ile Phe
        50                  55                  60

Lys Ala Ile Gly Asp Lys Ser Ser Lys Pro Phe Gln Ile Lys Leu
65                  70                  75                  80

Glu Asp Cys Asp Ile Thr Ser Asn Thr Lys Val Asn Val Ser Phe Asn
                85                  90                  95

Gly Val Gly Asp Thr Asp Asp Ala Thr Leu Val Ser Val Asn Thr Glu
            100                 105                 110

Ala Gly Ala Ala Thr Gly Val Gly Ile Gly Ile Tyr Asp Asn Ala Asn
        115                 120                 125

Lys Leu Val Glu Met Asn Thr Gly Lys Ser Thr Thr Leu Ala Ala
    130                 135                 140

Gly Gln Thr Val Leu Tyr Tyr Thr Ala Asn Tyr Val Ala Thr Lys Asp
145                 150                 155                 160

```
Thr Val Thr Thr Gly Tyr Gly Asn Ala Glu Val Asp Phe Asn Leu Ser
                165                 170                 175

Tyr Glu
```

<210> SEQ ID NO 22
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Asn Arg Ser Arg Leu Ile Ser Cys Thr Ala Leu Val Leu Ala Leu
1               5                   10                  15

Ile Ala Gln Asn Ser Phe Ala Gly Gly Val Ala Leu Ser Ser Thr Arg
                20                  25                  30

Val Ile Tyr Asp Gly Ser Arg Lys Glu Ala Ser Leu Thr Val Asn Asn
            35                  40                  45

Lys Ser Thr Thr Asp Glu Phe Leu Ile Gln Ser Trp Ile Asp Asp Ala
50                  55                  60

Asn Gly Asn Lys Lys Thr Pro Phe Ile Ile Thr Pro Pro Leu Phe Lys
65                  70                  75                  80

Leu Ser Pro Thr Lys Asn Asn Val Leu Arg Ile Val Asn Thr Thr Asn
                85                  90                  95

Thr Leu Pro Gln Asp Arg Glu Ser Val Tyr Trp Ile Asn Val Lys Ala
                100                 105                 110

Ile Pro Ala Lys Ser Glu Asp Ala Glu Ala Lys Asn Val Leu Gln Ile
            115                 120                 125

Ala Val Arg Thr Arg Leu Lys Leu Phe Tyr Arg Pro Ala Gly Leu Lys
130                 135                 140

Gly Asn Ser Met Asp Gly Trp Asn Lys Leu Gln Phe Thr Ser Ala Gly
145                 150                 155                 160

Ala Asn Gln Ile Lys Val Glu Asn Pro Ser Ala Phe Asn Leu Thr Phe
                165                 170                 175

Asn Lys Phe Tyr Ala Asn Gly Arg Asp Ile Glu Lys Thr Gly Met Val
                180                 185                 190

Pro Ala Lys Gly Ser Leu Asn Ile Glu Leu Pro Ala Gly Thr Gly Lys
            195                 200                 205

Val Ser Glu Val Lys Tyr Asn Ile Ile Asn Asp Phe Gly Thr Ala Gly
210                 215                 220

Asp Met Leu Thr Gln Arg Val Asn
225                 230
```

<210> SEQ ID NO 23
<211> LENGTH: 842
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Met Thr Trp Thr His Leu Pro Leu Gly Asn Lys Thr Ser Arg Phe Thr
1               5                   10                  15

Gln Ser Ala Leu Ala Leu Met Ile Ala Gly Thr Leu Pro Ala Tyr Ala
                20                  25                  30
```

Gly Thr Phe Asn Pro Arg Phe Leu Glu Asp Val Pro Gly Ile Asp Gln
         35                  40                  45

His Val Asp Leu Ser Met Tyr Glu Ser Asn Lys Ala Glu His Leu Pro
 50                  55                  60

Gly Lys Tyr Arg Val Ser Val Val Asn Glu Lys Lys Met Glu Ser
 65                  70                  75                  80

Arg Thr Leu Glu Phe Lys Ala Ala Thr Glu Ala Gln Arg Ala Lys Met
                 85                  90                  95

Gly Glu Ser Leu Val Pro Cys Leu Ser Arg Val Gln Leu Glu Asp Met
                100                 105                 110

Gly Val Arg Ile Asp Ser Phe Pro Ala Leu Lys Met Ala Pro Pro Glu
            115                 120                 125

Ala Cys Val Ala Phe Asp Asp Ile Ile Pro Gln Ala Ala Ser His Phe
        130                 135                 140

Asp Phe Ala Asp Gln Thr Leu Ile Met Ser Phe Pro Gln Ala Ala Met
145                 150                 155                 160

Lys Gln Thr Ala Arg Gly Thr Val Pro Glu Ser Gln Trp Asp Glu Gly
                165                 170                 175

Val Asn Ala Leu Leu Val Asp Tyr Asn Phe Ser Gly Ser Asn Ala Ser
            180                 185                 190

Tyr Asp Ala His Asp Ser Glu Thr Ser Tyr Asn Ser Asp Ser Tyr Tyr
        195                 200                 205

Leu Asn Leu Arg Ser Gly Met Asn Leu Gly Ala Trp Arg Leu Arg Asn
210                 215                 220

Tyr Ser Thr Trp Thr Arg Asn Asp Gly Asn Asn Thr Trp Asp Asn Ile
225                 230                 235                 240

Gly Thr Ser Leu Ser Arg Ala Ile Val Pro Leu Lys Ser Gln Leu Thr
                245                 250                 255

Leu Gly Asp Thr Ser Thr Ala Gly Asp Ile Phe Asp Ser Val Gln Met
            260                 265                 270

Arg Gly Val Gln Leu Thr Ser Asp Glu Glu Met Leu Pro Asp Ser Gln
        275                 280                 285

Arg Gly Phe Ala Pro Val Ile Arg Gly Ile Ala Lys Ser Asn Ala Glu
        290                 295                 300

Val Thr Val Glu Gln Asn Asn Tyr Val Ile Tyr Arg Thr Phe Val Gln
305                 310                 315                 320

Pro Gly Ala Phe Glu Ile Asn Asp Leu Tyr Pro Thr Ser Asn Ser Gly
                325                 330                 335

Asp Leu Thr Val Thr Ile Lys Glu Ser Asp Gly Ser Glu Gln Lys Phe
            340                 345                 350

Val Gln Pro Phe Ser Ser Val Ala Leu Leu Gln Arg Glu Gly His Leu
        355                 360                 365

Lys Tyr Ser Leu Ser Ala Gly Glu Tyr Arg Ala Gly Asn Tyr Asn Ser
        370                 375                 380

Ala Glu Pro Lys Phe Gly Gln Leu Asp Ala Met Tyr Gly Leu Pro Tyr
385                 390                 395                 400

Gly Phe Thr Val Tyr Gly Gly Ala Ile Phe Ser Asp Asp Tyr Tyr Ser
                405                 410                 415

Leu Ala Gly Gly Leu Gly Lys Asn Phe Gly Tyr Ile Gly Ala Ile Ser
            420                 425                 430

Ile Asp Val Thr Gln Ala Lys Ser Lys Leu Ala Asn Glu Glu Asn Ser
        435                 440                 445

-continued

```
Glu Gly Gln Ser Tyr Arg Phe Leu Tyr Ser Lys Ser Phe Asn Ser Gly
    450                 455                 460

Thr Asp Phe Arg Leu Leu Gly Tyr Lys Tyr Ser Thr Ser Gly Tyr Tyr
465                 470                 475                 480

Thr Phe Gln Glu Ala Thr Asp Val Arg Ser Asp Ala Asp Ser Ser Tyr
                485                 490                 495

Ser Gln Tyr His Lys Arg Ser Gln Ile Gln Gly Asn Val Thr Gln Gln
            500                 505                 510

Leu Gly Ala Trp Gly Ser Val Tyr Phe Asn Val Thr Gln Gln Asp Tyr
        515                 520                 525

Trp Asn Asp Glu Gly Lys Gln Arg Ser Leu Asn Ala Gly Tyr Asn Gly
    530                 535                 540

Arg Ile Gly Arg Val Asn Tyr Ser Val Ala Tyr Thr Trp Thr Lys Ser
545                 550                 555                 560

Pro Glu Trp Asp Glu Ser Asp Arg Leu Leu Ser Phe Ser Met Ser Ile
                565                 570                 575

Pro Leu Gly Arg Val Trp Ser Asn Tyr His Leu Thr Thr Asp Gln His
            580                 585                 590

Gly Arg Thr Asn Gln Gln Leu Gly Val Ser Gly Thr Ala Leu Glu Asp
        595                 600                 605

His Asn Leu Asn Tyr Ser Val Gln Glu Gly Tyr Gly Ser Asn Gly Val
    610                 615                 620

Gly Asn Ser Gly Ser Val Asn Leu Asp Tyr Gln Gly Gly Val Gly Ser
625                 630                 635                 640

Ala Ser Leu Gly Tyr Asn Tyr Asn Arg Asp Gly Gln Gln Val Asn Tyr
                645                 650                 655

Gly Leu Arg Gly Gly Val Ile Ala His Ser Glu Gly Ile Thr Leu Ser
            660                 665                 670

Gln Pro Leu Gly Glu Ser Met Ala Ile Ile Ser Ala Pro Gly Ala Arg
        675                 680                 685

Gly Ala His Val Ile Asn Asn Gly Gly Val Glu Val Asp Trp Met Gly
    690                 695                 700

Asn Ala Val Val Pro Tyr Leu Thr Pro Tyr Arg Glu Thr Glu Val Ser
705                 710                 715                 720

Leu Arg Ser Asp Ser Leu Asn Asn Gln Val Asp Leu Asp Thr Ala Ser
                725                 730                 735

Val Asn Val Val Pro Thr Arg Gly Ala Ile Val Arg Ala Arg Phe Asp
            740                 745                 750

Thr Arg Val Gly Tyr Arg Val Leu Met Asn Leu Thr Gln Ala Asn Gly
        755                 760                 765

Lys Ala Val Pro Phe Gly Ala Thr Ala Thr Leu Leu Asp Thr Thr Lys
    770                 775                 780

Glu Ser Ser Ser Ile Val Gly Glu Asp Gly Gln Leu Tyr Ile Ser Gly
785                 790                 795                 800

Met Pro Glu Lys Gly Ala Leu Gln Val Asn Trp Gly Lys Asp Gln Ala
                805                 810                 815

Gln Gln Cys Arg Val Ala Phe Thr Leu Pro Glu Gln Gln Asp Asn Thr
            820                 825                 830

Gly Val Val Met Ala Asn Ala Val Cys Arg
        835                 840
```

<210> SEQ ID NO 24
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Asp Leu Phe Val Thr Lys Lys Pro Ser Val Tyr Gly Ser Ile Pro
1               5                   10                  15

Ala Ser Ser Val Tyr Ile Ser Gly Ser Ile Thr Val Pro Gln Gly Cys
            20                  25                  30

Glu Leu Ser Ser Gly Ser Thr Leu Glu Ile Pro Phe Gly Glu Phe Lys
        35                  40                  45

Ala Thr Asp Phe Lys Asp Arg Lys Gly Gln Val Ala Lys Asn Ala Thr
    50                  55                  60

Lys Phe Thr Lys Glu Leu Gln Phe Lys Cys Thr Asn Ile Ser Asp Gly
65                  70                  75                  80

Val Lys Ile Phe Leu Arg Ile Glu Gly Met Pro Asn Ala Asn Asp Ser
                85                  90                  95

Asn Ala Ile Asp Met Gly Asn Pro Asp Ile Gly Ala Val Ile Glu Gly
            100                 105                 110

Ala Asn Gly Lys Ile Leu Val Pro Asn Asp Ala Ser Val Asn Gln Glu
        115                 120                 125

Leu Ser Val Ser Gly Leu Val Asp Asp Thr His Arg Thr Ala Ser Thr
    130                 135                 140

Thr Ile Ser Ala Tyr Pro Ile Ser Thr Thr Gly Lys Leu Pro Ala Ala
145                 150                 155                 160

Gly Asp Phe Glu Gly Ile Ala Thr Met Arg Ile Asp Val Glu
                165                 170

<210> SEQ ID NO 25
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Lys Asn Leu His Ala Leu Met Pro Ala Cys Leu Leu Leu Thr Ala
1               5                   10                  15

Ser Ala Met Ala Ala Pro Ser Asn Ile Gly Ser Ala Gly Asp Ile His
            20                  25                  30

Phe Thr Ile Thr Ile Lys Ala Ala Thr Cys Glu Leu Glu Asn Asp Ser
        35                  40                  45

Ile Asp Val Asn Met Glu Thr Val Val Leu Gln Arg Pro Val Lys Val
    50                  55                  60

Gly Lys Glu Leu Asn Gln Lys Asn Phe Ser Ile Gly Leu Lys Asp Cys
65                  70                  75                  80

Ala Tyr Ala Thr Lys Ala Ser Val Thr Met Asp Gly Ser Pro Asp Pro
                85                  90                  95

Thr Asp Pro Ser Leu Phe Ala Leu Asp Ser Gly Gly Ala Thr Gly Val
            100                 105                 110

Ala Leu Lys Ile Lys Thr Ser Gly Gly Glu Gln Gln Tyr Pro Ser Ser
        115                 120                 125

-continued

```
Thr Asp Ser Thr Pro Val Glu His Thr Val Trp Phe Asp Gly Thr Asn
    130                 135                 140

Lys Leu Asn Tyr Ile Ala Ser Tyr Val Pro Val Lys Pro Asp Ala Thr
145                 150                 155                 160

Val Gly Thr Ala Asn Ala Thr Val Asn Phe Ser Val Thr Tyr Glu
                165                 170                 175
```